(12) United States Patent
Dong et al.

(10) Patent No.: US 8,877,715 B2
(45) Date of Patent: *Nov. 4, 2014

(54) CYTOTOXIC CONJUGATES HAVING NEUROPEPTIDE Y RECEPTOR BINDING COMPOUND

(75) Inventors: Zheng Xin Dong, Holliston, MA (US); Kevin Zhou, Mansfield, MA (US); Daniel B. Deoliveira, Bellingham, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 131 days.

This patent is subject to a terminal disclaimer.

(21) Appl. No.: 13/212,242

(22) Filed: Aug. 18, 2011

(65) Prior Publication Data

US 2012/0010154 A1    Jan. 12, 2012

Related U.S. Application Data

(63) Continuation-in-part of application No. PCT/US2010/000473, filed on Feb. 19, 2010.

(60) Provisional application No. 61/208,154, filed on Feb. 20, 2009.

(51) Int. Cl.

| | | |
|---|---|---|
| *A61K 38/16* | (2006.01) | |
| *A61K 38/22* | (2006.01) | |
| *A61P 3/04* | (2006.01) | |
| *A61K 38/00* | (2006.01) | |
| *A61P 35/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A01N 51/00* | (2006.01) | |
| *A61K 31/655* | (2006.01) | |
| *A01N 45/00* | (2006.01) | |
| *A61K 31/56* | (2006.01) | |
| *A61K 31/58* | (2006.01) | |
| *A01N 43/00* | (2006.01) | |
| *A61K 31/33* | (2006.01) | |
| *A01N 55/02* | (2006.01) | |
| *A61K 31/555* | (2006.01) | |
| *A01N 43/40* | (2006.01) | |
| *A61K 31/435* | (2006.01) | |
| *A01N 43/42* | (2006.01) | |
| *A61K 31/44* | (2006.01) | |
| *A61K 31/445* | (2006.01) | |
| *A01N 43/82* | (2006.01) | |
| *A61K 31/41* | (2006.01) | |
| *C07K 14/705* | (2006.01) | |

(52) U.S. Cl.
CPC .......... *C07K 14/70571* (2013.01); *A61K 38/00* (2013.01)
USPC .......... 514/21.3; 514/5.2; 514/19.3; 514/19.4; 514/149; 514/171; 514/176; 514/183; 514/185; 514/187; 514/188; 514/277; 514/279; 514/280; 514/283; 514/315; 514/333; 514/359; 514/449; 514/450; 514/451; 514/460; 530/324

(58) Field of Classification Search
None
See application file for complete search history.

(56) References Cited

U.S. PATENT DOCUMENTS

| | | | | |
|---|---|---|---|---|
| 8,236,762 | B2 * | 8/2012 | Dong et al. | 514/11.1 |
| 8,440,611 | B2 * | 5/2013 | Dong et al. | 514/1.7 |
| 2003/0022277 | A1 * | 1/2003 | Soppet et al. | 435/69.1 |
| 2006/0099571 | A1 | 5/2006 | Altman | |
| 2008/0090758 | A1 * | 4/2008 | Guenther et al. | 514/11 |

FOREIGN PATENT DOCUMENTS

| | | | |
|---|---|---|---|
| EP | 1118336 A2 | 7/2001 | |
| WO | WO 95/00161 | 1/1995 | |
| WO | WO 97/19954 A1 | 11/1996 | |
| WO | WO 02/43776 | 6/2002 | |
| WO | WO 2007/039318 A2 | 4/2007 | |
| WO | WO 2008/051421 | 5/2008 | |
| WO | WO 2008051421 A2 * | 5/2008 | A61K 38/12 |
| WO | WO 2008/098788 | 8/2008 | |

OTHER PUBLICATIONS

Langer, M. et al., "Novel Peptide Conjugates for Tumor-Specific Chemotherapy," 2001, J. Med. Chem. 44:1341-4348.
Sun, L. et al., "Cytotoxic conjugates of peptide hormones for cancer chemotherapy", Drugs of the Future, 2008, 33(3): p. 217-223.
Soll, R. M. et al., "Novel analogues of neuropeptide Y with a preference for the Y1-receptor," 2001, Eur. J. Biochem., 268:2828-2837.

* cited by examiner

*Primary Examiner* — James H Alstrum Acevedo
*Assistant Examiner* — Thea D'Ambrosio
(74) *Attorney, Agent, or Firm* — Ipsen Bioscience; Janice Klunder

(57) ABSTRACT

There is provided a series of novel neuropeptide Y-cytotoxic conjugates, compositions comprising the same, and methods relating to their therapeutic use for the treatment of disease or condition states associated with aberrant or undesirable proliferation of cells that express NPY-Y1 receptors.

21 Claims, 3 Drawing Sheets

CYTOTOXIC CONJUGATES HAVING NEUROPEPTIDE Y RECEPTOR BINDING COMPOUND

CROSS REFERENCE TO RELATED APPLICATIONS

This application is a continuation-in-part of copending international (PCT) application no. PCT/US10/00473 filed Feb. 19, 2010, designating the US, which claims priority to U.S. provisional application No. 61/208,154 filed Feb. 20, 2009.

FIELD OF THE INVENTION

The present invention features targeted cytotoxic compounds comprising a cytotoxic moiety bound to a targeting moiety. More particularly, the present invention provides neuropeptide Y-cytotoxic conjugates, compositions comprising the same, and methods relating to their therapeutic use for the treatment of disease or condition states associated with aberrant or undesirable cellular proliferation, migration and/or physiological activity.

BACKGROUND OF THE INVENTION

Most cytotoxic drugs exhibit undesirable toxic side effects due to their lack of selective action toward the tissues or cells requiring therapeutic effect. Various approaches have been pursued to achieve the selective delivery of cytotoxic agents to a target cell type. Using biological receptor ligands as carriers of drugs to target these drugs to the cells of interest can reduce toxic side-effects and greatly improve the efficiency of drug delivery. For example, Patent Cooperation Treaty ("PCT") Publication No. WO 97/19954 discloses conjugates of an anthracycline cytotoxic agent such as doxorubicin with a peptide hormone such as LHRH, bombesin or somatostatin. The cytotoxic agent is covalently attached to the peptide via a linker having the structure: —C(O)—(CH$_2$)$_n$—C(O)—, wherein n=0-7.

Similarly, European Patent Application No. EP 1,118,336 discloses conjugates of somatostatin analogs, e.g., octreotide, lanreotide and vapreotide, and a cytotoxic drug, such as paclitaxel, doxorubicin or camptothecin, through a spacer, wherein the spacer is also indicated to have the structure: —C(O)—(CH$_2$)$_n$—C(O)—, wherein n=0-7.

U.S. Patent Application Publication No. 2002/0115596 discloses conjugates of cytotoxic agents and oligopeptides in which the amino acid sequences of the peptides are indicated to be cleaved preferentially by free prostate specific antigen. Such conjugates are said to be useful for the treatment of prostate cancer and benign prostatic hyperplasia.

U.S. Patent Application Publication No. 2003/0064984 discloses conjugates of cytotoxic analogs of CC-1065 and the duocarmycins with cleavable linker arms and a targeting agent such as an antibody or a peptide. The cytotoxic analogs are indicated to be released upon cleavage of the linker.

PCT Publication No. WO 02/34237 discloses conjugates of active agents covalently attached directly to a polypeptide. The polypeptide is said to stabilize the active agent, e.g., in the stomach, through conformational protection.

There remains, however, a significant need for targeted cytotoxic drugs with improved properties with respect to targeting specificity, systemic toxicity and pharmacokinetics.

The application of targeted cytotoxic compounds is contemplated to aid in the treatment of a number of cancerous diseases or conditions. For example, treatment of tumors or cancers which over-express neuropeptide Y ("NPY") receptors are contemplated to be targeted and treated by native human neuropeptide Y ("hNPY"), i.e., H-Tyr-Pro-Ser-Lys-Pro-Asp-Asn-Pro-Gly-Glu-Asp-Ala-Pro-Ala-Glu-Asp-Met-Ala-Arg-Tyr-Tyr-Ser-Ala-Leu-Arg-His-Tyr-Ile-Asn-Leu-Ile-Thr-Arg-Gln-Arg-Tyr-NH$_2$ (SEQ ID NO:1), or a fragment or analogue thereof, complexed with a cytotoxic moiety.

The effect of NPY can be mediated by several NPY receptor subtypes, named Y1-Y6, from which Y1, Y2, Y4 and Y5 have been extensively characterized. For a review of NPY and NPY receptors, see, e.g., C. Wahlestedt and D. Reis, Annual Review of Pharmacology and Toxicology, 33:309-352 (1993).

Based on the high density and high incidence of the NPY-Y1 receptor in breast tumor and metastasis samples, as discussed in PCT Publication No. WO 02/43776, breast cancers represent an important target for NPY-related drugs. It was also found that, as discussed in PCT Publication No. WO 02/43776, the neuropeptide Y1 receptor is exclusively expressed on tumor tissue either in combination with the Y2 receptor or alone, whereas healthy tissue only expresses the Y2 receptor. The Y1 receptor binding compound disclosed in PCT Publication No. WO 02/43776 is selected from the group consisting of the following compounds:

"[Leu$^{31}$, Pro$^{34}$]-NPY (SEQ ID NO:81), [Leu$^{31}$, Pro$^{34}$]-PYY (SEQ ID NO:82), Pro$^{34}$-NPY (SEQ ID NO:83), Pro$^{34}$-PYY (SEQ ID NO:84), NPY (SEQ ID NO:1), PYY (SEQ ID NO:80), Des Asn$^{29}$-[Trp$^{28,32}$, Nva$^{34}$]-NPY (27-36) (Balasubramaniam, Peptides 18(3), 445-457 (1997) (SEQ ID NO:85)), [Pro$^{30}$, Tyr$^{32}$, Leu$^{34}$]-NPY (28-36) (Leban et al., J. Med. Chem. 38, 1150-1157 (1995) (SEQ ID NO:86)), the dimer Bis (31/31'){[Cys$^{31}$, TrP$^{32}$, Nva$^{34}$]-NPY (31-36)} (Balasubramaniam, supra, (SEQ ID NO:87)), SR 120819A (Serradeil et al., FEBS lett. 225, 209-214 (1987)), BIBP3236 (Rudolf et al., Eur. J. Pharmacol. 271, R11-R13 (1994)), three compounds described in Daniels et al., Proc. Natl. Acad. Sci. USA 92, 9067-9071 (1995): 383U91 of the formula

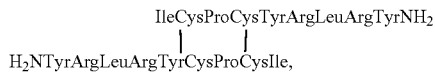

1120W91 of the formula

1229U91 of the formula

and arginine mimics."

Thus, the ability to target the NPY-Y1 receptor with Y1-selective NPY analogues conjugated to a cytotoxic moiety would aid in the treatment of cancerous diseases or conditions. Such cancers include, but are not limited to, breast cancer, ovarian cancer, glial tumors, renal cell carcinomas, nephroblastoma, and intratumoral blood vessels.

Particular advantages of the compounds of the present invention and uses thereof as treatments of tumors and cancers which represent an important target for NPY-related drugs include, but are not limited to, lessened toxic side effects, increased efficacy of treatment, and/or decreased complications from multi-drug resistance.

SUMMARY OF THE INVENTION

In one aspect, the present invention provides targeted cytotoxic compounds of the following formula (I):

$$X-B^1-B^2-B^3-B^4-Z \qquad (I)$$

wherein:
X is a cytotoxic or cytostatic agent;
$B^1$ is an rv (amino acid);
each of $B^2$, $B^3$, and $B^4$ is, independently for each occurrence, $(Doc)_m$, $(Aepa)_n$, or $-C(O)-W^1-W^2-W^3-W^4-W^5-C(O)-$, or deleted; and
Z is a moiety which binds to one or more of NPY receptor subtype(s).

In the formula (I), Z is preferably an analogue of hNPY according to the formula:

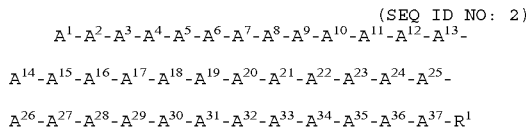
(SEQ ID NO: 2)

wherein:
$A^1$ is Tyr, $(X^1,X^2,X^3,X^4,X^5)$Phe, or $HN-CH((CH_2)_q-N(R^2R^3))-C(O)$;
$A^2$ is Pro, 3Hyp, cis-3Hyp, 4Hyp, or cis-4Hyp;
$A^3$ is Ser, Abu, Aib, Ala, Thr, or $HN-CH((CH_2)_q-N(R^2R^3))-C(O)$;
$A^4$ is Lys, Arg, hArg, Dab, Dap, Orn, or $HN-CH((CH_2)_q-N(R^2R^3))-C(O)$;
$A^5$ is Pro, 3Hyp, cis-3Hyp, 4Hyp, or cis-4Hyp;
$A^6$ is Asp, Aib, Asn, Gln, Glu, or $HN-CH((CH_2)_q-N(R^2R^3))-C(O)$;
$A^7$ is Asn, Aib, Gln, or $HN-CH((CH_2)_q-N(R^2R^3))-C(O)$;
$A^8$ is Pro, 3Hyp, cis-3Hyp, 4Hyp, or cis-4Hyp;
$A^9$ is Gly, Aib, or $HN-CH((CH_2)_q-N(R^2R^3))-C(O)$;
$A^{10}$ is Glu, Aib, Asn, Asp, Gln, or $HN-CH((CH_2)_q-N(R^2R^3))-C(O)$;
$A_{11}$ is Asp, Aib, Asn, Gln, Glu, or $HN-CH((CH_2)_q-N(R^2R^3))-C(O)$;
$A^{12}$ is Ala, Abu, Aib, Nva, Val, or $HN-CH((CH_2)_q-N(R^2R^3))-C(O)$;
$A^{13}$ is Pro, 3Hyp, cis-3Hyp, 4Hyp, or cis-4Hyp;
$A^{14}$ is Ala, Abu, Aib, Nva, Val, or $HN-CH((CH_2)_q-N(R^2R^3))-C(O)$;
$A^{15}$ is Glu, Aib, Asn, Asp, Gln, or $HN-CH((CH_2)_q-N(R^2R^3))-C(O)$;
$A^{16}$ is Asp, Aib, Asn, Gln, Glu, or $HN-CH((CH_2)_q-N(R^2R^3))-C(O)$;
$A^{17}$ is Met, Acc, Aib, Cha, Ile, Leu, hLeu, Nle, Nva, Tle, Val, or $HN-CH((CH_2)_q-N(R^2R^3))-C(O)$;
$A^{18}$ is Ala, Abu, Aib, Nva, Val, or $HN-CH((CH_2)_q-N(R^2R^3))-C(O)$;
$A^{19}$ is Arg, hArg, Apc, Dab, Dap, Lys, Orn, or $HN-CH((CH_2)_q-N(R^2R^3))-C(O)$;

$A^{20}$ is Tyr, $(X^1,X^2,X^3,X^4,X^5)$Phe, or $HN-CH((CH_2)_q-N(R^2R^3))-C(O)$;
$A^{21}$ is Tyr, $(X^1,X^2,X^3,X^4,X^5)$Phe, or $HN-CH((CH_2)_q-N(R^2R^3))-C(O)$;
$A^{22}$ is Ser, Abu, Aib, Ala, Thr, or $HN-CH((CH_2)_q-N(R^2R^3))-C(O)$;
$A^{23}$ is Ala, Abu, Aib, Nva, Val, or $HN-CH((CH_2)_q-N(R^2R^3))-C(O)$;
$A^{24}$ is Leu, Acc, Cha, Ile, hLeu, Nle, Nva, Tle, Val, or $HN-CH((CH_2)_q-N(R^2R^3))-C(O)$;
$A^{25}$ is Arg, hArg, Dab, Dap, Lys, Orn, or $HN-CH((CH_2)_q-N(R^2R^3))-C(O)$;
$A^{26}$ is His, 2Pal, 3Pal, 4Pal, or $HN-CH((CH_2)_q-N(R^2R^3))-C(O)$;
$A^{27}$ is Tyr, $(X^1,X^2,X^3,X^4,X^5)$Phe, or $HN-CH((CH_2)_q-N(R^2R^3))-C(O)$;
$A^{28}$ is Ile, Acc, Cha, Leu, hLeu, Nle, Nva, Tle, Val, or $HN-CH((CH_2)_q-N(R^2R^3))C(O)$;
$A^{29}$ is Asn, Aib, Gln, or $HN-CH((CH_2)_q-N(R^2R^3))-C(O)$;
$A^{30}$ is Leu, Acc, Cha, Ile, hLeu, Nle, Nva, Tle, Val, or $HN-CH((CH_2)_q-N(R^2R^3))-C(O)$;
$A^{31}$ is Ile, Acc, Cha, Leu, hLeu, Nle, Nva, Tle, Val, or $HN-CH((CH_2)_q-N(R^2R^3))-C(O)$;
$A^{32}$ is Thr, Aib, Ser, or $HN-CH((CH_2)_q-N(R^2R^3))-C(O)$;
$A^{33}$ is Arg, hArg, Dab, Dap, Lys, Orn, or $HN-CH((CH_2)_q-N(R^2R^3))-C(O)$;
$A^{34}$ is Gln, Asn, Dhp, 3Hyp, cis-3Hyp, 4Hyp, cis-4Hyp, Inp, Ktp, Nip, Oic, Pro, hPro, Tic, or $HN-CH((CH_2)_q-N(R^2R^3))-C(O)$;
$A^{35}$ is Arg, Aic, Apc, hArg, Dab, Dap, Lys, Orn, 4NH$_2$Phe, 4NH$_2$CH$_2$Phe, or $HN-CH((CH_2)_q-N(R^2R^3))-C(O)$;
$A^{36}$ is Tyr, Aic, $(X^1,X^2,X^3,X^4,X^5)$Phe, $HN-CH((CH_2)_q-N(R^2R^3))-C(O)$, or deleted;
$A^{37}$ is $HN-CH((CH_2)_q-N(R^2R^3))-C(O)$ or deleted;
$R^1$ is OH, NH$_2$, $(C_{1-30})$alkoxy, or $NH-X^6-CH_2-X^7$, wherein $X^6$ is a $(C_{1-40})$alkyl or $(C_{2-40})$alkenyl, and wherein $X^7$ is H, OH, CO$_2$H, or C(O)—NH$_2$;
each of $W^1$ and $W^5$ is, independently for each occurrence, $CR^4R^5$;
each of $R^4$ and $R^5$ is, independently for each occurrence, H, F, Br, Cl, I, $(C_{1-30})$alkyl, $(C_{2-30})$alkenyl, substituted $(C_{1-30})$alkyl, substituted $(C_{2-30})$alkenyl, $SR^6$, $S(O)R^7$, or $S(O)_2R^8$; or $R^4$ and $R^5$ together form a $(C_{3-30})$cycloalkyl, $(C_{3-30})$heterocycle, or $(C_{5-30})$aryl ring;
each of $R^6$, $R^7$, and $R^8$ is, independently for each occurrence, $(C_{1-30})$alkyl, $(C_{2-30})$alkenyl, substituted $(C_{1-30})$alkyl, or substituted $(C_{2-30})$alkenyl;
each of $W^2$, $W^3$, and $W^4$ is, independently for each occurrence, $CR^9R^{10}$, O, S, $(CH_2)_t$, or absent;
each of $R^9$ and $R^{19}$ is, independently for each occurrence, H, F, Br, Cl, I, $(C_{1-30})$alkyl, $(C_{2-30})$alkenyl, substituted $(C_{1-30})$alkyl, substituted $(C_{2-30})$alkenyl, $SR^6$, $S(O)R^7$, or $S(O)_2R^8$; or $R^9$ and $R^{19}$ together form a ring system;
m is, independently for each occurrence, 0, 1, 2, 3, 4, 5, 6, 7, 8, 9, or 10;
n is, independently for each occurrence, 0, 1, 2, 3, 4, 5, 6, 7, 8, 9, or 10;
q is, independently for each occurrence, 0, 1, 2, 3, 4 or 5;
t is, independently for each occurrence, 0, 1, 2, or 3;
each of $X^1$, $X^2$, $X^3$, $X^4$, and $X^5$ is, independently for each occurrence, H, F, Cl, Br, I, $(C_{1-10})$alkyl, substituted $(C_{1-10})$alkyl, aryl, substituted aryl, OH, OMe, NH$_2$, NO$_2$, or CN; and each of $R^2$ and $R^3$ is, independently for each occurrence, H, $(C_{1-40})$alkyl, $(C_{1-40})$heteroalkyl, $(C_{1-40})$acyl, $(C_{2-40})$alkenyl, $(C_{2-40})$alkynyl, aryl$(C_{1-40})$alkyl, aryl$(C_{1-40})$acyl, substituted $(C_{1-40})$alkyl, substituted $(C_{1-40})$heteroalkyl, substituted $(C_{1-40})$acyl, substituted $(C_{2-40})$alkenyl, substituted $(C_{2-40})$alkynyl, substituted aryl$(C_{1-40})$alkyl, substituted aryl$(C_{1-40})$acyl, $(C_{1-40})$alkylsulfonyl, or C(NH)—$NH_2$, wherein when $R^2$ is $(C_{1-40})$acyl, aryl$(C_{1-40})$acyl, substituted $(C_{1-40})$acyl, substituted aryl$(C_{1-40})$acyl, $(C_{1-40})$alkylsulfonyl, or C(NH)—$NH_2$, then $R^3$ is H or $(C_1-C_{40})$alkyl, $(C_{1-40})$heteroalkyl, $(C_{2-40})$alkenyl, $(C_{2-40})$alkynyl, aryl$(C_{1-40})$alkyl, substituted $(C_{1-40})$alkyl, substituted $(C_{1-40})$heteroalkyl, substituted $(C_{2-40})$alkenyl, substituted $(C_{2-40})$alkynyl, or substituted aryl$(C_{1-40})$alkyl.

A subset (IA) of the compounds covered by the above formula (I), are those in which:

X is a cytotoxic agent;
$B^1$ is rvAsp, rvD-Asp, rvCha, rvD-Cha, or rvGly;
$B^2$ is Suc;
each of $B^3$ and $B^4$ is, independently for each occurrence, $(Doc)_m$, $(Aepa)_n$, or deleted;
$A^1$ is Tyr or HN—CH$((CH_2)_q$—N($R^2R^3$))—C(O);
$A^2$ is Pro;
$A^3$ is Ser, Aib, or HN—CH$((CH_2)_q$—N($R^2R^3$))—C(O);
$A^4$ is Lys or HN—CH$((CH_2)_q$—N($R^2R^3$))—C(O);
$A^5$ is Pro;
$A^6$ is Asp, Aib, or HN—CH$((CH_2)_q$—N($R^2R^3$))—C(O);
$A^7$ is Asn, Aib, or HN—CH$((CH_2)_q$—N($R^2R^3$))—C(O);
$A^8$ is Pro;
$A^9$ is Gly, Aib, or HN—CH$((CH_2)_q$—N($R^2R^3$))—C(O);
$A^{10}$ is Glu, Aib, or HN—CH$((CH_2)_q$—N($R^2R^3$))—C(O);
$A^{11}$ is Asp, Aib, or HN—CH$((CH_2)_q$—N($R^2R^3$))—C(O);
$A^{12}$ is Ala, Aib, or HN—CH$((CH_2)_q$—N($R^2R^3$))—C(O);
$A^{13}$ is Pro;
$A^{14}$ is Ala, Aib, or HN—CH$((CH_2)_q$—N($R^2R^3$))—C(O);
$A^{15}$ is Glu, Aib, or HN—CH$((CH_2)_q$—N($R^2R^3$))—C(O);
$A^{16}$ is Asp, Aib, or HN—CH$((CH_2)_q$—N($R^2R^3$))—C(O);
$A^{17}$ is Met, A6c, Aib, Nle, or HN—CH$((CH_2)_q$—N($R^2R^3$))—C(O);
$A^{18}$ is Ala, Aib, or HN—CH$((CH_2)_q$—N($R^2R^3$))—C(O);
$A^{19}$ is Arg or HN—CH$((CH_2)_q$—N($R^2R^3$))—C(O);
$A^{20}$ is Tyr or HN—CH$((CH_2)_q$—N($R^2R^3$))—C(O);
$A^{21}$ Tyr or HN—CH$((CH_2)_q$—N($R^2R^3$))—C(O);
$A^{22}$ is Ser, Aib, or HN—CH$((CH_2)_q$—N($R^2R^3$))—C(O);
$A^{23}$ is Ala, Aib, or HN—CH$((CH_2)_q$—N($R^2R^3$))—C(O);
$A^{24}$ is Leu, A6c, or HN—CH$((CH_2)_q$—N($R^2R^3$))—C(O);
$A^{25}$ is Arg or HN—CH$((CH_2)_q$—N($R^2R^3$))—C(O);
$A^{26}$ is H is or HN—CH$((CH_2)_q$—N($R^2R^3$))—C(O);
$A^{27}$ is Tyr or HN—CH$((CH_2)_q$—N($R^2R^3$))—C(O);
$A^{28}$ is Ile, A6c, or HN—CH$((CH_2)_q$—N($R^2R^3$))—C(O);
$A^{29}$ is Asn, Aib, or HN—CH$((CH_2)_q$—N($R^2R^3$))—C(O);
$A^{30}$ is Leu, A6c, or HN—CH$((CH_2)_q$—N($R^2R^3$))—C(O);
$A^{31}$ is Ile, A6c, Leu, or HN—CH$((CH_2)_q$—N($R^2R^3$))—C(O);
$A^{32}$ is Thr, Aib, or HN—CH$((CH_2)_q$—N($R^2R^3$))—C(O);
$A^{33}$ is Arg or HN—CH$((CH_2)_q$—N($R^2R^3$))—C(O);
$A^{34}$ is Tic, Dhp, 4Hyp, Inp, Nip, Pro, hPro, or HN—CH$((CH_2)_q$—N($R^2R^3$))—C(O);
$A^{35}$ is Arg, Aic, Apc, Lys, $4NH_2$Phe, $4NH_2CH_2$Phe, or HN—CH$((CH_2)_q$—N($R^2R^3$))—C(O);
$A^{36}$ is Tyr, Aic, HN—CH$((CH_2)_q$—N($R^2R^3$))—C(O), or deleted;
$A^{37}$ is HN—CH$((CH_2)_q$—N($R^2R^3$))—C(O) or deleted;
$R^1$ is $NH_2$;
each of $R^2$ and $R^3$ is, independently for each occurrence, H or $(C_{1-30})$acyl;

provided that when $R^2$ is $(C_{1-30})$acyl, $R^3$ is H;
each of $R^4$ and $R^5$ is, independently for each occurrence, H or $(C_{1-40})$acyl;
q is 4; and
each of $X^1$, $X^2$, $X^3$, $X^4$, and $X^5$ is, independently for each occurrence, H, $CH_2NH_2$, or $NH_2$.

In the formula (I) or the subset (IA), the peptide bond between $A^{35}$ and $A^{36}$ may be replaced by a pseudopeptide bond, wherein $A^{35}$-$A^{36}$ may be Lys-ψ($CH_2$—NH)Tyr or Lys-ψ($CH_2$—N(Ac))Tyr.

In a preferred embodiment of the formula (I) or the subset (IA), Z corresponds to:

Example 1:
(SEQ ID NO: 3)
[Aib$^{10}$, 4Hyp$^{34}$]hNPY(1-36)-$NH_2$;

Example 2:
(SEQ ID NO: 4)
[Aib$^{17}$, 4Hyp$^{34}$]hNPY(1-36)-$NH_2$;

Example 3:
(SEQ ID NO: 5)
[Aib$^{11,17}$, 4Hyp$^{34}$]hNPY(1-36)-$NH_2$;

Example 4:
(SEQ ID NO: 6)
[4Hyp$^{34}$]hNPY(1-36)-$NH_2$;

Example 5:
(SEQ ID NO: 7)
[Aib$^{22}$, 4Hyp$^{34}$]hNPY(1-36)-$NH_2$;

Example 6:
SEQ ID NO: 8)
[A6c$^{31}$, 4Hyp$^{34}$]hNPY(1-36)-$NH_2$;

Example 7:
(SEQ ID NO: 9)
[A6c$^{30}$, 4Hyp$^{34}$]hNPY(1-36)-$NH_2$;

Example 8:
(SEQ ID NO: 10)
[A6c$^{28}$, 4Hyp$^{34}$]hNPY(1-36)-$NH_2$;

Example 9:
(SEQ ID NO: 11)
[Aib$^{3}$, 4Hyp$^{34}$]hNPY(1-36)-$NH_2$;

Example 10:
(SEQ ID NO: 12)
[A6c$^{24}$, 4Hyp$^{34}$]hNPY(1-36)-$NH_2$;

Example 11:
(SEQ ID NO: 13)
[Aib$^{6}$, 4Hyp$^{34}$]hNPY(1-36)-$NH_2$;

Example 12:
(SEQ ID NO: 14)
[Aib$^{18}$, 4Hyp$^{34}$]hNPY(1-36)-$NH_2$;

Example 13:
(SEQ ID NO: 15)
[Aib$^{29}$, 4Hyp$^{34}$]hNPY(1-36)-$NH_2$;

Example 14:
(SEQ ID NO: 16)
[Aib$^{32}$, 4Hyp$^{34}$]hNPY(1-36)-$NH_2$;

Example 15:
(SEQ ID NO: 17)
[Aib$^{23}$, 4Hyp$^{34}$]hNPY(1-36)-$NH_2$;

Example 16:
(SEQ ID NO: 18)
[A6c$^{17}$, 4Hyp$^{34}$]hNPY(1-36)-$NH_2$;

-continued

Example 17:
(SEQ ID NO: 19)
[Aib$^{11}$, 4Hyp$^{34}$]hNPY(1-36)-NH$_2$;

Example 18:
(SEQ ID NO: 20)
[Aib$^{12}$, 4Hyp$^{34}$]hNPY(1-36)-NH$_2$;

Example 19:
(SEQ ID NO: 21)
[Aib$^{14}$, 4Hyp$^{34}$]hNPY(1-36)-NH$_2$;

Example 20:
(SEQ ID NO: 22)
[Aib$^{15}$, 4Hyp$^{34}$]hNPY(1-36)-NH$_2$;

Example 21:
(SEQ ID NO: 23)
[Aib$^{16}$, 4Hyp$^{34}$]hNPY(1-36)-NH$_2$;

Example 22:
(SEQ ID NO: 24)
[Aib$^{7}$, 4Hyp$^{34}$]hNPY(1-36)-NH$_2$;

Example 23:
(SEQ ID NO: 25)
[Aib$^{9}$, 4Hyp$^{34}$]hNPY(1-36)-NH$_2$;

Example 24:
(SEQ ID NO: 26)
[Aib$^{10,17}$, 4Hyp$^{34}$]hNPY(1-36)-NH$_2$;

Example 25:
(SEQ ID NO: 27)
[Aib$^{15,17}$, 4Hyp$^{34}$]hNPY(1-36)-NH$_2$;

Example 26:
(SEQ ID NO: 28)
[Aib$^{11,15}$, Nle$^{17}$, 4Hyp$^{34}$]hNPY(1-36)-NH$_2$;

Example 27:
(SEQ ID NO: 29)
[Aib$^{10,15}$, Nle$^{17}$, 4Hyp$^{34}$]hNPY(1-36)-NH$_2$;

Example 28:
(SEQ ID NO: 30)
[Aib$^{11,15,17}$, 4Hyp$^{34}$]hNPY(1-36)-NH$_2$;

Example 29:
(SEQ ID NO: 31)
[Aib$^{12,15,17}$, 4Hyp$^{34}$]hNPY(1-36)-NH$_2$;

Example 30:
(SEQ ID NO: 32)
[Aib$^{10,15,17}$, 4Hyp$^{34}$]hNPY(1-36)-NH$_2$;

Example 31:
(SEQ ID NO: 33)
[Aib$^{11,16}$, 4Hyp$^{34}$]hNPY(1-36)-NH$_2$;

Example 32:
(SEQ ID NO: 34)
[Aib$^{10,16}$, 4Hyp$^{34}$]hNPY(1-36)-NH$_2$;

Example 33:
(SEQ ID NO: 35)
[Aib$^{11,17}$, 4Hyp$^{34}$, Lys$^{35}$-ψ(CH$_2$-N(Ac))Tyr$^{36}$]hNPY(1-36)-NH$_2$;

Example 34:
(SEQ ID NO: 36)
[Aib$^{17}$, 4Hyp$^{34}$, Apc$^{35}$]hNPY(1-36)-NH$_2$;

Example 35:
(SEQ ID NO: 37)
[Aib$^{17}$, 4Hyp$^{34}$, Aic$^{36}$]hNPY(1-36)-NH$_2$;

Example 36:
(SEQ ID NO: 38)
[Aib$^{17}$, 4Hyp$^{34}$, 4NH$_2$Phe$^{35}$]hNPY(1-36)-NH$_2$;

Example 37:
(SEQ ID NO: 39)
[Aib$^{17}$, 4Hyp$^{34}$, 4NH$_2$CH$_2$Phe$^{35}$]hNPY(1-36)-NH$_2$;

Example 38:
(SEQ ID NO: 40)
[Aib$^{17}$, 4Hyp$^{34}$, Lys$^{35}$-ψ(CH$_2$-NH)Tyr$^{36}$]hNPY(1-36)-NH$_2$;

Example 39:
(SEQ ID NO: 41)
[Aib$^{11,17}$, 4Hyp$^{34}$, Lys$^{35}$-ψ(CH$_2$-NH)Tyr$^{36}$]hNPY(1-36)-NH$_2$;

Example 40:
(SEQ ID NO: 42)
[Leu$^{31}$, Pro$^{34}$, Lys$^{36}$(N$^{\epsilon}$-C(O)-(CH$_2$)$_{12}$-CH$_3$)]hNPY(1-36)-NH$_2$;

Example 41:
(SEQ ID NO: 43)
[Leu$^{31}$, Pro$^{34}$, Lys$^{35}$(N$^{\epsilon}$-C(O)-(CH$_2$)$_{12}$-CH$_3$)]hNPY(1-36)-NH$_2$;

Example 42:
(SEQ ID NO: 44)
[Lys$^{24}$(N$^{\epsilon}$-C(O)-(CH$_2$)$_{12}$-CH$_3$), Leu$^{31}$, Pro$^{34}$]hNPY(1-36)-NH$_2$;

Example 43:
(SEQ ID NO: 45)
[Lys$^{23}$(N$^{\epsilon}$-C(O)-(CH$_2$)$_{12}$-CH$_3$), Leu$^{31}$, Pro$^{34}$]hNPY(1-36)-NH$_2$;

Example 44:
(SEQ ID NO: 46)
[Lys$^{22}$(N$^{\epsilon}$-C(O)-(CH$_2$)$_{12}$-CH$_3$), Leu$^{31}$, Pro$^{34}$]hNPY(1-36)-NH$_2$;

Example 45:
(SEQ ID NO: 47)
[Lys$^{21}$(N$^{\epsilon}$-C(O)-(CH$_2$)$_{12}$-CH$_3$), Leu$^{31}$, Pro$^{34}$]hNPY(1-36)-NH$_2$;

Example 46:
(SEQ ID NO: 48)
[Lys$^{20}$(N$^{\epsilon}$-C(O)-(CH$_2$)$_{12}$-CH$_3$), Leu$^{31}$, Pro$^{34}$]hNPY(1-36)-NH$_2$;

Example 47:
(SEQ ID NO: 49)
[Lys$^{19}$(N$^{\epsilon}$-C(O)-(CH$_2$)$_{12}$-CH$_3$), Leu$^{31}$, Pro$^{34}$]hNPY(1-36)-NH$_2$;

Example 48:
(SEQ ID NO: 50)
[Lys$^{18}$(N$^{\epsilon}$-C(O)-(CH$_2$)$_{12}$-CH$_3$), Leu$^{31}$, Pro$^{34}$]hNPY(1-36)-NH$_2$;

Example 49:
(SEQ ID NO: 51)
[Lys$^{17}$(N$^{\epsilon}$-C(O)-(CH$_2$)$_{12}$-CH$_3$), Leu$^{31}$, Pro$^{34}$]hNPY(1-36)-NH$_2$;

Example 50:
(SEQ ID NO: 52)
[Lys$^{16}$(N$^{\epsilon}$-C(O)-(CH$_2$)$_{12}$-CH$_3$), Leu$^{31}$, Pro$^{34}$]hNPY(1-36)-NH$_2$;

Example 51:
(SEQ ID NO: 53)
[Lys$^{15}$(N$^{\epsilon}$-C(O)-(CH$_2$)$_{12}$-CH$_3$), Leu$^{31}$, Pro$^{34}$]hNPY(1-36)-NH$_2$;

Example 52:
(SEQ ID NO: 54)
[Lys$^{14}$(N$^{\epsilon}$-C(O)-(CH$_2$)$_{12}$-CH$_3$), Leu$^{31}$, Pro$^{34}$]hNPY(1-36)-NH$_2$;

Example 53:
(SEQ ID NO: 55)
[Lys$^{12}$(N$^\epsilon$—C(O)—(CH$_2$)$_{12}$—CH$_3$), Leu$^{31}$, Pro$^{34}$]hNPY
(1-36)-NH$_2$;

Example 54:
(SEQ ID NO: 56)
[Lys$^{11}$(N$^\epsilon$—C(O)—(CH$_2$)$_{12}$—CH$_3$), Leu$^{31}$, Pro$^{34}$]hNPY
(1-36)-NH$_2$;

Example 55:
(SEQ ID NO: 57)
[Lys$^{10}$(N$^\epsilon$—C(O)—(CH$_2$)$_{12}$—CH$_3$), Leu$^{31}$, Pro$^{34}$]hNPY
(1-36)-NH$_2$;

Example 56:
(SEQ ID NO: 58)
[Lys$^9$(N$^\epsilon$—C(O)—(CH$_2$)$_{12}$—CH$_3$), Leu$^{31}$, Pro$^{34}$]hNPY
(1-36)-NH$_2$;

Example 57:
(SEQ ID NO: 59)
[Lys$^7$(N$^\epsilon$—C(O)—(CH$_2$)$_{12}$—CH$_3$), Leu$^{31}$, Pro$^{34}$]hNPY
(1-36)-NH$_2$;

Example 58:
(SEQ ID NO: 60)
[Lys$^6$(N$^\epsilon$—C(O)—(CH$_2$)$_{12}$—CH$_3$), Leu$^{31}$, Pro$^{34}$]hNPY
(1-36)-NH$_2$;

Example 59:
(SEQ ID NO: 61)
[Lys$^4$(N$^\epsilon$—C(O)—(CH$_2$)$_{12}$—CH$_3$), Leu$^{31}$, Pro$^{34}$]hNPY
(1-36)-NH$_2$;

Example 60:
(SEQ ID NO: 62)
[Lys$^3$(N$^\epsilon$—C(O)—(CH$_2$)$_{12}$—CH$_3$), Leu$^{31}$, Pro$^{34}$]hNPY
(1-36)-NH$_2$;

Example 61:
(SEQ ID NO: 63)
[Lys$^1$(N$^\epsilon$—C(O)—(CH$_2$)$_{12}$—CH$_3$), Leu$^{31}$, Pro$^{34}$]hNPY
(1-36)-NH$_2$;

Example 62:
(SEQ ID NO: 64)
[Leu$^{31}$, Pro$^{34}$, Lys$^{37}$(N$^\epsilon$—C(O)—(CH$_2$)$_{12}$—CH$_3$)]hNPY
(1-37)-NH$_2$;

Example 63:
(SEQ ID NO: 65)
[Leu$^{31}$, Lys$^{33}$(N$^\epsilon$—C(O)—(CH$_2$)$_{12}$—CH$_3$), Pro$^{34}$]hNPY
(1-36)-NH$_2$;

Example 64:
(SEQ ID NO: 66)
[Leu$^{31}$, Lys$^{32}$(N$^\epsilon$—C(O)—(CH$_2$)$_{12}$—CH$_3$), Pro$^{34}$]hNPY
(1-36)-NH$_2$;

Example 65:
(SEQ ID NO: 67)
[Lys$^{31}$(N$^\epsilon$—C(O)—(CH$_2$)$_{12}$—CH$_3$), Pro$^{34}$]hNPY(1-36)-NH$_2$;

Example 66:
(SEQ ID NO: 68)
[Lys$^{30}$(N$^\epsilon$—C(O)—(CH$_2$)$_{12}$—CH$_3$), Leu$^{31}$, Pro$^{34}$]hNPY
(1-36)-NH$_2$;

Example 67:
(SEQ ID NO: 69)
[Lys$^{29}$(N$^\epsilon$—C(O)—(CH$_2$)$_{12}$—CH$_3$), Leu$^{31}$, Pro$^{34}$]hNPY
(1-36)-NH$_2$;

Example 68:
(SEQ ID NO: 70)
[Lys$^{28}$(N$^\epsilon$—C(O)—(CH$_2$)$_{12}$—CH$_3$), Leu$^{31}$, Pro$^{34}$]hNPY
(1-36)-NH$_2$;

Example 69:
(SEQ ID NO: 71)
[Lys$^{27}$(N$^\epsilon$—C(O)—(CH$_2$)$_{12}$—CH$_3$), Leu$^{31}$, Pro$^{34}$]hNPY
(1-36)-NH$_2$;

Example 70:
(SEQ ID NO: 72)
[Lys$^{26}$(N$^\epsilon$—C(O)—(CH$_2$)$_{12}$—CH$_3$), Leu$^{31}$, Pro$^{34}$]hNPY
(1-36)-NH$_2$;

Example 71:
(SEQ ID NO: 73)
[Lys$^{25}$(N$^\epsilon$—C(O)—(CH$_2$)$_{12}$—CH$_3$), Leu$^{31}$, Pro$^{34}$]hNPY
(1-36)-NH$_2$;

Example 72:
(SEQ ID NO: 74)
[Nip$^{34}$]hNPY(1-36)-NH$_2$;

Example 73:
(SEQ ID NO: 75)
[Inp$^{34}$]hNPY(1-36)-NH$_2$;

Example 74:
(SEQ ID NO: 76)
[Dhp$^{34}$]hNPY(1-36)-NH$_2$;

Example 75:
(SEQ ID NO: 77)
[hPro$^{34}$]hNPY(1-36)-NH$_2$;

Example 76:
(SEQ ID NO: 78)
[Tic$^{34}$]hNPY(1-36)-NH$_2$;

Example 77:
(SEQ ID NO: 79)
[Leu$^{31}$, Lys$^{34}$(N$^\epsilon$—C(O)—(CH$_2$)$_{12}$—CH$_3$)]hNPY(1-36)-NH$_2$;

Example 78:
(SEQ ID NO: 1)
NPY-NH$_2$;

Example 79:
(SEQ ID NO: 80)
NPY-NH$_2$;

Example 80:
(SEQ ID NO: 81)
[Leu$^{31}$, Pro$^{34}$]-NPY-NH$_2$;

Example 81:
(SEQ ID NO: 82)
[Leu$^{31}$, Pro$^{34}$]-PYY-NH$_2$;

Example 82:
(SEQ ID NO: 83)
[Pro$^{34}$]-NPY-NH$_2$;

Example 82A:
(SEQ ID NO: 84)
[Pro$^{34}$]-PYY-NH$_2$;

Example 83:
(SEQ ID NO: 85)
Des Asn$^{29}$[Trp$^{28,32}$, Nva$^{34}$]-NPY(27-36)-NH$_2$;

Example 84:
(SEQ ID NO: 86)
[Pro$^{30}$, Tyr$^{32}$, Leu$^{34}$]-NPY(28-36)-NH$_2$;

Example 85:
(SEQ ID NO: 87)
the dimer Bis (31/31'){[Cys$^{31}$, Trp$^{32}$, Nva$^{34}$]-NPY
(31-36)-NH$_2$};

Example 86: SR120819A;

Example 87: BIBP3236;

Example 88: the compound 383U91 of the formula

Example 89: the compound 1120W91 of the formula

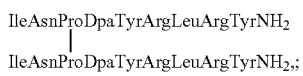

Example 90: the compound 1229U91 of the formula

Or

```
Example 90A:
                                    (SEQ ID NO: 105)
[CH₃(CH₂)₈(CO)-Tyr¹, Nle¹⁷, Pro³⁴]hNPY(1-36)-NH₂.
```

Another subset (IB) of the compounds covered by the formula (I) or the subset (IA), are those in which:
$A^1$ is Tyr;
$A^3$ is Ser;
$A^4$ is Lys;
$A^6$ is Asp;
$A^7$ is Asn;
$A^9$ is Gly;
$A^{10}$ is Glu;
$A^{11}$ is Asp;
$A^{12}$ is Ala;
$A^{14}$ is Ala;
$A^{15}$ is Glu;
$A^{16}$ is Asp;
$A^{17}$ is Aib or Nle;
$A^{18}$ is Ala;
$A^{19}$ is Arg;
$A^{20}$ is Tyr;
$A^{21}$ Tyr;
$A^{22}$ is Ser;
$A^{23}$ is Ala;
$A^{24}$ is Leu;
$A^{25}$ is Arg;
$A^{26}$ is His;
$A^{27}$ is Tyr;
$A^{28}$ is Ile;
$A^{29}$ is Asn;
$A^{30}$ is Leu;
$A^{31}$ is Ile or A6c;
$A^{32}$ is Thr;
$A^{33}$ is Arg;
$A^{34}$ is 4Hyp or Pro;
$A^{35}$ is Arg or Aic;
$A^{36}$ is Tyr, Aic, or deleted; and
$A^{37}$ is deleted.

A preferred embodiment of the present invention features a compound according to the formula (I), the subset (IA), or the subset (IB), wherein X is an anthracycline, camptothecin, a camptothecin derivative, paclitaxel, a paclitaxel derivative, doxorubicin, or a doxorubicin derivative.

In a further preferred embodiment of the present invention, X is camptothecin or a camptothecin derivative, wherein said camptothecin derivative is:

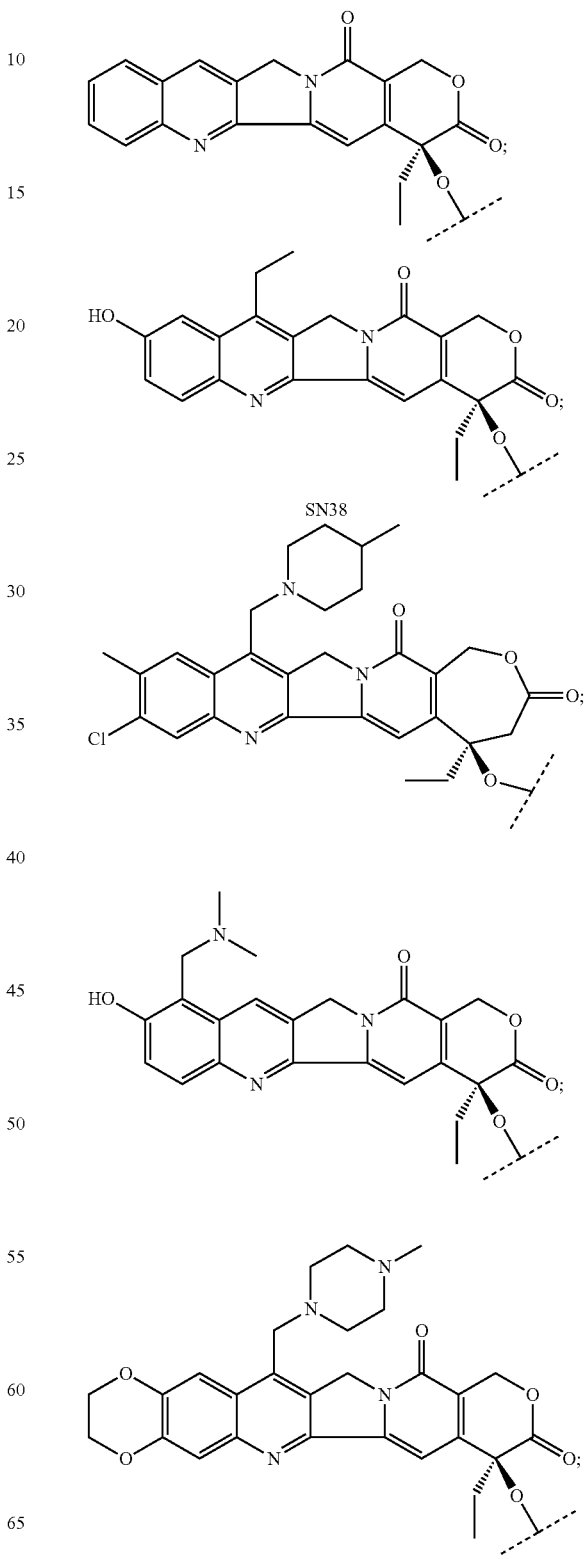

-continued

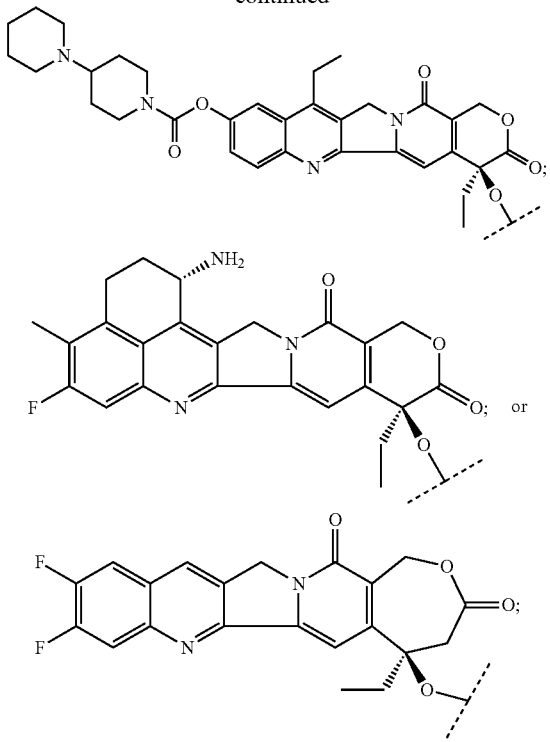

or X is paclitaxel or a paclitaxel derivative, wherein said paclitaxel derivative is:

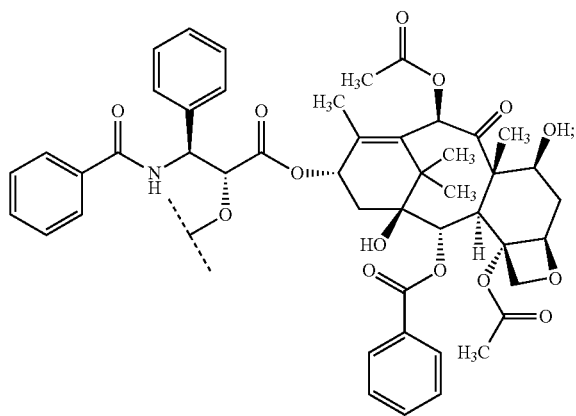

or X is doxorubicin or a doxorubicin derivative, wherein said doxorubicin derivative is:

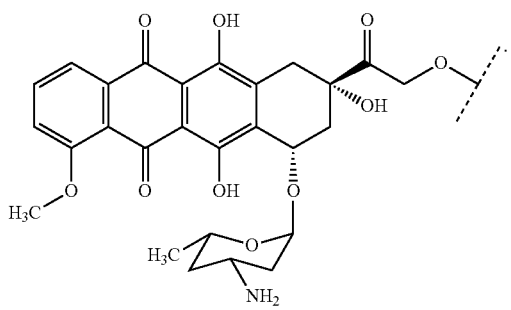

A further preferred embodiment of the invention features any one of the following compounds of the subset (IB):

Example 91:
(SEQ ID NO: 88)
[camptothecin-rvGly-Suc-Tyr$^1$, Nle$^{17}$, Pro$^{34}$]-hNPY(1-36)-NH$_2$;

Example 92:
[camptothecin-rvD-Asp-Suc-Tyr$^1$, Nle$^{17}$, 4Hyp$^{34}$]hNPY(1-36)-NH$_2$;

Example 92A:
(SEQ ID NO: 89)
[camptothecin-rvAsp-Suc-Tyr$^1$, Nle$^{17}$, 4Hyp$^{34}$]hNPY(1-36)-NH$_2$;

Example 93:
[camptothecin-rvD-Asp-Suc-Tyr$^1$, Nle$^{17}$, A6c$^{31}$, 4Hyp$^{34}$]hNPY(1-36)-NH$_2$;

Example 93A:
(SEQ ID NO: 90)
[camptothecin-rvAsp-Suc-Tyr$^1$, Nle$^{17}$, A6c$^{31}$, 4Hyp$^{34}$]hNPY(1-36)-NH$_2$;

Example 94:
(SEQ ID NO: 91)
[camptothecin-rvGly-Suc-Tyr$^1$, Nle$^{17}$, A6c$^{31}$, 4Hyp$^{34}$]hNPY(1-36)-NH$_2$;

Example 95:
[camptothecin-rvD-Asp-Suc-Tyr$^1$, Nle$^{17}$, Pro$^{34}$]hNPY(1-36)-NH$_2$;

Example 95A:
(SEQ ID NO: 92)
[camptothecin-rvAsp-Suc-Tyr$^1$, Nle$^{17}$, Pro$^{34}$]hNPY(1-36)-NH$_2$;

Example 96:
(SEQ ID NO: 93)
[camptothecin-rvCha-Suc-Tyr$^1$, Nle$^{17}$, Pro$^{34}$]hNPY(1-36)-NH$_2$;

Example 96A:
[camptothecin-rvD-Cha-Suc-Tyr$^1$, Nle$^{17}$, Pro$^{34}$]hNPY(1-36)-NH$_2$;

Example 97:
(SEQ ID NO: 94)
[camptothecin-rvGly-Suc-Tyr$^1$, Nle$^{17}$, 4Hyp$^{34}$]hNPY(1-36)-NH$_2$;

Example 98:
(SEQ ID NO: 95)
[camptothecin-rvGly-Suc-(Doc)$_3$-Tyr$^1$, Nle$^{17}$, 4Hyp$^{34}$]hNPY(1-36)-NH$_2$;

Example 99:
(SEQ ID NO: 96)
[camptothecin-rvGly-Suc-(Doc)$_3$-Aepa-Tyr$^1$, Nle$^{17}$, 4Hyp$^{34}$]hNPY(1-36)-NH$_2$;

Example 100:
[camptothecin-rvD-Asp-Suc-(Doc)$_3$-Tyr$^1$, Nle$^{17}$, 4Hyp$^{34}$]hNPY(1-36)-NH$_2$;

Example 100A:
(SEQ ID NO: 97)
[camptothecin-rvAsp-Suc-(Doc)$_3$-Tyr$^1$, Nle$^{17}$, 4Hyp$^{34}$]hNPY(1-36)-NH$_2$;

Example 101:
(SEQ ID NO: 98)
[camptothecin-rvGly-Suc-Aepa-(Doc)$_3$-Tyr$^1$, Nle$^{17}$, 4Hyp$^{34}$]hNPY(1-36)-NH$_2$;

-continued

Example 102:
[camptothecin-rvD-Asp-Suc-(Doc)₃-Aepa-Tyr¹, Nle¹⁷, 4Hyp³⁴]hNPY(1-36)-NH₂;

Example 102A: (SEQ ID NO: 99)
[camptothecin-rvAsp-Suc-(Doc)₃-Aepa-Tyr¹, Nle¹⁷, 4Hyp³⁴]hNPY(1-36)-NH₂;

Example 103:
[camptothecin-rvD-Asp-Suc-Aepa-(Doc)₃-Tyr¹, Nle¹⁷, 4Hyp³⁴]hNPY(1-36)-NH₂;

Example 103A: (SEQ ID NO: 100)
[camptothecin-rvAsp-Suc-Aepa-(Doc)₃-Tyr¹, Nle¹⁷, 4Hyp³⁴]hNPY(1-36)-NH₂;

Example 104: (SEQ ID NO: 101)
[camptothecin-rvGly-Suc-Tyr¹, Aib¹⁷, 4Hyp³⁴, Aic³⁶]hNPY(1-36)-NH₂;

Example 105: (SEQ ID NO: 102)
[camptothecin-rvGly-Suc-Tyr¹, Aib¹⁷, 4Hyp³⁴, Aic³⁵]hNPY(1-35)-NH₂;

Example 106: (SEQ ID NO: 103)
[camptothecin-rvGly-Suc-(Doc)₃-Tyr¹, Aib¹⁷, 4Hyp³⁴, Aic³⁶]hNPY(1-36)-NH₂;

Example 107: (SEQ ID NO: 104)
[camptothecin-rvGly-Suc-Aepa-(Doc)₃-Tyr¹, Aib1⁷, 4Hyp³⁴, Aic³⁶]hNPY(1-36)-NH₂;

Example 108: (SEQ ID NO: 106)
[SN38-rvGly-Suc-Tyr¹, Nle¹⁷, Pro³⁴]hNPY(1-36)-NH₂;

Example 109: (SEQ ID NO: 107)
[SN38-rvAsp-Suc-Tyr¹, Nle¹⁷, 4Hyp³⁴]hNPY(1-36)-NH₂;
or Example 110: (SEQ ID NO: 108)
[SN38-rvAsp-Suc-Tyr¹, Nle¹⁷, A6c³¹, 4Hyp³⁴]hNPY(1-36)-NH₂;

or a pharmaceutically acceptable salt thereof.

In a further aspect, the invention features a mixture of compounds of the formula (I), the subset (IA), or the subset (IB), wherein the rv (amino acid) linker occurs in the D form in some compounds in the mixture and in the L form in some compounds in the mixture. The mixture comprises, weight/weight, about 2:98, about 5:95, about 10:90, about 15:85, about 20:80, about 25:75, about 30:70, about 35:65, about 40:60, about 45:50, about 50:50, about 55:45, about 60:40, about 65:25, about 70:30, about 75:25, about 80:20, about 85:15, about 90:10, about 95:5, about 97:3 or even about 98:2 compounds in the mixture wherein the rv (amino acid) linker occurs in the D form and in the L form, respectively.

DETAILED DESCRIPTION OF THE INVENTION

Figure 1:
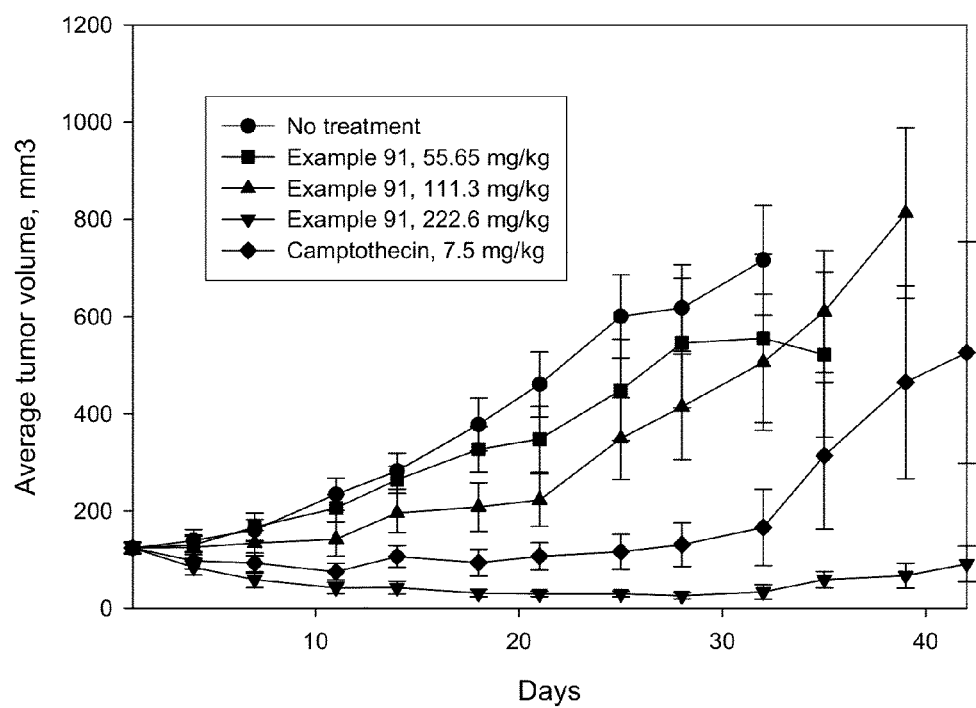
FIG. 1 shows median tumor growth curves for the compound of Example 91, which shows the in vivo effects of the compound of Example 91, at three different doses, on median tumor growth in Study A, in comparison to absence of treatment and camptothecin by itself.

As used herein the term "amino acid" refers to any natural or unnatural amino acid, including but not limited to α-amino acids, β-amino acids, or γ-amino acids, and may be either D- or L-amino acid unless otherwise indicated.

With the exception of the N-terminal amino acid, all amino acid abbreviations (e.g., Ala) in this disclosure have the structure —NH—Cl(R')—CO—, wherein R and R' each is, independently, hydrogen or the side chain of an amino acid (e.g., R=CH₃ and R'=H for Ala), or R and R' may be joined to form a ring system.

A peptide of this invention is also denoted by another format, e.g., [Pro³⁴]hNPY(1-36)—NH₂ (SEQ ID NO:83), with the substituted amino acids from the natural sequence placed between the brackets, e.g., Pro for Gln in hNPY. The designation "NH₂" in hNPY(1-36)-NH₂ (SEQ ID NO:1) indicates that the C-terminus of the peptide is amidated whereas hNPY(1-36)-OH (SEQ ID NO:1) indicates the free acid form.

The following list of some of the abbreviations used in the present application is provided for ease of reference, however, any abbreviation used in the instant application not defined herein are not used contrary to the recognized meanings thereof.

Abu α-aminobutyric acid

Acc 1-amino-1-cyclo(C₃₋₉)alkyl carboxylic acid, wherein

A3c represents 1-amino-1-cyclopropanecarboxylic acid;

A4c represents 1-amino-1-cyclobutanecarboxylic acid;

A5c represents 1-amino-1-cyclopentanecarboxylic acid; and

A6c represents 1-amino-1-cyclohexanecarboxylic acid

Adc 10-aminodecanoic acid

Ado 12-aminododecanoic acid

Aepa 4-(2-aminoethyl)-1-carboxy methyl-piperazine, represented by the structure:

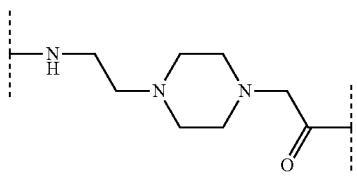

Ahp 7-aminoheptanoic acid

Ahx 6-aminohexanoic acid

Aib α-aminoisobutyric acid

Aic 2-aminoindan-2-carboxylic acid

Ala or A alanine

Anc 9-aminononanoic acid

Aoc 8-aminooctanoic acid

Apc 4-amino-4-carboxypiperidine, represented by structure:

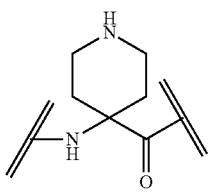

wherein, the parallel lines "=" indicate points of attachment of the moiety to another moiety or sequence.
Apn 5-aminopentanoic acid
Arg or R arginine
hArg homoarginine
Asn or N asparagine
Asp or D aspartic acid
Aun 11-aminoundecanoic acid
Cha β-cyclohexylalanine
Cys or C cysteine
Dab 2,4-diaminobutyric acid
Dap 2,3-diaminopropionic acid
Dhp 3,4-dehydroproline
Dmt 5,5-dimethylthiazolidine-4-carboxylic acid
Doc 8-amino-3,6-dioxaoctanoic acid represented by the structure:

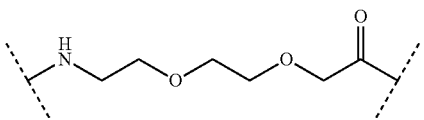

Gaba 4-aminobutyric acid
Gln or Q glutamine
Glu or E glutamic acid
Gly or G glycine
His or H histidine
3Hyp trans-3-hydroxy-L-proline, i.e., (2S,3S)-3-hydroxypyrrolidine-2-carboxylic acid
cis-3Hyp cis-3-hydroxy-L-proline, i.e., (2S,3R)-3-hydroxypyrrolidine-2-carboxylic acid
4Hyp 4-hydroxyproline, i.e., (2S,4R)-4-hydroxypyrrolidine-2-carboxylic acid
cis-4Hyp cis-4-hydroxy-L-proline, i.e., (2S,4S)-4-hydroxypyrrolidine-2-carboxylic acid
Ile or I isoleucine
Inc indoline-2-carboxylic acid
Inp isonipecotic acid
Ktp 4-ketoproline
Leu or L leucine
hLeu homoleucine
Lys or K lysine
Met or M methionine
Nip nipecotic acid
Nle norleucine
$N^\epsilon$ indicates that the entity within the parentheses is coupled to the epsilon-nitrogen of the Lys sidechain
Nva norvaline
Oic octahydroindole-2-carboxylic acid
Orn ornithine
2-Pal β-(2-pyridyl)alanine
3-Pal β-(3-pyridyl)alanine
4-Pal β-(4-pyridyl)alanine
Phe or F phenylalanine
hPhe homophenylalanine
4NH$_2$CH$_2$Phe 4-aminomethyl-phenylalanine
4NH$_2$Phe 4-amino-phenylalanine
Pro or P proline
hPro homoproline
Sar sarcosine or N-methyl glycine
Ser or S serine
Suc succinyl, represented by the structure:

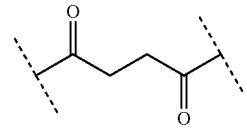

Thr or T threonine
Tic 1,2,3,4-tetrahydroisoquinoline-3-carboxylic acid
Tle tert-leucine
Val or V valine
Certain other abbreviations used herein are defined as follows:
Ac acetyl
Aloc allyloxycarbonyl
Boc tert-butyloxycarbonyl
Bhoc benzhydryloxycarbonyl
BSA bovine serum albumin
Bzl benzyl
CPT camptothecin
DCM dichloromethane
Dde 1-(4,4-dimethyl-2,6-dioxocyclohex-1-ylidine)ethyl
DIC N,N-diisopropylcarbodiimide
DIEA diisopropylethyl amine
DMA N,N-dimethylacetamide
Dmab 4-{N-(1-(4,4-dimethyl-2,6-dioxocyclohexylidene)-3-methylbutyl)-amino}benzyl
DMAP 4-(dimethylamino)pyridine
DMF dimethylformamide
DNP 2,4-dinitrophenyl
D5W 5% dextrose in water
EDC 1-ethyl-3-(3-dimethylaminopropyl)carbodiimide hydrochloride
et ethyl
EMEM Eagle's minimal essential medium
Fmoc fluorenylmethyloxycarbonyl
HATU O-(7-azabenzotriazole-1-yl)-1,1,3,3-tetramethyluronium hexafluorophosphate
HBTU 2-(1H-benzotriazole-1-yl)-1,1,3,3-tetramethyluronium hexafluorophosphate
cHex cyclohexyl
HOAT O-(7-azabenzotriazol-1-yl)-1,1,3,3-tetramethyluronium hexafluorophosphate
HOBt 1-hydroxy-benzotriazole
HPLC high performance liquid chromatography
ip intraperitoneal injection
iv tail-vein injection
MBHA 4-methylbenzhydrylamine
Mmt 4-methoxytrityl
NMP N-methyl-2-pyrrolidinone
Pbf 2,2,4,6,7-pentamethyldihydrobenzofuran-5-sulfonyl
qwk×3 once-weekly for three doses
Sc(Otf)$_3$ scandium (III) trifluoromethane sulfonate
tBu tert-butyl
TEA triethylamine
TGD tumor growth delay TGI tumor growth inhibition
TIS triisopropylsilane
TOS tosyl
Trt trityl
TFA trifluoro acetic acid
TFFH tetramethylfluoroforamidinium hexafluorophosphate
Lys-ψ(CH2-NH)Tyr has the structure of:

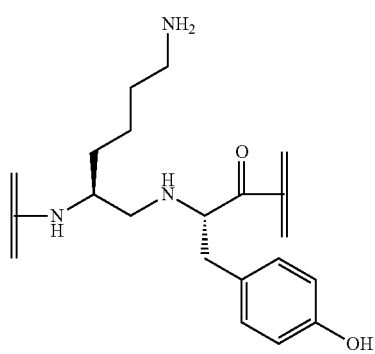

The Greek letter psi "ψ" is used herein to indicate that a peptide bond has been replaced by a pseudopeptide bond. In an amino acid sequence name, the format of the ψ term is A-ψ(X—X')—B wherein A is the amino acyl radical whose carbonyl group has been modified to X and B the amino acyl radical whose α-amino groups has been modified to X'. X and X' are shown as strings of element symbols, separated by a bond, e.g., Lys-ψ(CH$_2$—NH)-Tyr.

The designated amino acid in an rv (amino acid) is bonded in "reverse" orientation in the compound. The designated amino acid in an rv (amino acid) may have either the L or D configuration. For example, the "camptothecin-rvAsp-Suc" moiety has the structure of:

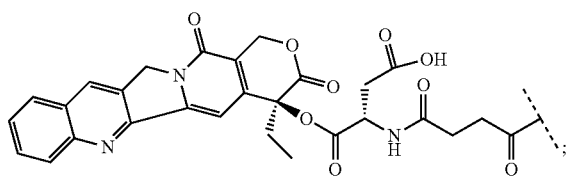

and the "camptothecin-rvD-Asp-Suc" moiety has the structure of:

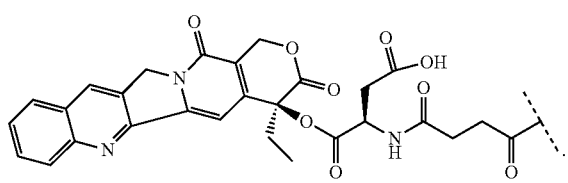

"rvD/Lamino acid" or "rv (D-/L-amino acid)" refers to a mixture of the L and D configuration of the designated amino acid. For example, the "camptothecin-rvD/Lasp-Suc" moiety comprises a mixture of

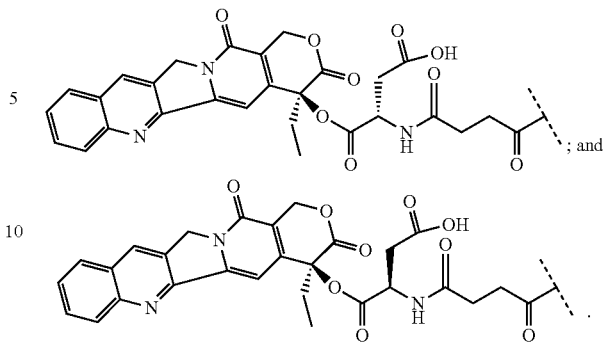

"Alkyl" refers to a hydrocarbon group containing one or more carbon atoms, where multiple carbon atoms if present are joined by single bonds, examples of which include but are not limited to methyl, ethyl, propyl and butyl. The alkyl hydrocarbon group may be straight-chain or contain one or more branches or cyclic groups, examples of which include, but are not limited to, isopropyl and tertbutyl.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), OH, CN, SH, NH$_2$, NHCH$_3$, NO$_2$, (C$_{1-2}$) alkyl substituted with 1 to 6 halogens, CF$_3$, OCH$_3$, OCF$_3$, and (CH$_2$)$_{0-4}$—COOH. In different embodiments, 1, 2, 3 or 4 substituents are present. The presence of (CH$_2$)$_{0-4}$—COOH results in the production of an alkyl acid. Examples of alkyl acids containing (CH$_2$)$_{0-4}$—COOH include, but are not limited to, 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following atoms or groups: amino, amido, O, S, N, and carbonyl. In different embodiments, 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), OH, CN, SH, NH$_2$, NHCH$_3$, NO$_2$, (C$_{1-2}$) alkyl substituted with 1 to 6 halogens, CF$_3$, OCH$_3$, OCF$_3$, and (CH$_2$)$_{0-4}$—COOH. In different embodiments, 1, 2, 3 or 4 substituents are present.

"Alkenyl" refers to a hydrocarbon group made up of two or more carbons where one or more carbon-carbon double bonds are present, examples of which include, but are not limited to, vinyl, allyl, butenyl and propenyl. The alkenyl hydrocarbon group may be straight-chain or contain one or more branches or cyclic groups, examples of which include, but are not limited to, n-butenyl versus t-butenyl, and n-pentenyl compared to cyclopentenyl.

"Substituted alkenyl" refers to an alkenyl wherein one or more hydrogens are replaced with one or more substituents selected from the group consisting of halogen (i.e., fluorine, chlorine, bromine, and iodine), OH, CN, SH, NH$_2$, NHCH$_3$, NO$_2$, (C$_{1-2}$) alkyl substituted with 1 to 6 halogens, CF$_3$, OCH$_3$, OCF$_3$, and (CH$_2$)$_{0-4}$—COOH. In different embodiments, 1, 2, 3 or 4 substituents are present.

"Aryl" refers to an optionally substituted aromatic group with at least one ring having a conjugated π-electron system containing up to two conjugated or fused ring systems. Aryl includes, but is not limited to, carboxylic aryl, heterocyclic aryl and biaryl groups. Preferably, an aryl is a 5- or 6-membered ring. Preferred atoms for a heterocyclic aryl include, but are not limited to, one or more of sulfur, oxygen and nitrogen. Examples of aryl include, but are not limited to, phenyl, 1-naphthyl, 2-naphthyl, indole, quinoline, 2-imidazole, and 9-anthracene. Aryl substituents are selected from the group consisting of $(C_{1-4})$alkyl, $(C_{1-4}$ alkoxy, halogen (i.e., fluorine, chlorine, bromine, and iodine), OH, CN, SH, $NH_2$, $NO_2$, $(C_{1-2})$ alkyl substituted with 1 to 5 halogens, $CF_3$, $OCF_3$, and $(CH_2)_{0-4}$—COOH. In different embodiments, aryl contains 0, 1, 2, 3 or 4 substituents.

"Alkylaryl" refers to an "alkyl" joined to an "aryl," as defined above.

The term "cycloalkyl" is intended to include a mono-cycloalkyl group or a bi-cycloalkyl group of the indicated carbon number known to those of skill in the art.

The term "heterocycle" includes mono-cyclic and bi-cyclic systems having one or more heteroatoms, such as oxygen, nitrogen and sulfur. The ring systems may be aromatic, for example, pyridine, indole, quinoline, pyrimidine, thiophene (also known as thienyl), furan, benzothiophene, tetrazole, dihydroindole, indazole, N-formylindole, benzimidazole, thiazole, and thiadiazole. The ring systems also may be non-aromatic, for example, but not limited to, pyrrolidine, piperidine, morpholine, and the like.

Synthesis

The compounds of this invention can be and were produced using the techniques disclosed in the examples herein as well as techniques that are well known in the art. For example, a polypeptide region of an NPY analogue can be chemically or biochemically synthesized and/or modified. See, e.g., Stewart, J. M., et al., *Solid Phase Synthesis*, Pierce Chemical Co., 2d ed. (1984); and see, e.g., Sambrook et al., *Molecular Cloning, A Laboratory Manual*, $2^{nd}$ ed., Cold Spring Harbor Laboratory Press (1989) for examples of techniques for biochemical synthesis involving the introduction of a nucleic acid into a cell and expression of nucleic acids. The following examples also illustrate methods for synthesizing the targeted cytotoxic compounds of the present invention. The examples are provided for the purpose of illustration and are not meant to limit the scope of the present invention in any manner.

```
Example 1:
[Aib¹⁰, 4Hyp³⁴]hNPY(1-36)-NH₂     (SEQ ID NO: 3)
```

The titled peptide was assembled using Fmoc-chemistry. The C-terminal portion of the peptide (residues 18-36) was synthesized on ABI 433A Peptide Synthesizer (Applied Biosystems, Foster City, Calif., USA) at the 1.0 mmole scale. The reaction vessel containing 1.37 g of 0.73 mmol/Rink Amide MBHA resin (Novabiochem, San Diego, Calif., USA) was placed in a reaction vessel. The resin was then treated with 10 ml of NMP for 15 minutes to swell the resin. The ABI Fast-Moc 1.0® protocol was used to generate the peptide.

Each cycle comprised of deblocking the N-terminal Fmoc using 20% piperidine followed by extensive NMP washing. Pre-packaged 1.0 mmole cartridges of each amino acid were then dissolved in 0.45M HOBT/HBTU. After enough time was allotted for dissolution of the amino acid, it was automatically transferred to the activation vessel. Two more 1.0 mmole amino acid cartridges were dissolved and transferred to the activation vessel for a total of 3 equivalents of amino acid used per coupling step. DIPEA, 3 ml of a 2M solution, was then introduced to the activation vessel for a total of 6 eq. DIPEA.

This entire mixture was then introduced to the resin and allowed to mix for 15 minutes. The reaction vessel was emptied, washed with NMP and then followed by a second coupling step. Following the second coupling step, the resin was again thoroughly washed. Each amino acid was double-coupled in a similar fashion. Following the coupling step of the first Tyr residue, for each of the next 4 coupling steps, and each Arg coupling step, the resin was capped with 5 ml of capping solution (0.5M acetic anhydride/0.13M DIPEA/0.01M HOBT) to block any unacylated resin sites. The following amino acid cartridges were used for the coupling steps: Cycle 1) Fmoc-Tyr(tBu)-OH; Cycle 2) Fmoc-Arg(Pbf)-OH; Cycle 3) Fmoc-4Hyp-OH; Cycle 4) Fmoc-Arg(Pbf)-OH; Cycle 5) Fmoc-Thr(tBu)-OH; Cycle 6) Fmoc-Ile-OH; Cycle 7) Fmoc-Leu-OH; Cycle 8) Fmoc-Asn(Trt)-OH; Cycle 9) Fmoc-Ile-OH; Cycle 10) Fmoc-Tyr(tBu)-OH; Cycle 11) Fmoc-His(Trt)-OH; Cycle 12) Fmoc-Arg(Pbf)-OH; Cycle 13) Fmoc-Leu-OH; Cycle 14) Fmoc-Ala-OH; Cycle 15) Fmoc-Ser(tBu)-OH; Cycle 16) Fmoc-Tyr(tBu)-OH; Cycle 17) Fmoc-Tyr(tBu)-OH; Cycle 18) Fmoc-Arg(Pbf)-OH; and Cycle 19) Fmoc-Ala-OH.

Following the last coupling cycle, the resin was washed with NMP, followed by standard N-terminal Fmoc deblocking, washed with NMP followed by DCM. After assembling the C-terminal portion of the peptide backbone (residues 18-36), one tenth of the resin (0.1 mmole) was used to construct the N-terminal portion of the peptide, with the remainder conserved. The N-terminal portion of the titled peptide (residues 1-17) was constructed using microwave-assisted Fmoc Chemistry on Liberty Peptide Synthesizer (CEM, Matthews, N.C., USA) at the 0.1 mmole scale. The resin from the previous synthesis was placed in a 50 ml conical tube along with 15 ml of DMF and loaded onto a resin position on the synthesizer. The resin was then quantitatively transferred to the reaction vessel via the automated process. The standard Liberty synthesis protocol for 0.1 mmole scale synthesis was used. This protocol involves deprotecting the N-terminal Fmoc moiety via an initial treatment with 7 ml of 20% piperidine, containing 0.1M HOBT, in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration.

The resin was then drained and thoroughly washed with DMF several times. The protected amino acid, Fmoc-Met-OH, prepared as 0.2M stock solution in DMF, was then added (2.5 ml, 5 equivalents), followed by 1.0 ml of 0.45M (4.5 eq.) HBTU in DMF. This was followed by the addition of 0.5 ml of 2M (10 eq.) DIPEA in NMP. The coupling step was performed for 5 minutes using 20 watts of microwave power, a maximum temperature of 75° C., and the same rate of nitrogen bubbling. Following the initial coupling step, the reaction vessel was drained to waste and the coupling step repeated.

Cycle 2 was then initiated similar to Cycle 1. All amino acids were introduced similarly and a double-coupling strategy was employed throughout the entire sequence. Residues 9-10 (Gly-Aib) contained a capping procedure immediately following the coupling step. Capping was performed by adding 7 ml of 0.5M acetic anhydride, containing 0.015M HOBT in NMP, along with 2 ml of the 2M DIPEA solution using a multi-step microwave protocol: 50 watts of power for 30 seconds (65° C. maximum temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 20) Fmoc-Met-OH; Cycle 21) Fmoc-Asp (OtBu)-OH; Cycle 22) Fmoc-Glu(OtBu)-OH; Cycle 23) Fmoc-Ala-OH; Cycle 24) Fmoc-Pro-OH; Cycle 25) Fmoc-Ala-OH; Cycle 26) Fmoc-Asp(OtBu)-OH; Cycle 27) Fmoc-Aib-OH; Cycle 28) Fmoc-Gly-OH; Cycle 29) Fmoc-Pro-OH; Cycle 30) Fmoc-Asn(Trt)-OH; Cycle 31) Fmoc-Asp (OtBu)-OH; Cycle 32) Fmoc-Pro-OH; Cycle 33) Fmoc-Lys (Boc)-OH; Cycle 34) Fmoc-Ser(tBu)-OH; Cycle 35) Fmoc-Pro-OH; Cycle 36) Fmoc-Tyr(tBu)-OH.

Once the peptide backbone was complete, standard piperidine treatment was used to remove the N-terminal Fmoc group using the standard deprotection procedure described previously. The resin was then thoroughly washed with DMF and then transferred back to the 50 ml conical tube using DMF as the transfer solvent.

The resin was deprotected and cleaved from the resin via treatment with 5 ml of the following reagent: 5% TIS, 2% water, 5% (w/v) DTT, and 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted and the peptide re-suspended in fresh ether. The ether workup was performed a total of 2 times. Following the last ether wash, the peptide was allowed to air dry to remove residual ether. The peptide pellet was resuspended in 8 ml of acetonitrile followed by 8 ml of de-ionized water and allowed to fully dissolve.

The peptide solution was then analyzed by mass spectrometry. Mass analysis employing electrospray ionization identified a main product containing a mass of 4212.1, corresponding to the desired product. Analytical HPLC analysis, employing a 250×4.6 mm C18 column (Phenomenex, Torrance, Calif., USA) using a gradient of 2-60% acetonitrile (0.1% TFA) over 30 minutes, identified a main product with 45% purity. The crude peptide was then purified on a preparative HPLC equipped with a C18 reverse phase column using a 10-60% acetonitrile (0.1% TFA) over 50 minutes at a 10 ml/min flow rate. The purified product was analyzed by HPLC for purity (>99%) and mass spectrometry (4212.8 da), with the experimental mass corresponding well to the expected mass of 4212.7. The peptide was subsequently lyophilized producing 39 mg of purified product representing a 9% yield.

```
Example 91:
                                      (SEQ ID NO: 88)
[camptothecin-rvGly-Suc-Tyr¹, Nle¹⁷, Pro³⁴]hNPY (1-36)-NH₂
```

4482. CPT-rvGly-Boc

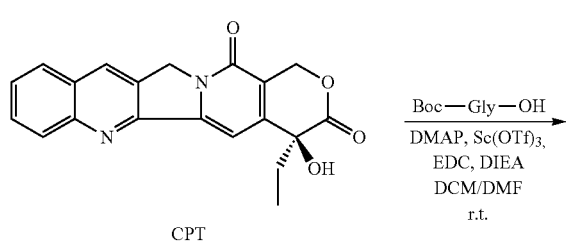

CPT

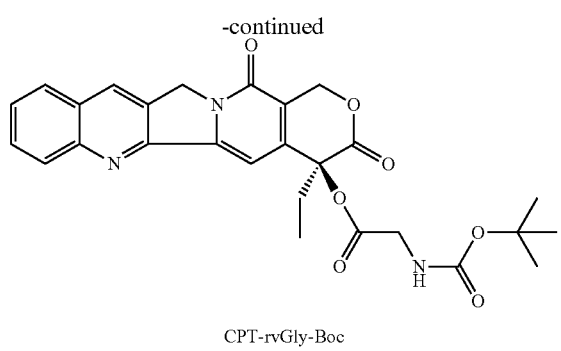

CPT-rvGly-Boc

Camptothecin ("CPT") (6.0 g, 17.2 mmol), Boc-Gly-OH (10.0 g, 57.0 mmol), DMAP (6.4 g, 52.2 mmol), Sc(Otf)₃ (5.0 g, 10.2 mmol) and DIEA (6.0 mL, 34.4 mmol) were added into a 500-mL round bottom flask containing DCM/DMF (300/30 mL). After stirring for 10 minutes, EDC (13.0 g, 68.0 mmol) was added in one portion. The reaction mixture was stirred at room temperature for 16 hours. It gradually changed from a suspension to a clear solution. The DCM was removed on a rotavap and the remaining DMF solution was taken in MeOH (200 mL) and put in a refrigerator. A yellow crystal (formed over 2-16 hours) was filtered and washed with hexanes. A solid was obtained after air-drying (5.9 g).

2. CPT-rvGly-NH₂

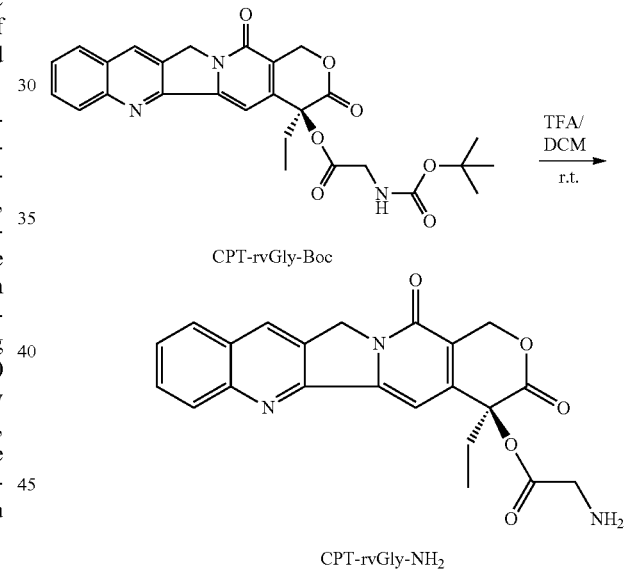

To a solution of CPT-rvGly-Boc (3.3 g, 6.5 mmol) in DCM (70 mL), TFA (70 mL) was added. The reaction mixture was stirred at room temperature for 2 hours. Ether (450 mL) was then added and a yellow solid was obtained after filtration followed by washing with ether (3.1 g).

3. CPT-rvGly-Suc-OH

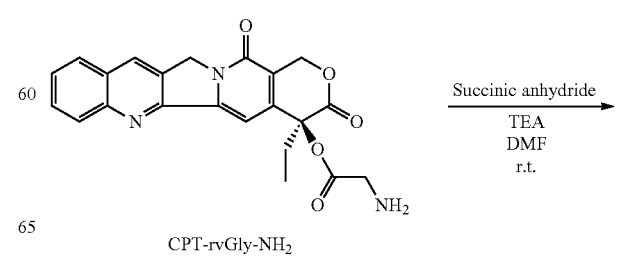

CPT-rvGly-NH₂

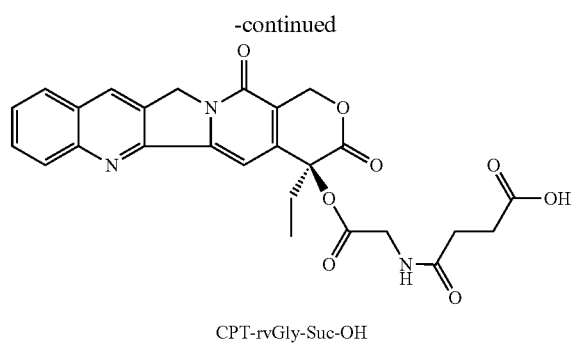

CPT-rvGly-Suc-OH

CPT-rvGly-NH$_2$ (6.5 mmol) obtained above was dissolved in DMF (90 mL). Succinic anhydride (1.2 g, 11.9 mmol) and TEA (3.2 mL, 22.7 mmol) were added. The mixture was stirred at room temperature for 4 hours. The mixture was then poured into a beaker containing iced water (1200 mL) and treated with concentrated HCl to let pH-3. A yellow solid was filtered and washed with water. A solid was obtained after drying on high vacuum (3.77 g).

4. Protected Peptide (SEQ ID NO: 88)
[Tyr$^1$, Nle$^{17}$, Pro$^{34}$]hNPY(1-36)-Rink Amide MBHA Resin

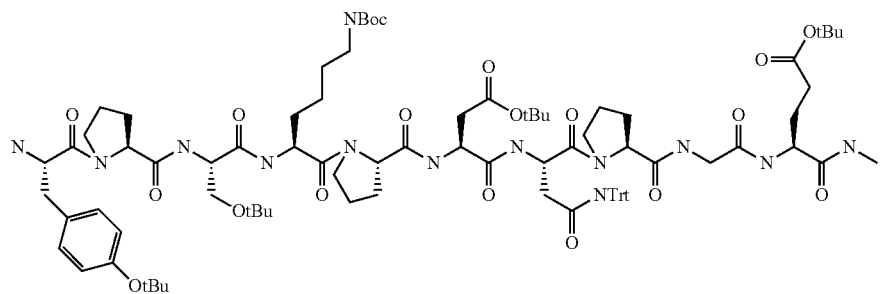

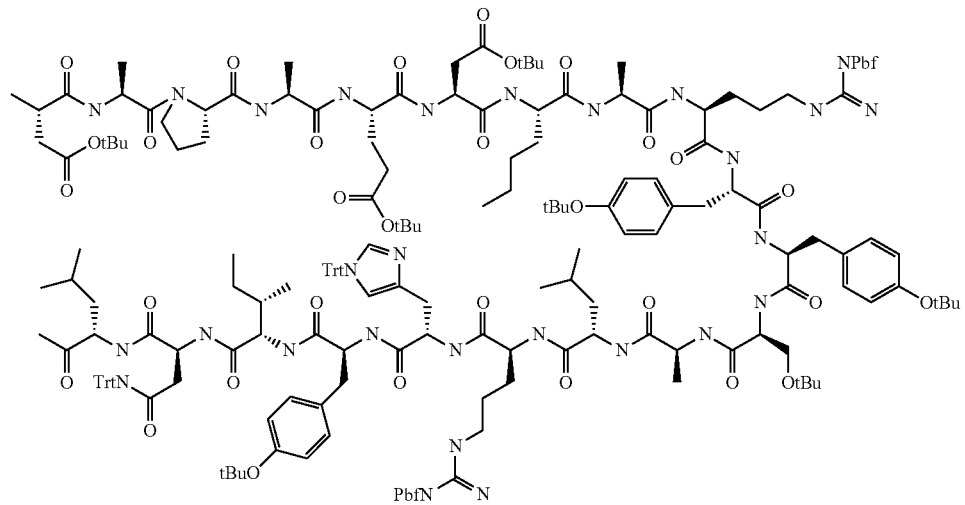

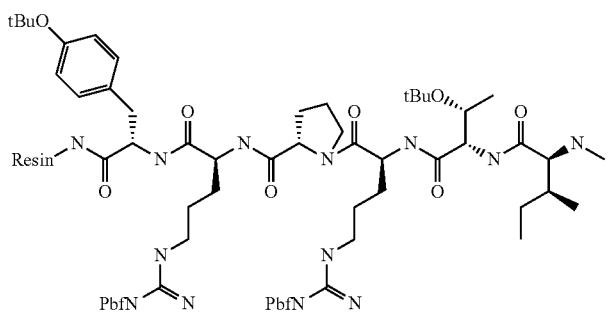

was prepared on ABI 433a Peptide Synthesizer, at 0.25 mmol scale using Rink Amide MBHA resin (0.69 mmol/g loading, 0.365 g) and Fmoc chemistry prolonged double coupling, with the final deprotection to remove Fmoc group from Tyr¹. After the synthesis was complete, the protected peptide on the resin was air dried whereby a solid was obtained (0.455 g).

5.

[camptothecin-rvGly-Suc-Tyr¹, Nle¹⁷, Pro³⁴]hNPY (1-36)-NH₂ (SEQ ID NO: 88)

To a mixture of the protected peptide on resin (0.2 g, 0.11 mmol) and DMF (5 mL), CPT-rvGly-Suc-OH (190 mg, 0.38 mmol), HOBt (85 mg, 0.63 mmol), DIC (0.098 mL, 0.63 mmol) and DIEA (1.2 mL, 6.9 mmol) were added. After shaking for 16 hours, the mixture was drained and washed 3 times with DMF and then 3 times with DCM. The resin was then treated with TFA:TIS:water (9.5:0.8:0.85 mL) for 3 hours. Upon the filtration to remove the resin, ether (80 mL) was added to the filtrate. A yellow precipitate was collected using a centrifuge. Crude product was re-dissolved in 10 mL water/5 mL acetonitrile and purified on prep HPLC (1-in C18 column). Fractions containing the desired product (confirmed by MS and HPLC) were pooled and lyophilized. A yellow

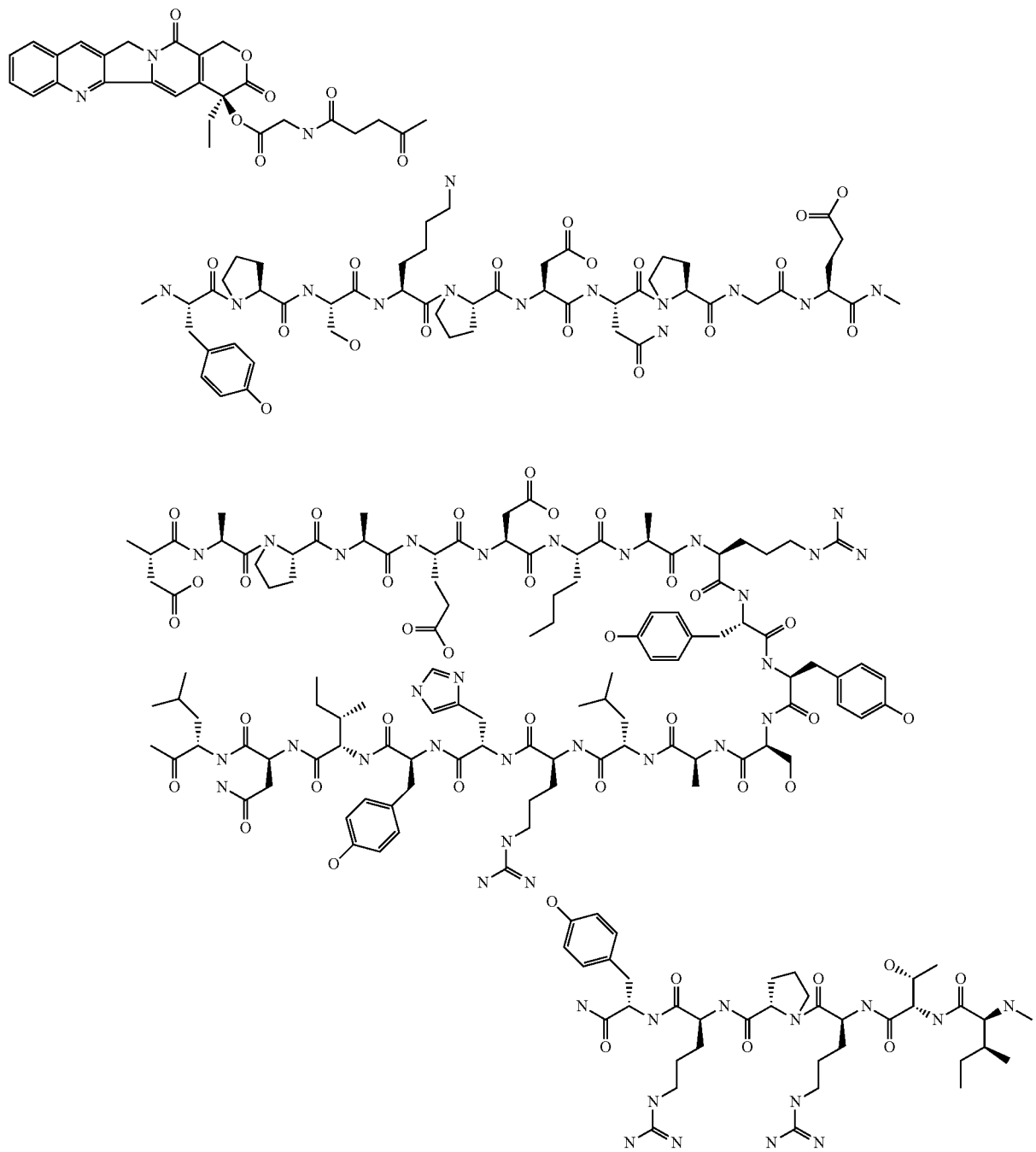

solid was obtained (28.4 mg). ESI-MS analysis gave the molecular weight at 4709.9 (in agreement with the calculated molecular weight of 4709.9). Purity was 97.5% based on HPLC analysis.

Example 92/92A:

(SEQ ID NO: 89)
[camptothecin-rvD/Lasp-Suc-Tyr¹, Nle¹⁷, 4Hyp³⁴]
hNPY(1-36)-NH₂

4482. CPT-rvD/Lasp(OtBu)-Boc

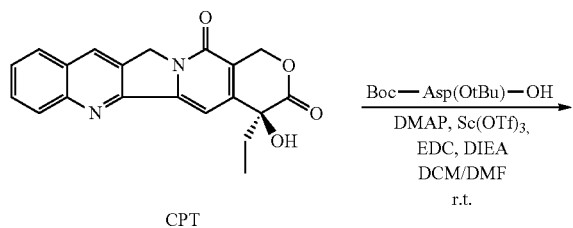

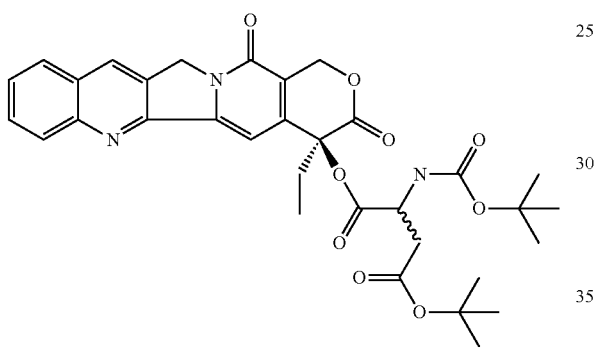

CPT (1.5 g, 4.3 mmol), Boc-Asp(OtBu)-OH (4.1 g, 14.2 mmol), DMAP (1.6 g, 13.1 mmol), Sc(Otf)₃ (1.25 g, 2.5 mmol) and DIEA (1.5 mL, 8.6 mmol) were added into a 250-mL round bottom flask containing DCM/DMF (75/20 mL). After stirring for 10 minutes, one portion of EDC (3.25 g, 17.0 mmol) was added. The reaction mixture was stirred at room temperature for 2-16 hours. The mixture gradually changed from a suspension to a clear solution. The DCM was removed on a rotavap and the remaining DMF solution was treated with iced water. After filtration and drying on high vacuum, a yellow solid was obtained (3.4 g). HPLC analysis indicated two peaks indicating both the D- and L-isomer in a ratio of 4:1.

2. CPT-rvD/Lasp(OtBu)-NH₂

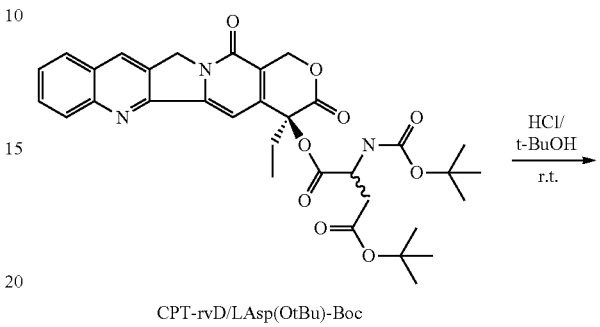

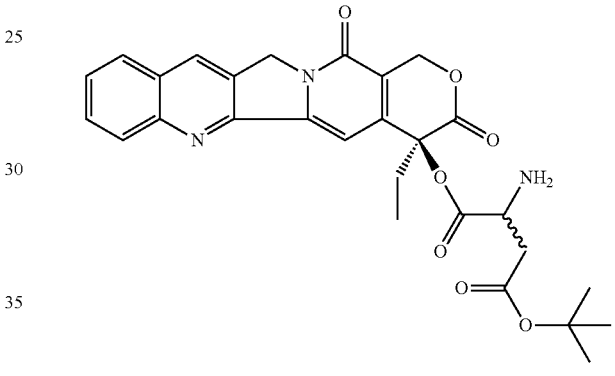

To a suspension of crude CPT-rvD/Lasp(OtBu)-Boc (1.1 g, 1.7 mmol) in t-BuOH (50 mL), 4M HCl in dioxane (50 mL) was added. The reaction mixture was stirred at room temperature for 25 minutes. Ether (900 mL) was then added and a fine yellow precipitate was obtained.

3. CPT-rvD/Lasp(OtBu)-Suc-OH

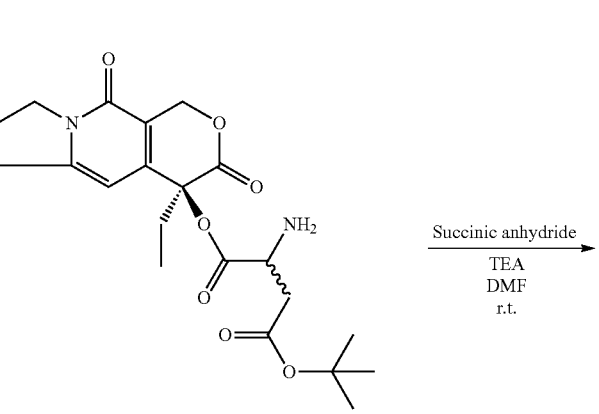

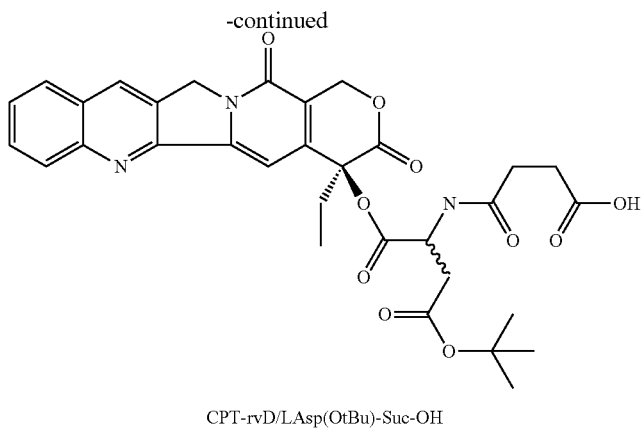

CPT-rvD/LAsp(OtBu)-Suc-OH

CPT-rvD/Lasp(OtBu)-NH₂ (1.7 mmol), obtained above, was dissolved in DMF (20 mL). Succinic anhydride (0.28 g, 2.8 mmol) and TEA (0.8 mL, 5.7 mmol) were added. The mixture was stirred at room temperature for 16 hours. The mixture was then poured into a beaker containing iced water (200 mL) and treated with concentrated HCl to obtain a pH~3. A fine yellow solid was obtained (0.72 g). HPLC analysis gave two peaks in a ratio of 4:1.

```
4. Protected Peptide
                                     (SEQ ID NO: 89)
[Tyr¹, Nle¹⁷, 4Hyp³⁴]hNPY(1-36)-Rink Amide MBHA Resin
```

The titled peptide was prepared following a similar procedure as for Examples 81.

```
5.
                                     (SEQ ID NO: 89)
[camptothecin-rvD/Lasp-Suc-Tyr¹, Nle¹⁷, 4Hyp³⁴]hNPY (1-36)-NH₂
```

Into a mixture of the protected [Tyr¹, Nle¹⁷, 4Hyp³⁴]hNPY (1-36)-Rink Amide MBHA Resin (0.125 mmol) and DMF (5 mL), CPT-rvD/Lasp(OtBu)-Suc-OH (230 mg, 0.37 mmol), HOBt (84 mg, 0.63 mmol), DIC (0.097 mL, 0.63 mmol) and DIEA (1.3 mL, 7.5 mmol) were added. A procedure similar to the procedure for Examples 81 was followed. The amount of purified material obtained was 31.0 mg. ESI-MS analysis calculated the molecular weight at 4783.8 (in agreement with the calculated molecular weight of 4784.2). Purity was 100% based on analytical HPLC analysis.

```
Example 93:
                                     (SEQ ID NO: 90)
[Camptothecin-rvD/L-Asp-Suc-Tyr¹, Nle¹⁷, A6c³¹, 4Hyp³⁴]hNPY(1-36)-NH₂;
```

[CPT-rvD/Lasp-Suc-Tyr¹, Nle¹⁷, A6c³¹, 4Hyp⁺]hNPY(1-36)-NH₂ was prepared similarly to Example 82 from CPT-rvD/Lasp(OtBu)-Suc-OH and corresponding peptide [Tyr¹, Nle¹⁷, A6c³¹, 4Hyp³⁴]hNPY(1-36)-Rink Amide MBHA Resin. The amount of purified material obtained weighed 23.0 mg. ESI-MS analysis indicated the molecular weight at 4796.0 (in agreement with the calculated molecular weight of 4796.2). Purity was 100% based on analytical HPLC analysis.

Other compounds of the invention can be prepared by a person of ordinary skill in the art using synthetic procedures analogous to those disclosed in the foregoing examples. Physical data for the compounds of Examples 1-77 and 91-107 are given in Table 1.

TABLE 1

| Example Number | Mol. Wt. (Expected) | Mol. Wt. (ESI-MS) | % Purity (HPLC) |
|---|---|---|---|
| 1 | 4212.7 | 4212.8 | 99.9 |
| 2 | 4210.6 | 4210.6 | 99.9 |
| 3 | 4180.6 | 4180.5 | 99.9 |
| 4 | 4256.7 | 4257.3 | 98.2 |
| 5 | 4254.7 | 4255.0 | 98.7 |
| 6 | 4268.7 | 4268.9 | 98.8 |
| 7 | 4268.7 | 4268.7 | 97.3 |
| 8 | 4268.7 | 4268.9 | 96.7 |
| 9 | 4254.7 | 4254.8 | 96.3 |
| 10 | 4268.7 | 4268.9 | 95.6 |
| 11 | 4226.7 | 4227.0 | 95.2 |
| 12 | 4270.7 | 4270.9 | 99.9 |
| 13 | 4227.7 | 4227.4 | 99.9 |
| 14 | 4240.7 | 4241.0 | 99.9 |
| 15 | 4270.7 | 4270.6 | 99.9 |
| 16 | 4250.7 | 4250.9 | 99.9 |
| 17 | 4226.7 | 4226.9 | 99.9 |
| 18 | 4270.7 | 4270.8 | 99.9 |
| 19 | 4270.7 | 4270.5 | 99.9 |
| 20 | 4212.7 | 4212.7 | 99.9 |
| 21 | 4226.7 | 4226.8 | 99.9 |
| 22 | 4227.7 | 4227.8 | 99.9 |
| 23 | 4284.8 | 4284.7 | 99.9 |
| 24 | 4166.6 | 4166.9 | 99.9 |
| 25 | 4166.6 | 4166.6 | 99.9 |
| 26 | 4164.7 | 4164.7 | 98.1 |
| 27 | 4150.7 | 4150.4 | 99.9 |
| 28 | 4136.6 | 4136.5 | 99.9 |
| 29 | 4180.6 | 4181.0 | 99.9 |
| 30 | 4122.6 | 4122.6 | 99.9 |
| 31 | 4196.7 | 4197.0 | 98.9 |
| 32 | 4182.7 | 4182.7 | 99.9 |
| 33 | 4180.7 | 4180.9 | 99.9 |
| 34 | 4180.6 | 4180.5 | 99.9 |
| 35 | 4206.6 | 4206.8 | 99.9 |
| 36 | 4216.6 | 4217.0 | 99.9 |
| 37 | 4230.6 | 4231.1 | 99.9 |
| 38 | 4168.6 | 4168.2 | 99.9 |
| 39 | 4138.6 | 4139.1 | 99.9 |
| 40 | 4416.1 | 4415.9 | >99 |
| 41 | 4423.1 | 4423.4 | >99 |
| 42 | 4466.1 | 4466.1 | >98 |
| 43 | 4508.2 | 4508.2 | >98 |
| 44 | 4492.2 | 4491.9 | >99 |
| 45 | 4416.1 | 4416.4 | >99 |
| 46 | 4416.1 | 4416.5 | >99 |

TABLE 1-continued

| Example Number | Mol. Wt. (Expected) | Mol. Wt. (ESI-MS) | % Purity (HPLC) |
|---|---|---|---|
| 47 | 4423.1 | 4423.2 | >97 |
| 48 | 4508.2 | 4508.4 | >99 |
| 49 | 4448.0 | 4448.2 | >99 |
| 50 | 4464.2 | 4463.7 | >99 |
| 51 | 4450.1 | 4450.5 | >99 |
| 52 | 4508.2 | 4508.3 | >99 |
| 53 | 4508.2 | 4508.4 | >99 |
| 54 | 4464.2 | 4464.9 | >99 |
| 55 | 4450.1 | 4450.3 | >99 |
| 56 | 4522.2 | 4522.2 | >99 |
| 57 | 4465.1 | 4465.1 | >99 |
| 58 | 4464.2 | 4464.2 | >99 |
| 59 | 4451.1 | 4451.2 | >99 |
| 60 | 4492.2 | 4492.0 | >99 |
| 61 | 4416.1 | 4416.3 | >99 |
| 62 | 4579.2 | 4579.2 | >99 |
| 63 | 4423.1 | 4422.8 | >99 |
| 64 | 4478.1 | 4478.1 | >99 |
| 65 | 4466.1 | 4466.3 | >99 |
| 66 | 4466.1 | 4466.3 | >99 |
| 67 | 4465.1 | 4465.2 | >99 |
| 68 | 4466.1 | 4466.1 | >99 |
| 69 | 4416.1 | 4416.4 | >99 |
| 70 | 4442.1 | 4442.4 | >99 |
| 71 | 4423.1 | 4423.2 | >99 |
| 72 | 4254.7 | 4255.4 | 97.7 |
| 73 | 4254.7 | 4255.9 | 98.2 |
| 74 | 4238.7 | 4238.5 | 99.9 |
| 75 | 4254.7 | 4254.7 | 96.5 |
| 76 | 4302.8 | 4302.7 | 98.8 |
| 77 | 4482.1 | 4482.4 | >99 |
| 90A | 4376.9 | 4377.4 | 95.2 |
| 91 | 4710.1 | 4709.9 | 97.5 |
| 92/92A | 4784.2 | 4783.8 | 100 |
| 93/93A | 4796.2 | 4796.0 | 100 |
| 94 | 4738.1 | 4738.2 | 100 |
| 95/95A | 4768.2 | 4767.9 | 100 |
| 96/96A | 4806.3 | 4806.2 | 100 |
| 97 | 4726.1 | 4726.1 | 98.6 |
| 98 | 5161.6 | 5161.7 | 100 |
| 99 | 5330.8 | 5330.7 | 99.9 |
| 100/100A | 5219.6 | 5220.2 | 99.9 |
| 101 | 5330.8 | 5331.0 | 99.9 |
| 102/102A | 5388.9 | 5389.3 | 99.9 |
| 103/103A | 5388.9 | 5389.8 | 99.9 |
| 104 | 4694.1 | 4694.8 | 99.9 |
| 105 | 4537.9 | 4538.2 | 99.9 |
| 106 | 5129.6 | 5129.3 | 99.9 |
| 107 | 5298.8 | 5298.9 | 99.9 |

In Vitro Radioligand NPY-Y1 and NPY-Y2 Receptor Binding Assays

Human neuroblastoma cell lines, SK-N-MC and SK-N-BE2 (American Type Culture Collection, Rockville, Md., USA), expressing the NPY-Y1 and NPY-Y2 receptors, respectfully, were cultured in EMEM containing 10% fetal calf serum and 5% chicken embryo extract, maintained at 37° C. in a humidified atmosphere of and 95% air and 5% $CO_2$.

For the in vitro NPY-Y1 and NPY-Y2 radioligand binding assays, the appropriate cells (SK-N-MC for NPY-Y1; SK-N-BE2 for NPY-Y2) were harvested and then homogenized in 20 ml of ice-cold 50 mM Tris-HCl with a Brinkman Polytron (Westbury, N.Y., USA) (setting 6, 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo., USA), and 0.1% BSA.

For assay, aliquots (0.4 ml) of the foregoing suspensions were incubated with 0.05 nM [$^{125}$I]PYY (2200 Ci/mmol, Perkin-Elmer, Boston, Mass.), with and without 0.05 ml of unlabeled competing test peptides or test targeted cytotoxic compounds. After a 100-minute incubation (25° C.), the bound [$^{125}$I]PYY was separated from the free by rapid filtration through GF/C filters (Brandel, Gaithersburg, Md., USA) which had been previously soaked in 0.3% polyethylene-imine. The filters were then washed three times with 5-ml aliquots of ice-cold 50 mM Tris-HCl and the bound radioactivity trapped on the filters was counted by gamma spectrometry (Wallac LKB, Gaithersburg, Md., USA). Specific binding was defined as the total [$^{125}$I]PYY bound minus that bound in the presence of 1000 nM PYY (Bachem, Torrence, Calif., USA). Inhibition constants (Ki) were calculated using the well-known Cheng-Prusoff equation and said data, together with selectivity of said compounds with respect to the NPY-Y1 and the NPY-Y2, are given in Table 2.

Each of the compounds of Examples 1-38, 40-61, 64-77, and 91-103 was subjected to the immediately foregoing radioligand assays, and nearly all of said compounds were found to have Ki of under 100 nM, as well as some of the exemplified compounds having Ki values in sub-nM range. It was also found that nearly all of said compounds highly selectively bind to the NPY-Y1 compared to the NPY-Y2.

TABLE 2

| Example Number | Ki (nM) for Y1 | Ki (nM) for Y2 | Selectivity |
|---|---|---|---|
| 1 | 0.04 | 198 | Y1 |
| 2 | 0.08 | >1000 | Y1 |
| 3 | 0.11 | 944 | Y1 |
| 4 | 0.21 | 658 | Y1 |
| 5 | 0.68 | 420 | Y1 |
| 6 | 0.31 | 319 | Y1 |
| 7 | 0.60 | 347 | Y1 |
| 8 | 3.48 | 52 | Y1 |
| 9 | 2.58 | 420 | Y1 |
| 10 | 0.98 | 578 | Y1 |
| 11 | 2.95 | 178 | Y1 |
| 12 | 1.19 | 505 | Y1 |
| 13 | 3.47 | 727 | Y1 |
| 14 | 257.27 | >1000 | Y1 |
| 15 | 0.26 | 710 | Y1 |
| 16 | 0.29 | >1000 | Y1 |
| 17 | 0.03 | 595 | Y1 |
| 18 | 0.21 | 171 | Y1 |
| 19 | 0.24 | 997 | Y1 |
| 20 | 0.20 | >1000 | Y1 |
| 21 | 0.13 | 45 | Y1 |
| 22 | 1.23 | >1000 | Y1 |
| 23 | 0.20 | >1000 | Y1 |
| 24 | 0.19 | >1000 | Y1 |
| 25 | 0.85 | 841 | Y1 |
| 26 | 0.94 | 198 | Y1 |
| 27 | 0.74 | 104 | Y1 |
| 28 | 0.18 | 441 | Y1 |
| 29 | 1.16 | >1000 | Y1 |
| 30 | 0.59 | 766 | Y1 |
| 31 | 1.91 | 202 | Y1 |
| 32 | 1.40 | 483 | Y1 |
| 33 | 239.06 | >1000 | Y1 |
| 34 | 69.78 | >1000 | Y1 |
| 35 | 3.58 | >1000 | Y1 |
| 36 | 34.23 | >1000 | Y1 |
| 37 | 52.94 | >1000 | Y1 |
| 38 | 502.28 | >1000 | Y1 |
| 39 | N/A | N/A | N/A |
| 40 | 307.67 | 367 | Y1 |
| 41 | 120.44 | 643 | Y1 |
| 42 | 3.56 | 668 | Y1 |
| 43 | 19.67 | >1000 | Y1 |
| 44 | 4.79 | 133 | Y1 |
| 45 | 10.65 | 19 | Y1 |
| 46 | 108.38 | 13 | Y2 |
| 47 | 13.66 | 15 | Y1 |
| 48 | 6.68 | 10 | Y1 |
| 49 | 54.26 | 11 | Y2 |
| 50 | 20.35 | 26 | Y1 |
| 51 | 10.00 | 611 | Y1 |

TABLE 2-continued

| Example Number | Ki (nM) for Y1 | Ki (nM) for Y2 | Selectivity |
|---|---|---|---|
| 52 | 6.18 | 383 | Y1 |
| 53 | 22.50 | 270 | Y1 |
| 54 | 4.79 | 40 | Y1 |
| 55 | 5.68 | 23 | Y1 |
| 56 | 11.82 | 41 | Y1 |
| 57 | 2.94 | 74 | Y1 |
| 58 | 3.44 | 33 | Y1 |
| 59 | 1.49 | 75 | Y1 |
| 60 | 0.55 | 138 | Y1 |
| 61 | 0.73 | 80 | Y1 |
| 62 | N/A | N/A | N/A |
| 63 | N/A | N/A | N/A |
| 64 | 87.47 | 227 | Y1 |
| 65 | 35.17 | >1000 | Y1 |
| 66 | 10.35 | 292 | Y1 |
| 67 | 29.67 | 267 | Y1 |
| 68 | 53.58 | >1000 | Y1 |
| 69 | 187.50 | 787 | Y1 |
| 70 | 8.24 | 107 | Y1 |
| 71 | 21.57 | >1000 | Y1 |
| 72 | 11.80 | 895 | Y1 |
| 73 | 9.68 | >1000 | Y1 |
| 74 | 0.48 | 466 | Y1 |
| 75 | 0.67 | 22 | Y1 |
| 76 | 1.44 | 151 | Y1 |
| 77 | 55.85 | 38 | Y2 |
| 90A | 0.84 | 672 | Y1 |
| 91 | 0.79 | >1000 | Y1 |
| 92/92A | 0.63 | >1000 | Y1 |
| 93/93A | 4.10 | >1000 | Y1 |
| 94 | 1.60 | 407 | Y1 |
| 95/95A | 3.96 | 256 | Y1 |
| 96/96A | 23.06 | 623 | Y1 |
| 97 | 1.98 | 699 | Y1 |
| 98 | 2.08 | N/A | N/A |
| 99 | 7.55 | N/A | N/A |
| 100/100A | 7.70 | N/A | N/A |
| 101 | 2.92 | N/A | N/A |
| 102/102A | 7.59 | N/A | N/A |
| 103/103A | 7.74 | N/A | N/A |

In Vivo Growth Assay

The compounds of Examples 91, 92 and 93 were evaluated in two studies, "Study A" and "Study B", each employing one group (n=10) of untreated animals, one group receiving the vehicle, and one receiving unconjugated camptothecin at 7.5 mg/kg. Once-weekly treatments were administered for three weeks by tail vein injection except in cases where poor drug solubility or tail necrosis necessitated intraperitoneal injections. Study A evaluated groups of mice receiving Example 91 at 55.65 mg/kg, 111.3 mg/kg and 222.6 mg/kg, and Example 92 at 55.3 mg/kg, 110.6 mg/kg and 221.2 mg/kg. Example 93 was evaluated in Study B at 55.45 mg/kg, 110.9 mg/kg and 221.8 mg/kg. Antitumor activity was assessed by tumor growth delay ("TGD") defined as the difference in median time to endpoint tumor size in a treatment group compared to the control group, and by tumor growth inhibition ("TGI") defined as the difference between median tumor volumes of the treatment and control groups on a study day providing a balance between measurable group responses and large group sizes. Toxicity was evaluated by body weight measurements and clinical observations.

Female nude mice (nu/nu, Harlan) were 10-11 weeks old and had body weight ranges of 20.2 to 31.1 g and 21.2 to 29.8 g on Day 1 ("Day 1" to be defined below). The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-Dri® Bed-o' Cobs® Laboratory Animal Bedding in static microisolators on a 12-hour light cycle at 21-22° C. (70-72° F.) and 40-60% humidity.

Human MCF-7 breast carcinoma cells were maintained in RPMI 1640 medium containing 100 units/mL penicillin G sodium, 100 µg/mL streptomycin sulfate, and 25 µg/mL gentamicin. The medium was supplemented with 10% heat-inactivated fetal bovine serum and 2 mM glutamine. Additional buffering was provided with 10 mM HEPES and 0.075% sodium bicarbonate. The tumor cells were cultured in tissue culture flasks in a humidified incubator at 37° C. in an atmosphere of 95% air and 5% $CO_2$.

Three to seven days prior to cell injection, a pellet containing 17-β-estradiol (0.36 mg, 60-day release, Innovative Research of America) was implanted subcutaneously between the scapulae of each mouse.

The MCF-7 tumor cells used for implantation were harvested during log phase growth and resuspended in phosphate-buffered saline at $5 \times 10^7$ cells/mL. Each mouse was injected subcutaneously in the right flank with $1 \times 10^7$ cells. Tumors were monitored twice weekly and then daily as their volumes approached 80-120 $mm^3$. On Day 18, designated as "Day 1" of Study A, animals were sorted into nine groups of mice (n=10) with individual tumor sizes ranging from 63 to 172 $mm^3$ and group mean tumor volumes of 123.7 to 124.6 $mm^3$. Because of a poor tumor take rate, insufficient animals were available for an additional three groups included in the original protocol. Thus, a separate study ("Study B") was set up comprising six groups (n=10) of animals. In this study, 17 days elapsed between cell implantation and group assignment. Individual tumor sizes on Day 1 ranged from 63 to 221 $mm^3$ and group mean tumor volumes ranged from 112.7 to 113.6 $mm^3$. Tumor size, in $mm^3$, was calculated from:

$$\text{Tumor Volume} = \frac{w^2 \times l}{2}$$

where w=width and l=length in mm of the MCF-7 tumor. Tumor weight may be estimated with the assumption that 1 mg is equivalent to 1 $mm^3$ of tumor volume.

Dosing solutions for Example 91 and Example 92 were prepared in 5% dextrose in water ("D5W") for dosing on Day 1. Because of poor solubility, dosing solutions of these agents were prepared in 0.1N acetic acid for dosing on Days 8 and 15.

Example 93 dosing solutions were prepared fresh in 0.1N acetic acid for each day of treatment. To enhance solubility, the most concentrated solution of Example 83 (221.8 mg/kg) was prepared at half-concentration, bath sonicated at 60° C., and administered in twice the volume (0.4 mL/20 g mouse) specified in the protocol.

Camptothecin (Lot No. 034K3648, Sigma) stock solutions were made from 60% DMA and 40% Tween 80 and stored at room temperature during the study. Dosing solutions were prepared fresh on each day of dosing by diluting the stocks 1:20 in saline.

The treatment plans are summarized in Table 3A for Study A and Table 3B for Study B.

TABLE 3A

| | | Treatment Regimen | | | |
|---|---|---|---|---|---|
| Group | n | Agent | mg/kg | Route | Schedule |
| 1 | 10 | No treatment | — | — | — |
| 2 | 10 | Vehicle* | — | iv | qwk x 3 |

TABLE 3A-continued

| | | Treatment Regimen | | | |
|---|---|---|---|---|---|
| Group | n | Agent | mg/kg | Route | Schedule |
| 3 | 10 | Example 91 | 55.65 | iv | qwk x 3 |
| 4 | 10 | Example 91 | 111.3 | iv | qwk x 3 |
| 5 | 10 | Example 91 | 222.6 | iv | qwk x 3 |
| 6 | 10 | Camptothecin | 7.5 | iv | qwk x 3 |
| 7 | 10 | Example 92 | 55.3 | iv | qwk x 3 |
| 8 | 10 | Example 92 | 110.6 | iv | qwk x 3 |
| 9 | 10 | Example 92 | 221.2 | iv | qwk x 3 |

*Vehicle = 0.1N acetic acid

TABLE 3B

| | | Treatment Regimen | | | |
|---|---|---|---|---|---|
| Group | n | Agent | mg/kg | Route | Schedule |
| 1 | 10 | No treatment | — | — | — |
| 2 | 10 | Vehicle** | — | ip or iv | qwk x 3 |
| 3 | 10 | Camptothecin | 7.5 | iv | qwk x 3 |
| 4 | 10 | Example 93 | 55.45 | iv | qwk x 3 |
| 5 | 10 | Example 93 | 110.9 | iv | qwk x 3 |
| 6 | 10 | Example 93 | 221.8 | iv | qwk x 3 |

**Group 2 mice received 3% DMA, 2% Tween 80, D5W vehicle, ip, on Day 1, and 0.1N acetic acid vehicle on Days 8 and 15

All treatments and vehicles were given once-weekly for three doses ("qwk×3"). Group 1 mice received no gavage and no injections, and served as a control for tumor progression and estrogen toxicity. Group 2 animals received vehicle.

In Study A (Table 3A), mice in Groups 3, 4 and 5 received the compound of Example 91 at 55.65 mg/kg, 111.3 mg/kg and 222.6 mg/kg, respectively, by intraperitoneal injection ("ip") on Day 1 and by tail-vein injection ("iv") on Days 8 and 15. Camptothecin at 7.5 mg/kg was administered to mice in Group 6, ip on Day 1 and iv on Days 8 and 15. Mice in Groups 7, 8 and 9 were given the compound of Example 92 at 55.3 mg/kg, 110.6 mg/kg and 221.2 mg/kg, respectively, ip on Day 1 and iv on Days 8 and 15.

In Study B (Table 3B), animals in Group 3 received camptothecin, 7.5 mg/kg, iv on Days 1 and 8, and ip on Day 15. Group 4, 5 and 6 mice were administered the compound of Example 93 at 55.45 mg/kg, 110.9 mg/kg and 221.8 mg/kg, iv on Days 1 and 8, and ip on Day 15.

Each treatment dose was administered in a volume of 0.2 mL per 20 g of body weight, and was scaled to the body weight of the animal.

Figure 2:
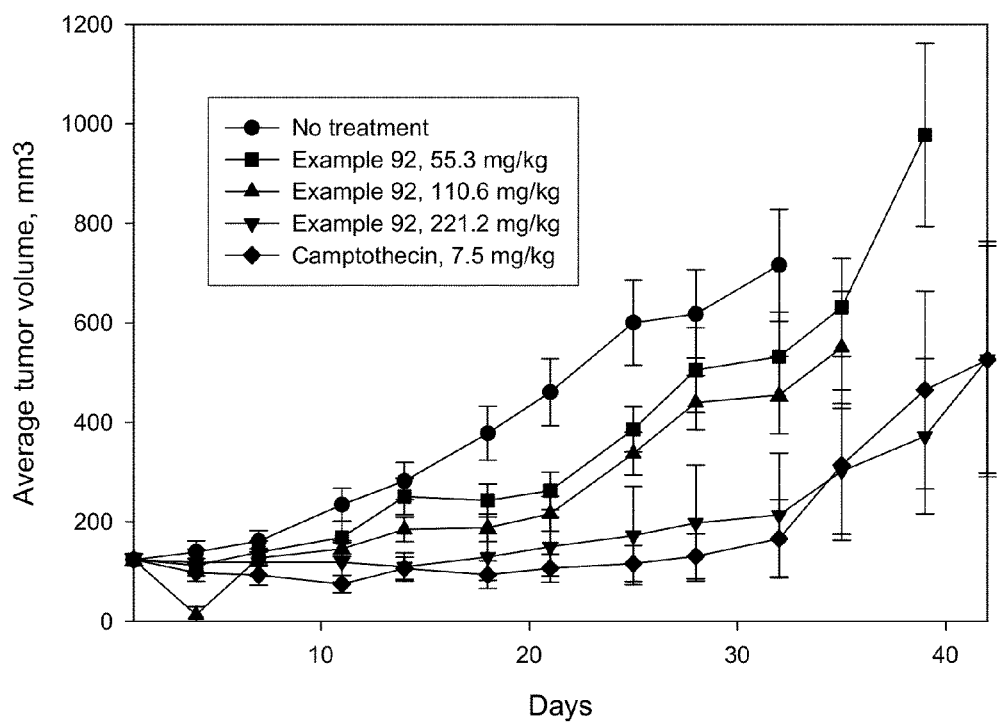
FIG. 2 shows median tumor growth curves for the compound of Example 92, which shows the in vivo effects of the compound of Example 92, at three different doses, on median tumor growth in Study A, in comparison to absence of treatment and camptothecin by itself.
Figure 3:
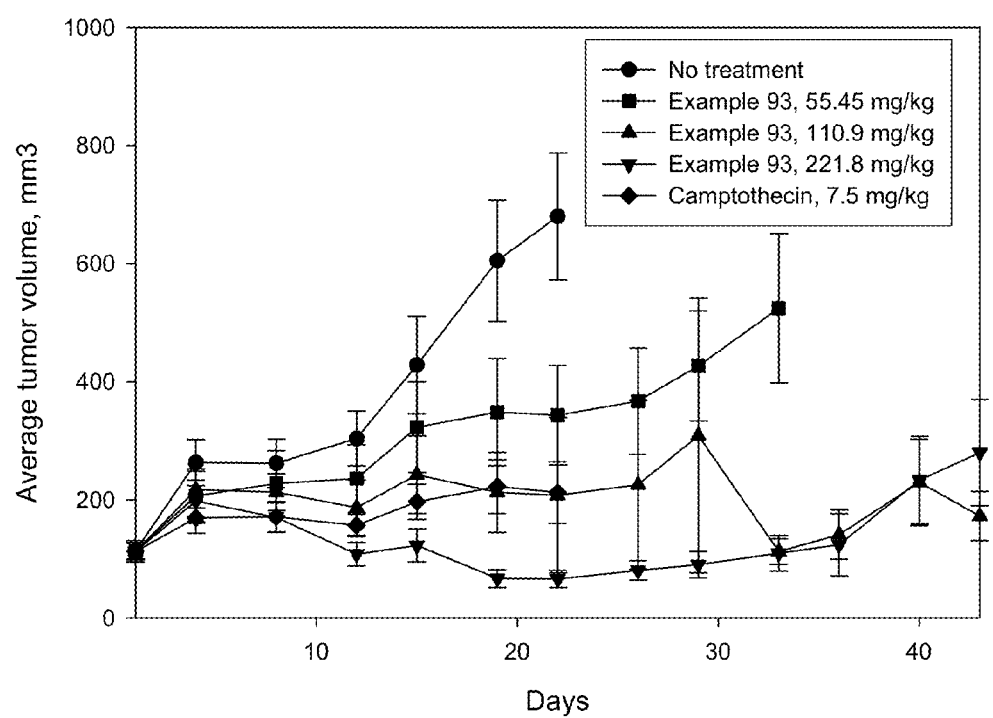
FIG. 3 shows median tumor growth curves for the compound of Example 93, which shows the in vivo effects of the compound of Example 93, at three different doses, on median tumor growth in Study B, in comparison to absence of treatment and camptothecin by itself.

Median tumor growth curves of FIGS. 1-3 show median tumor volumes as a function of time. When an animal exited the study due to tumor size, the final tumor volume recorded for the animal was included with the data used to calculate the group median tumor volume at subsequent time points. Curves were truncated after 50% of animals in a group had exited the study.

FIG. 1 shows median tumor growth curves for the compound of Example 91, which shows the in vivo effects of the compound of Example 91, at three different doses, on median tumor growth in Study A, in comparison to absence of treatment and camptothecin by itself. FIG. 2 shows median tumor growth curves for the compound of Example 92, which shows the in vivo effects of the compound of Example 92, at three different doses, on median tumor growth in Study A, in comparison to absence of treatment and camptothecin by itself. FIG. 3 shows median tumor growth curves for the compound of Example 93, which shows the in vivo effects of the compound of Example 93, at three different doses, on median tumor growth, in comparison to absence of treatment and camptothecin by itself.

The raw data from Study A are shown in Table 4A, wherein "D 1" to "D 39" refer to "Day 1" to "Day 39" as defined above, wherein "G 1" to "G 9" refer to "Group 1" to "Group 9" as defined in Table 3A, and wherein mean tumor volume ($mm^3$) is recorded corresponding to each Day and Group as shown in Table 4A.

TABLE 4A

| | D 1 | D 4 | D 7 | D 11 | D 14 | D 18 | D 21 | D 25 | D 28 | D 32 | D 35 | D 39 |
|---|---|---|---|---|---|---|---|---|---|---|---|---|
| G 1 | 123.7 | 139.3 | 161 | 234.2 | 282 | 378 | 460.6 | 600.4 | 617.7 | 715.9 | 863.8 | N/A |
| G 2 | 124.6 | 141.6 | 176.8 | 236.7 | 292.7 | 380.8 | 415.4 | 472.7 | 467 | 580.5 | 673.8 | 728.1 |
| G 3 | 124.1 | 130.4 | 166.7 | 205.8 | 264.1 | 326.8 | 347.8 | 449.1 | 545.7 | 555.3 | 521.6 | 473.3 |
| G 4 | 124.1 | 125.4 | 133.8 | 142.2 | 196 | 208.3 | 222.3 | 349.1 | 414.4 | 505.9 | 610.0 | 813 |
| G 5 | 124.1 | 84.2 | 58.8 | 41.9 | 42.3 | 31.2 | 29.6 | 29.6 | 25.9 | 33.5 | 58.8 | 66.9 |
| G 6 | 124.1 | 97.4 | 93.1 | 75 | 106.6 | 93.9 | 106.8 | 116.1 | 130.7 | 166 | 313.9 | 465 |
| G 7 | 124.1 | 112.3 | 139.2 | 168.4 | 250.9 | 242.9 | 262.5 | 385.9 | 505.1 | 532.2 | 631 | 978 |
| G 8 | 124.1 | 130.8 | 127.5 | 146 | 184.6 | 187.9 | 216.2 | 337.3 | 439.6 | 454.8 | 550.5 | 938 |
| G 9 | 124.1 | 118.3 | 118.9 | 118.8 | 109.4 | 129.5 | 150.1 | 172.2 | 197.7 | 213.8 | 301.7 | 372 |

The raw data from Study B are shown in Table 4B, wherein "D 1" to "D 40" refer to "Day 1" to "Day 40" as defined above, wherein "G 1" to "G 6" refer to "Group 1" to "Group 6" as defined in Table 3B, and wherein mean tumor volume ($mm^3$) is recorded corresponding to each Day and Group as shown in Table 4B.

TABLE 4B

| | D 1 | D 4 | D 8 | D 12 | D 15 | D 19 | D 22 | D 26 | D 29 | D 33 | D 36 | D 40 |
|---|---|---|---|---|---|---|---|---|---|---|---|---|
| G 1 | 113.6 | 262.9 | 261.9 | 304 | 428.5 | 605.1 | 679.9 | 606.8 | 615.7 | 375.8 | 403.2 | 400.2 |
| G 2 | 112.7 | 274.3 | 269.4 | 329.4 | 453.3 | 562.5 | 550.3 | 637.3 | 393.7 | 479.5 | 626 | 398 |
| G 3 | 112.8 | 169.3 | 171 | 156.7 | 196.7 | 222.3 | 212.3 | 158.9 | 120.2 | 165.6 | 197.4 | 298.6 |
| G 4 | 112.9 | 206.3 | 227.6 | 236.1 | 323.1 | 348.4 | 343.3 | 366.9 | 426.8 | 524.5 | 621.9 | 452.8 |

TABLE 4B-continued

|     | D 1   | D 4   | D 8   | D 12  | D 15  | D 19  | D 22  | D 26  | D 29  | D 33  | D 36  | D 40  |
| --- | ----- | ----- | ----- | ----- | ----- | ----- | ----- | ----- | ----- | ----- | ----- | ----- |
| G 5 | 112.8 | 217.3 | 213   | 186.6 | 242.5 | 212.6 | 207.7 | 225.5 | 308.7 | 112.3 | 141.1 | 229.5 |
| G 6 | 112.7 | 197.9 | 170.3 | 108   | 122.8 | 66.6  | 66    | 80.4  | 90.1  | 109.6 | 123.8 | 233.2 |

In Study A, the conjugate of Example 91 produced dose-related TGD that reached statistical significance at the highest dose level, 222.6 mg/kg, and 4/4 tumor regressions in the TGD-evaluated sample. TGI analysis on Day 18 revealed dose-related antitumor activity that was of potential therapeutic value at the highest dose level.

In Study A, the conjugate of Example 92 produced dose-related TGD, reaching statistical significance and producing 3/5 tumor regressions at the highest dose level, 221.2 mg/kg. Day 18 TGI was also dose-related, significantly so at 110.6 and 221.2 mg/kg, and of potential therapeutic value at the higher dose level.

Study B evaluated the conjugate of Example 93. The tumor growth curves indicated clear reduction in tumor growth at all dose levels although TGD analysis did not distinguish responses to Example 93 from tumor growth in the untreated control. Analysis on Day 15 revealed 71% and 77% TGI at the 110.9 and 221.8 mg/kg dose levels, respectively, both of potential therapeutic value.

In summary, the three conjugates evaluated in Study A and Study B showed potential therapeutic effects against the MCF-7 xenograft in nude mice. Especially at the highest dose levels evaluated, the conjugates displayed activity superior to 7.5 mg/kg unconjugated camptothecin.

Administration

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC eluting with TFA containing buffer solutions) can be converted into another salt, such as an acetate salt, by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hours, (2) 0.25N acetic acid aqueous solution for 0.5 hours, and (3) a linear gradient (20% to 100% of solution B over 30 min) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

The dosage of active ingredient in the compositions of this invention may be varied, however, it is necessary that the amount of the active ingredient be such that a suitable dosage form is obtained. The selected dosage depends upon the desired therapeutic effect, the route of administration, and the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual, or topical routes of administration, and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, without limitation, pharmaceutically acceptable emulsions, solutions, suspensions, syrups, elixirs, and the like, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include, without limitation, sterile aqueous or non-aqueous solutions, suspensions, emulsions, and the like. Examples of non-aqueous solvents or vehicles include propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtering through a bacteria-retaining filter, incorporating sterilizing agents, irradiating, or heating the compositions. They can also be manufactured in the form of sterile solid compositions which can be dissolved in sterile water, or some other sterile injectable medium, immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. PCT publication WO99/38536 teaches absorbable sustained release compositions of a bioactive agent. PCT publication WO00/04916 teaches a process for making microparticles comprising a therapeutic agent such as a peptide in an oil-in-water process. PCT publication WO00/09166 teaches complexes comprising a therapeutic agent such as a peptide and a phosphorylated polymer. PCT publication WO00/25826 teaches complexes comprising a therapeutic agent such as a peptide and a polymer bearing a non-polymerizable lactone.

Unless defined otherwise, all technical and scientific terms used herein have the same meaning as commonly understood by one of ordinary skill in the art to which this invention belongs. Also, all publications, patent applications, patents and other references mentioned herein are hereby incorporated by reference, each in its entirety.

What is claimed is:

1. A compound according to formula (I):

$$X-B^1-B^2-B^3-B^4-Z \quad (I)$$

wherein:
X is a cytotoxic or cytostatic agent;
$B^1$ is an rv(amino acid);
each of $B^2$, $B^3$, and $B^4$ is, independently for each occurrence, $(Doc)_m$, $(Aepa)_n$, or $-C(O)-W^1-W^2-W^3-W^4-W^5-C(O)-$, or deleted; and
Z is an analogue of hNPY according to the formula:

$$A^1\text{-}A^2\text{-}A^3\text{-}A^4\text{-}A^5\text{-}A^6\text{-}A^7\text{-}A^8\text{-}A^9\text{-}A^{10}\text{-}A^{11}\text{-}A^{12}\text{-}A^{13}\text{-}$$
$$A^{14}\text{-}A^{15}\text{-}A^{16}\text{-}A^{17}\text{-}A^{18}\text{-}A^{19}\text{-}A^{20}\text{-}A^{21}\text{-}A^{22}\text{-}A^{23}\text{-}$$
$$A^{24}\text{-}A^{25}\text{-}A^{26}\text{-}A^{27}\text{-}A^{28}\text{-}A^{29}\text{-}A^{30}\text{-}A^{31}\text{-}A^{32}\text{-}A^{33}\text{-}$$
$$A^{34}\text{-}A^{35}\text{-}A^{36}\text{-}A^{37}\text{-}R^1 \quad \text{(SEQ ID NO:2)}$$

wherein:
$A^1$ is Tyr or $HN-CH((CH_2)_q-N(R^2R^3))-C(O)$;
$A^2$ is Pro;
$A^3$ is Ser, Aib, or $HN-CH((CH_2)_q-N(R^2R^3))-C(O)$;
$A^4$ is Lys or $HN-CH((CH_2)_q-N(R^2R^3))-C(O)$;
$A^5$ is Pro;
$A^6$ is Asp, Aib, or $HN-CH((CH_2)_q-N(R^2R^3))-C(O)$;
$A^7$ is Asn, Aib, or $HN-CH((CH_2)_q-N(R^2R^3))-C(O)$;
$A^8$ is Pro;
$A^9$ is Gly, Aib, or $HN-CH((CH_2)_q-N(R^2R^3))-C(O)$;
$A^{10}$ is Glu, Aib, or $HN-CH((CH_2)_q-N(R^2R^3))-C(O)$;
$A^{11}$ is Asp, Aib, or $HN-CH((CH_2)_q-N(R^2R^3))-C(O)$;
$A^{12}$ is Ala, Aib, or $HN-CH((CH_2)_q-N(R^2R^3))-C(O)$;
$A^{13}$ is Pro;
$A^{14}$ is Ala, Aib, or $HN-CH((CH_2)_q-N(R^2R^3))-C(O)$;
$A^{15}$ is Glu, Aib, or $HN-CH((CH_2)_q-N(R^2R^3))-C(O)$;
$A^{16}$ is Asp, Aib, or $HN-CH((CH_2)_q-N(R^2R^3))-C(O)$;
$A^{17}$ is Met, A6c, Aib, Nle, or $HN-CH((CH_2)_q-N(R^2R^3))-C(O)$;
$A^{18}$ is Ala, Aib, or $HN-CH((CH_2)_q-N(R^2R^3))-C(O)$;
$A^{19}$ is Arg or $HN-CH((CH_2)_q-N(R^2R^3))-C(O)$;
$A^{20}$ is Tyr or $HN-CH((CH_2)_q-N(R^2R^3))-C(O)$;
$A^{21}$ is Tyr or $HN-CH((CH_2)_q-N(R^2R^3))-C(O)$;
$A^{22}$ is Ser, Aib, or $HN-CH((CH_2)_q-N(R^2R^3))-C(O)$;
$A^{23}$ is Ala, Aib, or $HN-CH((CH_2)_q-N(R^2R^3))-C(O)$;
$A^{24}$ is Leu, A6c, or $HN-CH((CH_2)_q-N(R^2R^3))-C(O)$;
$A^{25}$ is Arg or $HN-CH((CH_2)_q-N(R^2R^3))-C(O)$;
$A^{26}$ is His or $HN-CH((CH_2)_q-N(R^2R^3))-C(O)$;
$A^{27}$ is Tyr or $HN-CH((CH_2)_q-N(R^2R^3))-C(O)$;
$A^{28}$ is Ile, A6c, or $HN-CH((CH_2)_q-N(R^2R^3))C(O)$;
$A^{29}$ is Asn, Aib, or $HN-CH((CH_2)_q-N(R^2R^3))-C(O)$;
$A^{30}$ is Leu, A6c, or $HN-CH((CH_2)_q-N(R^2R^3))-C(O)$;
$A^{31}$ is Ile, Leu, or $HN-CH((CH_2)_q-N(R^2R^3))-C(O)$;
$A^{32}$ is Thr, Aib, or $HN-CH((CH_2)_q-N(R^2R^3))-C(O)$;
$A^{33}$ is Arg or $HN-CH((CH_2)_q-N(R^2R^3))-C(O)$;
$A^{34}$ is 4Hyp;
$A^{35}$ is Arg, Aic, Apc, Lys, 4NH$_2$Phe, 4NH$_2$CH$_2$Phe, or $HN-CH((CH_2)_q-N(R^2R^3))-C(O)$;
$A^{36}$ is Tyr, Aic, $HN-CH((CH_2)_q-N(R^2R^3))-C(O)$, or deleted;
$A^{37}$ is $HN-CH((CH_2)_q-N(R^2R^3))-C(O)$ or deleted;
$R^1$ is OH, NH$_2$, $(C_{1-30})$alkoxy, or $NH-X^6-CH_2-X^7$, wherein $X^6$ is a $(C_{1-40})$alkyl or $(C_{2-40})$alkenyl, and wherein $X^7$ is H, OH, CO$_2$H, or C(O)—NH$_2$;
each of $W^1$ and $W^5$ is, independently for each occurrence, $CR^4R^5$;
each of $R^4$ and $R^5$ is, independently for each occurrence, H, F, Br, Cl, I, $(C_{1-30})$alkyl, $(C_{2-30})$alkenyl, substituted $(C_{1-30})$alkyl, substituted $(C_{2-30})$alkenyl, $SR^6$, $S(O)R^7$, or $S(O)_2R^8$; or $R^4$ and $R^5$ together form a $(C_{3-30})$cycloalkyl, $(C_{3-30})$heterocycle, or $(C_{5-30})$aryl ring;
each of $R^6$, $R^7$, and $R^8$ is, independently for each occurrence, $(C_{1-30}$alkyl, $(C_{2-30}$alkenyl, substituted $(C_{1-30}$alkyl, or substituted $(C_{2-30}$alkenyl;
each of $W^2$, $W^3$, and $W^4$ is, independently for each occurrence, $CR^9R^{10}$, O, S, $(CH_2)_t$, or absent;
each of $R^9$ and $R^{10}$ is, independently for each occurrence, H, F, Br, Cl, I, $(C_{1-30}$alkyl, $(C_{2-30}$alkenyl, substituted $(C_{1-30}$alkyl, substituted $(C_{2-30}$alkenyl, $SR^6$, $S(O)R^7$, or $S(O)_2R^8$; or $R^9$ and $R^{10}$ together form a ring system;
m is, independently for each occurrence, 0, 1, 2, 3, 4, 5, 6, 7, 8, 9, or 10;

n is, independently for each occurrence, 0, 1, 2, 3, 4, 5, 6, 7, 8, 9, or 10;

q is, independently for each occurrence, 0, 1, 2, 3, 4 or 5;

t is, independently for each occurrence, 0, 1, 2, or 3; and each of $R^2$ and $R^3$ is, independently for each occurrence, H, $(C_{1-40})$alkyl, $(C_{1-40})$heteroalkyl, $(C_{1-40})$acyl, $(C_{2-40})$alkenyl, $(C_{2-40})$alkynyl, aryl$(C_{1-40})$alkyl, aryl$(C_{1-40})$acyl, substituted $(C_{1-40})$alkyl, substituted $(C_{1-40})$heteroalkyl, substituted $(C_{1-40})$acyl, substituted $(C_{2-40})$alkenyl, substituted $(C_{2-40})$alkynyl, substituted aryl$(C_{1-40})$alkyl, substituted aryl$(C_{1-40})$acyl, $(C_{1-40}$alkylsulfonyl, or C(NH)—NH$_2$, wherein when $R^2$ is $(C_{1-40})$acyl, aryl$(C_{1-40})$acyl, substituted $(C_{1-40})$acyl, substituted aryl$(C_{1-40})$acyl, $(C_{1-40})$alkylsulfonyl, or C(NH)—NH$_2$, then $R^3$ is H or $(C_1$-$C_{40})$alkyl, $(C_{1-40})$heteroalkyl, $(C_{2-40})$alkenyl, $(C_{2-40})$alkynyl, aryl$(C_{1-40})$alkyl, substituted $(C_{1-40})$alkyl, substituted $(C_{1-40})$heteroalkyl, substituted $(C_{2-40})$alkenyl, substituted $(C_{2-40})$alkynyl, or substituted aryl$(C_{1-40})$alkyl;

or a pharmaceutically acceptable salt thereof.

2. A compound according to claim 1, wherein:

said cytotoxic agent is selected from the group consisting of anthracycline, camptothecin, a camptothecin derivative, paclitaxel, a paclitaxel derivative, doxorubicin and a doxorubicin derivative;

$B^1$ is rvAsp, rvD-Asp, rvCha, rvD-Cha, or rvGly;

$B^2$ is Suc;

each of $B^3$ and $B^4$ is, independently for each occurrence, (Doc)$_m$, (Aepa)$_n$, or deleted;

$R^1$ is NH$_2$;

each of $R^2$ and $R^3$ is, independently for each occurrence, H or $(C_{1-30})$acyl;

provided that when $R^2$ is $(C_{1-30})$acyl, $R^3$ is H;

each of $R^4$ and $R^5$ is, independently for each occurrence, H or $(C_{1-40})$acyl; and q is 4;

or a pharmaceutically acceptable salt thereof.

3. A compound according to claim 2, wherein X is an anthracycline, or a pharmaceutically acceptable salt thereof.

4. A compound according to claim 2, wherein X is camptothecin or a camptothecin derivative, wherein said camptothecin derivative is:

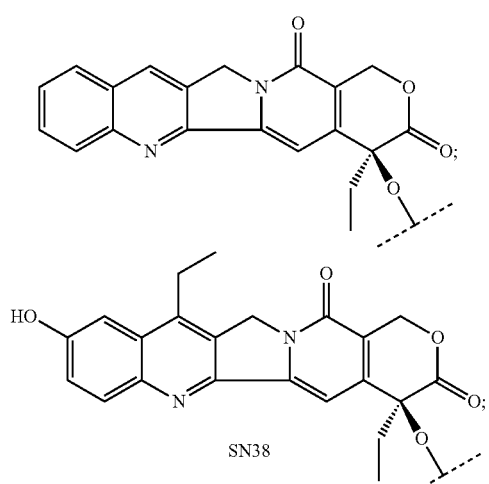

SN38

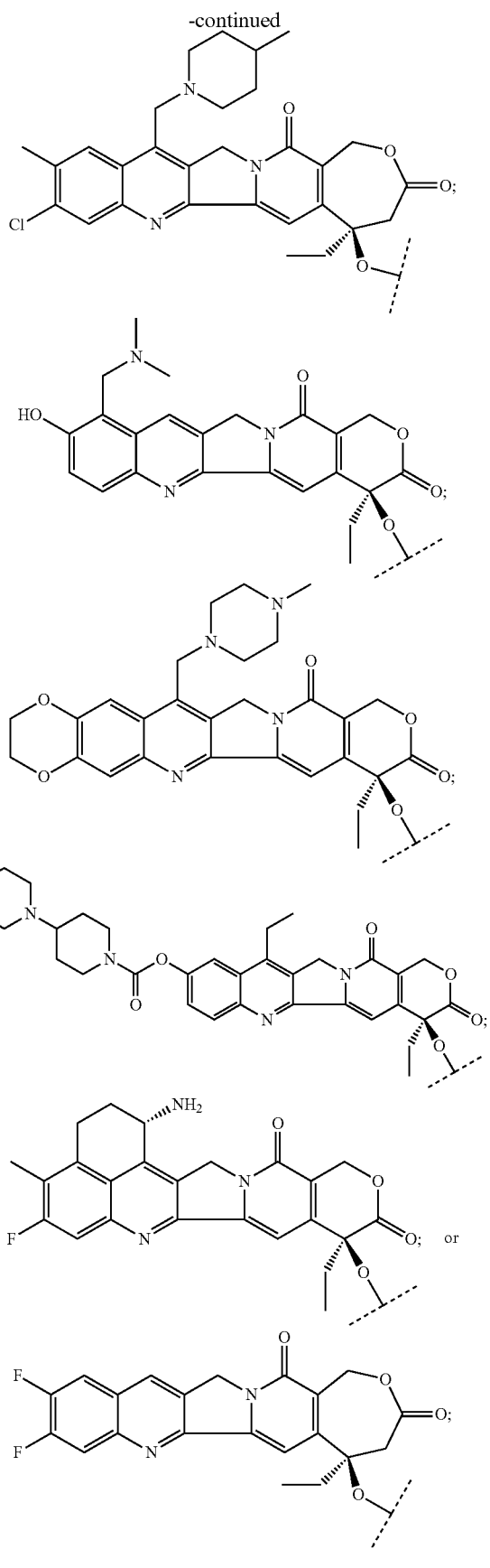

or a pharmaceutically acceptable salt thereof.

5. A compound according to claim 2, wherein X is paclitaxel or a paclitaxel derivative, wherein said paclitaxel derivative is:

[chemical structure of paclitaxel derivative]

or a pharmaceutically acceptable salt thereof.

6. A compound according to claim 2, wherein X is doxorubicin or a doxorubicin derivative, wherein said doxorubicin derivative is:

[chemical structure of doxorubicin derivative]

or a pharmaceutically acceptable salt thereof.

7. A compound according to claim 1, wherein:
$A^1$ is Tyr;
$A^3$ is Ser;
$A^4$ is Lys;
$A^6$ is Asp;
$A^7$ is Asn;
$A^9$ is Gly;
$A^{10}$ is Glu;
$A^{11}$ is Asp;
$A^{12}$ is Ala;
$A^{14}$ is Ala;
$A^{15}$ is Glu;
$A^{16}$ is Asp;
$A^{17}$ is Aib or Nle;
$A^{18}$ is Ala;
$A^{19}$ is Arg;
$A^{20}$ is Tyr;
$A^{21}$ is Tyr;
$A^{22}$ is Ser;
$A^{23}$ is Ala;
$A^{24}$ is Leu;
$A^{25}$ is Arg;
$A^{26}$ is His;
$A^{27}$ is Tyr;
$A^{28}$ is Ile;
$A^{29}$ is Asn;
$A^{30}$ is Leu;
$A^{31}$ is Ile or A6c;
$A^{32}$ is Thr;
$A^{33}$ is Arg;
$A^{35}$ is Arg or Aic;
$A^{36}$ is Tyr, Aic, or deleted; and
$A^{37}$ is deleted;
or a pharmaceutically acceptable salt thereof.

8. A compound according to claim 7, wherein X is camptothecin, or a pharmaceutically acceptable salt thereof.

9. A compound according to claim 8, wherein said compound is:
[camptothecin-rvAsp-Suc-Tyr$^1$, Nle$^{17}$, 4Hyp$^{34}$]hNPY(1-36)-NH$_2$ (SEQ ID NO:89);
[camptothecin-rvD-Asp-Suc-Tyr$^1$, Nle$^{17}$, 4Hyp$^{34}$]hNPY(1-36)-NH$_2$;
[camptothecin-rvAsp-Suc-Tyr$^1$, Nle$^{17}$, A6c$^{31}$, 4Hyp$^{34}$]hNPY(1-36)-NH$_2$ (SEQ ID NO:90);
[camptothecin-rvD-Asp-Suc-Tyr$^1$, Nle$^{17}$, A6c$^{31}$, 4Hyp$^{34}$]hNPY(1-36)-NH$_2$;
[camptothecin-rvGly-Suc-Tyr$^1$, Nle$^{17}$, A6c$^{31}$, 4Hyp$^{34}$]hNPY(1-36)-NH$_2$ (SEQ ID NO:91);
[camptothecin-rvGly-Suc-Tyr$^1$, Nle$^{17}$, 4Hyp$^{34}$]hNPY(1-36)-NH$_2$ (SEQ ID NO:94);
[camptothecin-rvGly-Suc-(Doc)$_3$-Tyr$^1$, Nle$^{17}$, 4Hyp$^{34}$]hNPY(1-36)-NH$_2$ (SEQ ID NO:95);
[camptothecin-rvGly-Suc-(Doc)$_3$-Aepa-Tyr$^1$, Nle$^{17}$, 4Hyp$^{34}$]hNPY(1-36)-NH$_2$ (SEQ ID NO:96);
[camptothecin-rvAsp-Suc-(Doc)$_3$-Tyr$^1$, Nle$^{17}$, 4Hyp$^{34}$]hNPY(1-36)-NH$_2$ (SEQ ID NO:97);
[camptothecin-rvD-Asp-Suc-(Doc)$_3$-Tyr$^1$, Nle$^{17}$, 4Hyp$^{34}$]hNPY(1-36)-NH$_2$;
[camptothecin-rvGly-Suc-Aepa-(Doc)$_3$-Tyr$^1$, Nle$^{17}$, 4Hyp$^{34}$]hNPY(1-36)-NH$_2$ (SEQ ID NO:98);
[camptothecin-rvAsp-Suc-(Doc)$_3$-Aepa-Tyr$^1$, Nle$^{17}$, 4Hyp$^{34}$]hNPY(1-36)-NH$_2$ (SEQ ID NO:99);
[camptothecin-rvD-Asp-Suc-(Doc)$_3$-Aepa-Tyr$^1$, Nle$^{17}$, 4Hyp$^{34}$]hNPY(1-36)-NH$_2$;
[camptothecin-rvAsp-Suc-Aepa-(Doc)$_3$-Tyr$^1$, Nle$^{17}$, 4Hyp$^{34}$]hNPY(1-36)-NH$_2$ (SEQ ID NO:100);
[camptothecin-rvD-Asp-Suc-Aepa-(Doc)$_3$-Tyr$^1$, Nle$^{17}$, 4Hyp$^{34}$]hNPY(1-36)-NH$_2$;
[camptothecin-rvGly-Suc-Tyr$^1$, Aib$^{17}$, 4Hyp$^{34}$, Aic$^{36}$]hNPY(1-36)-NH$_2$ (SEQ ID NO:101);
[camptothecin-rvGly-Suc-Tyr$^1$, Aib$^{17}$, 4Hyp$^{34}$, Aic$^{35}$]hNPY(1-35)-NH$_2$ (SEQ ID NO:102);
[camptothecin-rvGly-Suc-(Doc)$_3$-Tyr$^1$, Aib$^{17}$, 4Hyp$^{34}$, Aic$^{36}$]hNPY(1-36)-NH$_2$ (SEQ ID NO:103);
[camptothecin-rvGly-Suc-Aepa-(Doc)$_3$-Tyr$^1$, Aib$^{17}$, 4Hyp$^{34}$, Aic$^{36}$]hNPY(1-36)-NH$_2$ (SEQ ID NO:104);
[SN38-rvAsp-Suc-Tyr$^1$, Nle$^{17}$, 4Hyp$^{34}$]hNPY(1-36)-NH$_2$ (SEQ ID NO:107); or
[SN38-rvAsp-Suc-Tyr$^1$, Nle$^{17}$, A6c$^{31}$, 4Hyp$^{34}$]hNPY(1-36)-NH$_2$ (SEQ ID NO:108);
or a pharmaceutically acceptable salt thereof.

10. A mixture comprising [camptothecin-rvAsp-Suc-Tyr$^1$, Nle$^{17}$, 4Hyp$^{34}$]hNPY(1-36)-NH$_2$ (SEQ ID NO:89) and [camptothecin-rvD-Asp-Suc-Tyr$^1$, Nle$^{17}$, 4Hyp$^{34}$]hNPY(1-36)-NH$_2$, or a pharmaceutically acceptable salt thereof.

11. The mixture of claim 10, comprising a weight/weight ratio of about 2:98, about 5:95, about 10:90, about 15:85, about 20:80, about 25:75, about 30:70, about 35:65, about 40:60, about 45:50, about 50:50, about 55:45, about 60:40, about 65:25, about 70:30, about 75:25, about 80:20, about 85:15, about 87:13, about 88:12, about 90:10, about 95:5, about 97:3 or about 98:2 of said pair of compounds, or a pharmaceutically acceptable salt thereof.

12. A mixture comprising [camptothecin-rvAsp-Suc-Tyr$^1$, Nle$^{17}$, A6c$^{31}$, 4Hyp$^{34}$]hNPY(1-36)-NH$_2$ (SEQ ID NO:90) and [camptothecin-rvD-Asp-Suc-Tyr$^1$, Nle$^{17}$, A6c$^{31}$, 4Hyp$^{34}$]hNPY(1-36)-NH$_2$, or a pharmaceutically acceptable salt thereof.

13. The mixture of claim 12, comprising a weight/weight ratio of about 2:98, about 5:95, about 10:90, about 15:85, about 20:80, about 25:75, about 30:70, about 35:65, about 40:60, about 45:50, about 50:50, about 55:45, about 60:40, about 65:25, about 70:30, about 75:25, about 80:20, about 85:15, about 87:13, about 88:12, about 90:10, about 95:5, about 97:3 or about 98:2 of said pair of compounds, or a pharmaceutically acceptable salt thereof.

14. A compound according to claim 1, wherein Z corresponds to:

[Aib$^{10}$, 4Hyp$^{34}$]hNPY(1-36)-NH$_2$ (SEQ ID NO:3);
[Aib$^{17}$, 4Hyp$^{34}$]hNPY(1-36)-NH$_2$ (SEQ ID NO:4);
[Aib$^{11,17}$, 4Hyp$^{34}$]hNPY(1-36)-NH$_2$ (SEQ ID NO:5);
[4Hyp$^{34}$]hNPY(1-36)-NH$_2$ (SEQ ID NO:6);
[Aib$^{22}$, 4Hyp$^{34}$]hNPY(1-36)-NH$_2$ (SEQ ID NO:7);
[A6c$^{31}$, 4Hyp$^{34}$]hNPY(1-36)-NH$_2$ (SEQ ID NO:8);
[A6c$^{30}$, 4Hyp$^{34}$]hNPY(1-36)-NH$_2$ (SEQ ID NO:9);
[A6c$^{28}$, 4Hyp$^{34}$]hNPY(1-36)-NH$_2$ (SEQ ID NO:10);
[Aib$^{3}$, 4Hyp$^{34}$]hNPY(1-36)-NH$_2$ (SEQ ID NO:11);
[A6c$^{24}$, 4Hyp$^{34}$]hNPY(1-36)-NH$_2$ (SEQ ID NO:12);
[Aib$^{6}$, 4Hyp$^{34}$]hNPY(1-36)-NH$_2$ (SEQ ID NO:13);
[Aib$^{18}$, 4Hyp$^{34}$]hNPY(1-36)-NH$_2$ (SEQ ID NO:14);
[Aib$^{29}$, 4Hyp$^{34}$]hNPY(1-36)-NH$_2$ (SEQ ID NO:15);
[Aib$^{32}$, 4Hyp$^{34}$]hNPY(1-36)-NH$_2$ (SEQ ID NO:16);
[Aib$^{23}$, 4Hyp$^{34}$]hNPY(1-36)-NH$_2$ (SEQ ID NO:17);
[A6c$^{17}$, 4Hyp$^{34}$]hNPY(1-36)-NH$_2$ (SEQ ID NO:18);
[Aib$^{11}$, 4Hyp$^{34}$]hNPY(1-36)-NH$_2$ (SEQ ID NO:19);
[Aib$^{12}$, 4Hyp$^{34}$]hNPY(1-36)-NH$_2$ (SEQ ID NO:20);
[Aib$^{14}$, 4Hyp$^{34}$]hNPY(1-36)-NH$_2$ (SEQ ID NO:21);
[Aib$^{15}$, 4Hyp$^{34}$]hNPY(1-36)-NH$_2$ (SEQ ID NO:22);
[Aib$^{16}$, 4Hyp$^{34}$]hNPY(1-36)-NH$_2$ (SEQ ID NO:23);
[Aib$^{7}$, 4Hyp$^{34}$]hNPY(1-36)-NH$_2$ (SEQ ID NO:24);
[Aib$^{9}$, 4Hyp$^{34}$]hNPY(1-36)-NH$_2$ (SEQ ID NO:25);
[Aib$^{10,17}$, 4Hyp$^{34}$]hNPY(1-36)-NH$_2$ (SEQ ID NO:26);
[Aib$^{15,17}$, 4Hyp$^{34}$]hNPY(1-36)-NH$_2$ (SEQ ID NO:27);
[Aib$^{11,15}$, Nle$^{17}$, 4Hyp$^{34}$]hNPY(1-36)-NH$_2$ (SEQ ID NO:28);
[Aib$^{10,15}$, Nle$^{17}$, 4Hyp$^{34}$]hNPY(1-36)-NH$_2$ (SEQ ID NO:29);
[Aib$^{11,15,17}$, 4Hyp$^{34}$]hNPY(1-36)-NH$_2$ (SEQ ID NO:30);
[Aib$^{12,15,17}$, 4Hyp$^{34}$]hNPY(1-36)-NH$_2$ (SEQ ID NO:31);
[Aib$^{10,15,17}$, 4Hyp$^{34}$]hNPY(1-36)-NH$_2$ (SEQ ID NO:32);
[Aib$^{11,16}$, 4Hyp$^{34}$]hNPY(1-36)-NH$_2$ (SEQ ID NO:33);
[Aib$^{10,16}$, 4Hyp$^{34}$]hNPY(1-36)-NH$_2$ (SEQ ID NO:34);
[Aib$^{17}$, 4Hyp$^{34}$, Apc$^{35}$]hNPY(1-36)-NH$_2$ (SEQ ID NO:36);
[Aib$^{17}$, 4Hyp$^{34}$, Aic$^{36}$]hNPY(1-36)-NH$_2$ (SEQ ID NO:37);
[Aib$^{17}$, 4Hyp$^{34}$, 4NH$_2$Phe$^{35}$]hNPY(1-36)-NH$_2$ (SEQ ID NO:38); or
[Aib$^{17}$, 4Hyp$^{34}$, 4NH$_2$CH$_2$Phe$^{35}$]hNPY(1-36)-NH$_2$ (SEQ ID NO:39);

or a pharmaceutically acceptable salt thereof.

15. A compound according to claim 2, wherein A$^{37}$ is deleted, or a pharmaceutically acceptable salt thereof.

16. A compound according to claim 15, wherein Z corresponds to:

[Aib$^{10}$, 4Hyp$^{34}$]hNPY(1-36)-NH$_2$ (SEQ ID NO:3);
[Aib$^{17}$, 4Hyp$^{34}$]hNPY(1-36)-NH$_2$ (SEQ ID NO:4);
[Aib$^{11,17}$, 4Hyp$^{34}$]hNPY(1-36)-NH$_2$ (SEQ ID NO:5);
[4Hyp$^{34}$]hNPY(1-36)-NH$_2$ (SEQ ID NO:6);
[Aib$^{22}$, 4Hyp$^{34}$]hNPY(1-36)-NH$_2$ (SEQ ID NO:7);
[A6c$^{31}$, 4Hyp$^{34}$]hNPY(1-36)-NH$_2$ (SEQ ID NO:8);
[A6c$^{30}$, 4Hyp$^{34}$]hNPY(1-36)-NH$_2$ (SEQ ID NO:9);
[A6c$^{28}$, 4Hyp$^{34}$]hNPY(1-36)-NH$_2$ (SEQ ID NO:10);
[Aib$^{3}$, 4Hyp$^{34}$]hNPY(1-36)-NH$_2$ (SEQ ID NO:11);
[A6c$^{24}$, 4Hyp$^{34}$]hNPY(1-36)-NH$_2$ (SEQ ID NO:12);
[Aib$^{6}$, 4Hyp$^{34}$]hNPY(1-36)-NH$_2$ (SEQ ID NO:13);
[Aib$^{18}$, 4Hyp$^{34}$]hNPY(1-36)-NH$_2$ (SEQ ID NO:14);
[Aib$^{29}$, 4Hyp$^{34}$]hNPY(1-36)-NH$_2$ (SEQ ID NO:15);
[Aib$^{32}$, 4Hyp$^{34}$]hNPY(1-36)-NH$_2$ (SEQ ID NO:16);
[Aib$^{23}$, 4Hyp$^{34}$]hNPY(1-36)-NH$_2$ (SEQ ID NO:17);
[A6c$^{17}$, 4Hyp$^{34}$]hNPY(1-36)-NH$_2$ (SEQ ID NO:18);
[Aib$^{11}$, 4Hyp$^{34}$]hNPY(1-36)-NH$_2$ (SEQ ID NO:19);
[Aib$^{12}$, 4Hyp$^{34}$]hNPY(1-36)-NH$_2$ (SEQ ID NO:20);
[Aib$^{14}$, 4Hyp$^{34}$]hNPY(1-36)-NH$_2$ (SEQ ID NO:21);
[Aib$^{15}$, 4Hyp$^{34}$]hNPY(1-36)-NH$_2$ (SEQ ID NO:22);
[Aib$^{16}$, 4Hyp$^{34}$]hNPY(1-36)-NH$_2$ (SEQ ID NO:23);
[Aib$^{7}$, 4Hyp$^{34}$]hNPY(1-36)-NH$_2$ (SEQ ID NO:24);
[Aib$^{9}$, 4Hyp$^{34}$]hNPY(1-36)-NH$_2$ (SEQ ID NO:25);
[Aib$^{10,17}$, 4Hyp$^{34}$]hNPY(1-36)-NH$_2$ (SEQ ID NO:26);
[Aib$^{15,17}$, 4Hyp$^{34}$]hNPY(1-36)-NH$_2$ (SEQ ID NO:27);
[Aib$^{11,15}$, Nle$^{17}$, 4Hyp$^{34}$]hNPY(1-36)-NH$_2$ (SEQ ID NO:28);
[Aib$^{10,15}$, Nle$^{17}$, 4Hyp$^{34}$]hNPY(1-36)-NH$_2$ (SEQ ID NO:29);
[Aib$^{11,15,17}$, 4Hyp$^{34}$]hNPY(1-36)-NH$_2$ (SEQ ID NO:30);
[Aib$^{12,15,17}$, 4Hyp$^{34}$]hNPY(1-36)-NH$_2$ (SEQ ID NO:31);
[Aib$^{10,15,17}$, 4Hyp$^{34}$]hNPY(1-36)-NH$_2$ (SEQ ID NO:32);
[Aib$^{11,16}$, 4Hyp$^{34}$]hNPY(1-36)-NH$_2$ (SEQ ID NO:33);
[Aib$^{10,16}$, 4Hyp$^{34}$]hNPY(1-36)-NH$_2$ (SEQ ID NO:34);
[Aib$^{17}$, 4Hyp$^{34}$, Apc$^{35}$]hNPY(1-36)-NH$_2$ (SEQ ID NO:36);
[Aib$^{17}$, 4Hyp$^{34}$, Aic$^{36}$]hNPY(1-36)-NH$_2$ (SEQ ID NO:37);
[Aib$^{17}$, 4Hyp$^{34}$, 4NH$_2$Phe$^{35}$]hNPY(1-36)-NH$_2$ (SEQ ID NO:38); or
[Aib$^{17}$, 4Hyp$^{34}$, 4NH$_2$CH$_2$Phe$^{35}$]hNPY(1-36)-NH$_2$ (SEQ ID NO:39);

or a pharmaceutically acceptable salt thereof.

17. A compound according to claim 2, wherein the peptide bond between A$^{35}$ and A$^{36}$ is replaced by a pseudopeptide bond, or a pharmaceutically acceptable salt thereof.

18. A compound according to claim 17, wherein A$^{35}$-A$^{36}$ is Lys-ψ(CH$_2$—NH)Tyr or Lys-ψ(CH$_2$—N(Ac))Tyr, or a pharmaceutically acceptable salt thereof.

19. A compound according to claim 18, wherein Z corresponds to:

[Aib$^{11,17}$, 4Hyp$^{34}$, Lys$^{35}$-ψ(CH$_2$—N(Ac))Tyr$^{36}$]hNPY(1-36)-NH$_2$ (SEQ ID NO:35);
[Aib$^{17}$, 4Hyp$^{34}$, Lys$^{35}$-ψ(CH$_2$—NH)Tyr$^{36}$]hNPY(1-36)-N$_2$ (SEQ ID NO:40); or
[Aib$^{11,17}$, 4Hyp$^{34}$, Lys$^{35}$-ψ(CH$_2$—NH)Tyr$^{36}$]hNPY(1-36)-N$_2$ (SEQ ID NO:41);

or a pharmaceutically acceptable salt thereof.

20. A pharmaceutical composition comprising an effective amount of a compound according to claim 1, or a pharmaceutically acceptable salt thereof.

21. A pharmaceutical composition of claim 20, further comprising a pharmaceutically acceptable carrier.

* * * * *

```
                         SEQUENCE LISTING

<160> NUMBER OF SEQ ID NOS: 108

<210> SEQ ID NO 1
<211> LENGTH: 36
<212> TYPE: PRT
<213> ORGANISM: Homo sapiens
<220> FEATURE:
<221> NAME/KEY: MOD_RES
<222> LOCATION: (36)..(36)
<223> OTHER INFORMATION: terminal residue may be NH2 or OH

<400> SEQUENCE: 1

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 2
<211> LENGTH: 37
<212> TYPE: PRT
<213> ORGANISM: Artificial Sequence
<220> FEATURE:
<223> OTHER INFORMATION: Synthetic Neruopeptide Y analogs
<220> FEATURE:
<221> NAME/KEY: MISC_FEATURE
<222> LOCATION: (1)..(1)
<223> OTHER INFORMATION: Xaa = Tyr or (X1,X2,X3,X4,X5)Phe where each of
      X1, X2, X3, X4, and X5 is, independently for each occurrence, H,
      F, Cl, Br, I, (C1-10)alkyl, substituted
      (C1-10)alkyl, aryl, substituted aryl, OH, OMe, NH2 or NO2
<220> FEATURE:
<221> NAME/KEY: MISC_FEATURE
<222> LOCATION: (2)..(2)
<223> OTHER INFORMATION: Xaa =  Pro, trans-3-hydroxy-L-proline (3Hyp),
      cis-3-hydroxy-L-proline (cis-3Hyp), 4-hydroxyproline (4Hyp) or
      cis-4-hydroxy-L-proline (cis-4Hyp)
<220> FEATURE:
<221> NAME/KEY: MISC_FEATURE
<222> LOCATION: (3)..(3)
<223> OTHER INFORMATION: Xaa =  Ser, alpha-aminobutyric acid (Abu),
      alpha-aminoisobutyric acid (Aib),
      Ala or Thr
<220> FEATURE:
<221> NAME/KEY: MISC_FEATURE
<222> LOCATION: (4)..(4)
<223> OTHER INFORMATION: Xaa =  Lys, Arg, homoarginine (hArg),
      2,4-diaminobutyric acid (Dab), 2,3-diaminopropionic acid (Dap) or
      ornithine (Orn)
<220> FEATURE:
<221> NAME/KEY: MISC_FEATURE
<222> LOCATION: (5)..(5)
<223> OTHER INFORMATION: Xaa =  Pro, trans-3-hydroxy-L-proline (3Hyp),
      cis-3-hydroxy-L-proline (cis-3Hyp), 4-hydroxyproline (4Hyp) or
      cis-4-hydroxy-L-proline (cis-4Hyp)
<220> FEATURE:
<221> NAME/KEY: MISC_FEATURE
<222> LOCATION: (6)..(6)
<223> OTHER INFORMATION: Xaa =  Asp, alpha-aminoisobutyric acid (Aib),
      Asn, Gln or Glu
<220> FEATURE:
<221> NAME/KEY: MISC_FEATURE
<222> LOCATION: (7)..(7)
<223> OTHER INFORMATION: Xaa =  Asn, alpha-aminoisobutyric acid (Aib) or
```

```
              Gln
<220> FEATURE:
<221> NAME/KEY: MISC_FEATURE
<222> LOCATION: (8)..(8)
<223> OTHER INFORMATION: Xaa =  Pro, trans-3-hydroxy-L-proline (3Hyp),
      cis-3-hydroxy-L-proline (cis-3Hyp), 4-hydroxyproline (4Hyp) or
      cis-4-hydroxy-L-proline (cis-4Hyp)
<220> FEATURE:
<221> NAME/KEY: MISC_FEATURE
<222> LOCATION: (9)..(9)
<223> OTHER INFORMATION: Xaa =  Gly or alpha-aminoisobutyric acid (Aib)
<220> FEATURE:
<221> NAME/KEY: MISC_FEATURE
<222> LOCATION: (10)..(10)
<223> OTHER INFORMATION: Xaa =   Glu, alpha-aminoisobutyric acid (Aib),
      Asn, Asp or Gln
<220> FEATURE:
<221> NAME/KEY: MISC_FEATURE
<222> LOCATION: (11)..(11)
<223> OTHER INFORMATION: Xaa =   Asp, alpha-aminoisobutyric acid (Aib),
      Asn, Gln or Glu
<220> FEATURE:
<221> NAME/KEY: MISC_FEATURE
<222> LOCATION: (12)..(12)
<223> OTHER INFORMATION: Xaa =   Ala, alpha-aminobutyric acid (Abu),
      alpha-aminoisobutyric  acid (Aib),
      norvaline (Nva) or Val
<220> FEATURE:
<221> NAME/KEY: MISC_FEATURE
<222> LOCATION: (13)..(13)
<223> OTHER INFORMATION: Xaa =  Pro, trans-3-hydroxy-L-proline (3Hyp),
      cis-3-hydroxy-L-proline (cis-3Hyp), 4-hydroxyproline (4Hyp) or
      cis-4-hydroxy-L-proline (cis-4Hyp)
<220> FEATURE:
<221> NAME/KEY: MISC_FEATURE
<222> LOCATION: (14)..(14)
<223> OTHER INFORMATION: Xaa =   Ala, alpha-aminobutyric acid (Abu),
      alpha-aminoisobutyric acid (Aib),
      norvaline (Nva) or Val
<220> FEATURE:
<221> NAME/KEY: MISC_FEATURE
<222> LOCATION: (15)..(15)
<223> OTHER INFORMATION: Xaa =   Glu, alpha-aminoisobutyric acid (Aib),
      Asn, Asp or Gln
<220> FEATURE:
<221> NAME/KEY: MISC_FEATURE
<222> LOCATION: (16)..(16)
<223> OTHER INFORMATION: Xaa =   Asp, alpha-aminoisobutyric acid (Aib),
      Asn, Gln or Glu
<220> FEATURE:
<221> NAME/KEY: MISC_FEATURE
<222> LOCATION: (17)..(17)
<223> OTHER INFORMATION: Xaa = Met, 1-amino-1-cyclo(C3-9)alkyl
      carboxylic acid (Acc), alpha-aminoisobutyric acid (Aib), beta-
      cyclohexylalanine (Cha), Ile, Leu, homoleucine (hLeu), norleucine
      (Nle), tertleucine (Tle) or Val
<220> FEATURE:
<221> NAME/KEY: MISC_FEATURE
<222> LOCATION: (18)..(18)
<223> OTHER INFORMATION: Xaa =   Ala, alpha-aminobutyric acid (Abu),
      alpha-aminoisobutyric acid (Aib),
      norvaline (Nva) or Val
<220> FEATURE:
<221> NAME/KEY: MISC_FEATURE
<222> LOCATION: (19)..(19)
<223> OTHER INFORMATION: Xaa = Arg, homoarginine (hArg), 4-amino-4-
      carboxypiperidine (Apc),
      2,4-diaminobutyric acid (Dab), 2,3-diaminopropionic acid (Dap),
      Lys or ornithine (Orn)
<220> FEATURE:
<221> NAME/KEY: MISC_FEATURE
<222> LOCATION: (20)..(20)
<223> OTHER INFORMATION: Xaa = Tyr or (X1,X2,X3,X4,X5)Phe where each of
      X1, X2, X3, X4, and X5 is, independently for each occurrence, H,
      F, Cl, Br, I, (C1-10)alkyl,
      substituted (C1-10)alkyl, aryl, substituted aryl, OH, OMe, NH2,
<220> FEATURE:
<221> NAME/KEY: MISC_FEATURE
<222> LOCATION: (21)..(21)
```

```
<223> OTHER INFORMATION: Xaa = Tyr or (X1,X2,X3,X4,X5)Phe, where each of
      X1, X2, X3, X4, and X5 is, independently for each occurrence, H,
      F, Cl, Br, I, (C1-10)alkyl,
      substituted (C1-10)alkyl, aryl, substituted aryl, OH, OMe, NH2,
<220> FEATURE:
<221> NAME/KEY: MISC_FEATURE
<222> LOCATION: (22)..(22)
<223> OTHER INFORMATION: Xaa = Ser, alpha-aminobutyric acid (Abu),
      alpha-aminoisobutyric acid (Aib),
      Ala or Thr
<220> FEATURE:
<221> NAME/KEY: MISC_FEATURE
<222> LOCATION: (23)..(23)
<223> OTHER INFORMATION: Xaa = Ala, alpha-aminobutyric acid (Abu),
      alpha-aminoisobutyric acid (Aib),
      norvaline (Nva) or Val
<220> FEATURE:
<221> NAME/KEY: MISC_FEATURE
<222> LOCATION: (24)..(24)
<223> OTHER INFORMATION: Xaa = Leu, 1-amino-1-cyclo(C3-9)alkyl
      carboxylic acid (Acc), beta-
      cyclohexylalanine (Cha), Ile, homoleucine (hLeu), norleucine
      (Nle),
      norvaline (Nva), tert-leucine (Tle) or Val
<220> FEATURE:
<221> NAME/KEY: MISC_FEATURE
<222> LOCATION: (25)..(25)
<223> OTHER INFORMATION: Xaa = Arg, homoarginine (hArg), 2,4-
      diaminobutyric acid (Dab), 2,3-diaminopropionic acid (Dap), Lys or
      ornithine (Orn)
<220> FEATURE:
<221> NAME/KEY: MISC_FEATURE
<222> LOCATION: (26)..(26)
<223> OTHER INFORMATION: Xaa = His, beta-(2-pyridyl)alanine (2Pal),
      beta-(3-pyridyl)alanine (3Pal) or beta-(4-pyridyl)alanine (4Pal)
<220> FEATURE:
<221> NAME/KEY: MISC_FEATURE
<222> LOCATION: (27)..(27)
<223> OTHER INFORMATION: Xaa = Tyr or (X1,X2,X3,X4,X5)Phe where each of
      X1, X2, X3, X4, and X5 is, independently for each occurrence, H,
      F, Cl, Br, I, (C1-10)alkyl,
      substituted (C1-10)alkyl, aryl, substituted aryl, OH, OMe, NH2,
<220> FEATURE:
<221> NAME/KEY: MISC_FEATURE
<222> LOCATION: (28)..(28)
<223> OTHER INFORMATION: Xaa = Ile, 1-amino-1-cyclo(C3-9)alkyl
      carboxylic acid (Acc), beta-cyclohexylalanine (Cha), Leu,
      homoleucine (hLeu), norleucine (Nle),
      norvaline (Nva), tertleucine (Tle) or Val
<220> FEATURE:
<221> NAME/KEY: MISC_FEATURE
<222> LOCATION: (29)..(29)
<223> OTHER INFORMATION: Xaa =  Asn, alpha-aminoisobutyric acid (Aib)
      or Gln
<220> FEATURE:
<221> NAME/KEY: MISC_FEATURE
<222> LOCATION: (30)..(30)
<223> OTHER INFORMATION: Xaa = Leu, 1-amino-1-cyclo(C3-9)alkyl
      carboxylic acid (Acc), beta-
      cyclohexylalanine (Cha), Ile, homoleucine (hLeu), norleucine
      (Nle), norvaline (Nva), tert-leucine (Tle) or Val
<220> FEATURE:
<221> NAME/KEY: MISC_FEATURE
<222> LOCATION: (31)..(31)
<223> OTHER INFORMATION: Xaa = Ile, 1-amino-1-cyclo(C3-9)alkyl
      carboxylic acid (Acc), beta-
      cyclohexylalanine (Cha), Leu, homoleucine (hLeu), norleucine
      (Nle),
      norvaline (Nva), tertleucine (Tle) or Val
<220> FEATURE:
<221> NAME/KEY: MISC_FEATURE
<222> LOCATION: (32)..(32)
<223> OTHER INFORMATION: Xaa = Thr, alpha-aminoisobutyric acid (Aib) or
      Ser
<220> FEATURE:
<221> NAME/KEY: MISC_FEATURE
<222> LOCATION: (33)..(33)
<223> OTHER INFORMATION: Xaa = Arg, homoarginine (hArg), 2,4-
      diaminobutyric acid (Dab), 2,3-diaminopropionic acid (Dap), Lys or
```

-continued

```
      ornithine (Orn)
<220> FEATURE:
<221> NAME/KEY: MISC_FEATURE
<222> LOCATION: (34)..(34)
<223> OTHER INFORMATION: Xaa = Gln, Asn, 3,4-dehydroproline (Dhp),
      trans-3-hydroxy-L-proline (3Hyp), cis-3-hydroxy-L-proline
      (cis-3Hyp), 4-hydroxyproline (4Hyp), cis-4-hydroxy-L-proline
      (cis-4Hyp), isonipecotic acid (Inp), or
<220> FEATURE:
<221> NAME/KEY: MISC_FEATURE
<222> LOCATION: (34)..(34)
<223> OTHER INFORMATION: Xaa = 4-ketoproline (Ktp), nipecotic acid
      (Nip), octahydroindole-2-carboxylic
      acid (Oic), Pro, homoproline (hPro), or
      1,2,3,4-tetrahydroisoquinoline-3-carboxylic
      acid (Tic)
<220> FEATURE:
<221> NAME/KEY: MISC_FEATURE
<222> LOCATION: (35)..(35)
<223> OTHER INFORMATION: Xaa =  Arg, 2-aminoindan-2-carboxylic acid
      (Aic), 4-amino-4-carboxypiperidine (Apc), homoarginine (hArg),
       2,4-diaminobutyric
      acid (Dab), 2,3-diaminopropionic acid (Dap), Lys, ornithine
      (Orn), 4NH2Phe, or
      4NH2CH2Phe
<220> FEATURE:
<221> NAME/KEY: MISC_FEATURE
<222> LOCATION: (36)..(36)
<223> OTHER INFORMATION: Xaa = Tyr, 2-aminoindan-2-carboxylic acid
      (Aic), (X1,X2,X3,X4,X5)Phe, where each of X1, X2, X3, X4, and X5
      is, independently for each occurrence, H, F, Cl, Br, I,
      (C1-10)alkyl, or
<220> FEATURE:
<221> NAME/KEY: MISC_FEATURE
<222> LOCATION: (36)..(36)
<223> OTHER INFORMATION: Xaa = where each of X1, X2, X3, X4, and X5 is,
      independently for each occurrence, aryl, substituted aryl, OH,
      OMe, NH2, NO2, or CN
<220> FEATURE:
<221> NAME/KEY: misc_feature
<222> LOCATION: (37)..(37)
<223> OTHER INFORMATION: Xaa can be any naturally occurring amino acid

<400> SEQUENCE: 2

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa
        35

<210> SEQ ID NO 3
<211> LENGTH: 36
<212> TYPE: PRT
<213> ORGANISM: Artificial Sequence
<220> FEATURE:
<223> OTHER INFORMATION: synthetic peptide analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 3

Tyr Pro Ser Lys Pro Asp Asn Pro Gly Xaa Asp Ala Pro Ala Glu Asp
1               5                   10                  15
```

Met Ala Arg Tyr Tyr Ser Ala Leu Arg His Tyr Ile Asn Leu Ile Thr
            20                  25                  30

Arg Xaa Arg Tyr
        35

<210> SEQ ID NO 4
<211> LENGTH: 36
<212> TYPE: PRT
<213> ORGANISM: Artificial Sequence
<220> FEATURE:
<223> OTHER INFORMATION: synthetic peptide analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 4

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 5
<211> LENGTH: 36
<212> TYPE: PRT
<213> ORGANISM: Artificial Sequence
<220> FEATURE:
<223> OTHER INFORMATION: synthetic peptide analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 5

Tyr Pro Ser Lys Pro Asp Asn Pro Gly Glu Xaa Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 6
<211> LENGTH: 36
<212> TYPE: PRT
<213> ORGANISM: Artificial Sequence
<220> FEATURE:
<223> OTHER INFORMATION: synthetic peptide analog of NPY -continued

```
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 6

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 7
<211> LENGTH: 36
<212> TYPE: PRT
<213> ORGANISM: Artificial Sequence
<220> FEATURE:
<223> OTHER INFORMATION: synthetic peptide analog of NPY
<220> FEATURE:
<221> NAME/KEY: MISC_FEATURE
<222> LOCATION: (22)..(22)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 7

Tyr Pro Ser Lys Pro Asp Asn Pro Gly Glu Asp Ala Pro Ala Glu Asp
1               5                   10                  15

Met Ala Arg Tyr Tyr Xaa Ala Leu Arg His Tyr Ile Asn Leu Ile Thr
            20                  25                  30

Arg Xaa Arg Tyr
        35

<210> SEQ ID NO 8
<211> LENGTH: 36
<212> TYPE: PRT
<213> ORGANISM: Artificial Sequence
<220> FEATURE:
<223> OTHER INFORMATION: synthetic peptide analog of NPY
<220> FEATURE:
<221> NAME/KEY: MISC_FEATURE
<222> LOCATION: (31)..(31)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 8

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Xaa Thr
            20                  25                  30
```

Arg Xaa Arg Tyr
        35

<210> SEQ ID NO 9
<211> LENGTH: 36
<212> TYPE: PRT
<213> ORGANISM: Artificial Sequence
<220> FEATURE:
<223> OTHER INFORMATION: synthetic peptide analog of NPY
<220> FEATURE:
<221> NAME/KEY: MISC_FEATURE
<222> LOCATION: (30)..(30)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 9

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Xaa Ile Thr
            20                  25                  30

Arg Xaa Arg Tyr
        35

<210> SEQ ID NO 10
<211> LENGTH: 36
<212> TYPE: PRT
<213> ORGANISM: Artificial Sequence
<220> FEATURE:
<223> OTHER INFORMATION: synthetic peptide analog of NPY
<220> FEATURE:
<221> NAME/KEY: MISC_FEATURE
<222> LOCATION: (28)..(28)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 10

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Xaa Asn Leu Ile Thr
            20                  25                  30

Arg Xaa Arg Tyr
        35

<210> SEQ ID NO 11
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (3)..(3)
<223> OTHER INFORMATION: Xaa = alpha-aminoisobutyric acid (Aib)

-continued

```
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 11

Tyr Pro Xaa Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 12
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (24)..(24)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 12

Tyr Pro Ser Lys Pro Asp Asn Pro Gly Glu Asp Ala Pro Ala Glu Asp
1               5                   10                  15

Met Ala Arg Tyr Tyr Ser Ala Xaa Arg His Tyr Ile Asn Leu Ile Thr
            20                  25                  30

Arg Xaa Arg Tyr
        35

<210> SEQ ID NO 13
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (6)..(6)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 13

Tyr Pro Ser Lys Pro Xaa Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30
```

-continued

```
Arg Xaa Arg Tyr
        35

<210> SEQ ID NO 14
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (18)..(18)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 14

Tyr Pro Ser Lys Pro Asp Asn Pro Gly Glu Asp Ala Pro Ala Glu Asp
1               5                   10                  15

Met Xaa Arg Tyr Tyr Ser Ala Leu Arg His Tyr Ile Asn Leu Ile Thr
            20                  25                  30

Arg Xaa Arg Tyr
        35

<210> SEQ ID NO 15
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (29)..(29)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 15

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Xaa Leu Ile Thr
            20                  25                  30

Arg Xaa Arg Tyr
        35

<210> SEQ ID NO 16
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (32)..(32)
<223> OTHER INFORMATION: Xaa = alpha-aminoisobutyric acid (Aib)
<220> FEATURE:
<221> NAME/KEY: MISC_FEATURE
```

```
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 16

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Xaa
            20                  25                  30

Arg Xaa Arg Tyr
        35

<210> SEQ ID NO 17
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (23)..(23)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 17

Tyr Pro Ser Lys Pro Asp Asn Pro Gly Glu Asp Ala Pro Ala Glu Asp
1               5                   10                  15

Met Ala Arg Tyr Tyr Ser Xaa Leu Arg His Tyr Ile Asn Leu Ile Thr
            20                  25                  30

Arg Xaa Arg Tyr
        35

<210> SEQ ID NO 18
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 18

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Arg Tyr
```

```
<210> SEQ ID NO 19
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 19

Tyr Pro Ser Lys Pro Asp Asn Pro Gly Glu Xaa Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 20
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 20

Tyr Pro Ser Lys Pro Asp Asn Pro Gly Glu Asp Xaa Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 21
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (14)..(14)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
```

```
<220> FEATURE:
<221> NAME/KEY: MOD_RES
<222> LOCATION: (36)..(36)
<223> OTHER INFORMATION: AMIDATION

<400> SEQUENCE: 21

Tyr Pro Ser Lys Pro Asp Asn Pro Gly Glu Asp Ala Pro Xaa Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 22
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 22

Tyr Pro Ser Lys Pro Asp Asn Pro Gly Glu Asp Ala Pro Ala Xaa Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 23
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (16)..(16)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 23

Tyr Pro Ser Lys Pro Asp Asn Pro Gly Glu Asp Ala Pro Ala Glu Xaa
1               5                   10                  15

Met Ala Arg Tyr Tyr Ser Ala Leu Arg His Tyr Ile Asn Leu Ile Thr
            20                  25                  30

Arg Xaa Arg Tyr
        35
```

-continued

```
<210> SEQ ID NO 24
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (7)..(7)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 24

Tyr Pro Ser Lys Pro Asp Xaa Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 25
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (9)..(9)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 25

Tyr Pro Ser Lys Pro Asp Asn Pro Xaa Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 26
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
```

```
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 26

Tyr Pro Ser Lys Pro Asp Asn Pro Gly Xaa Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 27
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 27

Tyr Pro Ser Lys Pro Asp Asn Pro Gly Glu Asp Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 28
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION
```

```
<400> SEQUENCE: 28

Tyr Pro Ser Lys Pro Asp Asn Pro Gly Glu Xaa Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 29
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 29

Tyr Pro Ser Lys Pro Asp Asn Pro Gly Xaa Asp Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 30
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION
```

-continued

<400> SEQUENCE: 30

Tyr Pro Ser Lys Pro Asp Asn Pro Gly Glu Xaa Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 31
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 31

Tyr Pro Ser Lys Pro Asp Asn Pro Gly Glu Asp Xaa Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 32
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 32

Tyr Pro Ser Lys Pro Asp Asn Pro Gly Xaa Asp Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 33
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (16)..(16)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 33

Tyr Pro Ser Lys Pro Asp Asn Pro Gly Glu Xaa Ala Pro Ala Glu Xaa
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 34
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (16)..(16)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 34

Tyr Pro Ser Lys Pro Asp Asn Pro Gly Xaa Asp Ala Pro Ala Glu Xaa
1               5                   10                  15

Met Ala Arg Tyr Tyr Ser Ala Leu Arg His Tyr Ile Asn Leu Ile Thr
            20                  25                  30

Arg Xaa Arg Tyr
        35

```
<210> SEQ ID NO 35
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(36)
<223> OTHER INFORMATION: N-acetylated reduced psuedo-peptide bond
<220> FEATURE:
<221> NAME/KEY: MOD_RES
<222> LOCATION: (36)..(36)
<223> OTHER INFORMATION: AMIDATION

<400> SEQUENCE: 35

Tyr Pro Ser Lys Pro Asp Asn Pro Gly Glu Xaa Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Lys Tyr
        35

<210> SEQ ID NO 36
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(35)
<223> OTHER INFORMATION: Xaa = 4-amino-4-carboxypiperidine (Apc)
<220> FEATURE:
<221> NAME/KEY: MOD_RES
<222> LOCATION: (36)..(36)
<223> OTHER INFORMATION: AMIDATION

<400> SEQUENCE: 36

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Xaa Tyr
        35

<210> SEQ ID NO 37
<211> LENGTH: 36
<212> TYPE: PRT
```

```
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (36)..(36)
<223> OTHER INFORMATION: Xaa = 2-aminoindan-2-carboxylic acid (Aic)
<220> FEATURE:
<221> NAME/KEY: MOD_RES
<222> LOCATION: (36)..(36)
<223> OTHER INFORMATION: AMIDATION

<400> SEQUENCE: 37

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Arg Xaa
        35

<210> SEQ ID NO 38
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(35)
<223> OTHER INFORMATION: Xaa = 4NH2Phe
<220> FEATURE:
<221> NAME/KEY: MOD_RES
<222> LOCATION: (36)..(36)
<223> OTHER INFORMATION: AMIDATION

<400> SEQUENCE: 38

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Xaa Tyr
        35

<210> SEQ ID NO 39
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
```

```
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(35)
<223> OTHER INFORMATION: Xaa = 4NH2CH2Phe
<220> FEATURE:
<221> NAME/KEY: MOD_RES
<222> LOCATION: (36)..(36)
<223> OTHER INFORMATION: AMIDATION

<400> SEQUENCE: 39

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
                20                  25                  30

Arg Xaa Xaa Tyr
        35

<210> SEQ ID NO 40
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(36)
<223> OTHER INFORMATION: reduced psuedo-peptide bond
<220> FEATURE:
<221> NAME/KEY: MOD_RES
<222> LOCATION: (36)..(36)
<223> OTHER INFORMATION: AMIDATION

<400> SEQUENCE: 40

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
                20                  25                  30

Arg Xaa Lys Tyr
        35

<210> SEQ ID NO 41
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(36)
```

<223> OTHER INFORMATION: reduced psuedo-peptide bond
<220> FEATURE:
<221> NAME/KEY: MOD_RES
<222> LOCATION: (36)..(36)
<223> OTHER INFORMATION: AMIDATION

<400> SEQUENCE: 41

Tyr Pro Ser Lys Pro Asp Asn Pro Gly Glu Xaa Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Lys Tyr
        35

<210> SEQ ID NO 42
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (36)..(36)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 42

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Lys
        35

<210> SEQ ID NO 43
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (35)..(35)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 43

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Lys Tyr
        35

<210> SEQ ID NO 44
<211> LENGTH: 36
<212> TYPE: PRT
<213> ORGANISM: Artificial Sequence
<220> FEATURE:

```
<223> OTHER INFORMATION: synthetic analog of NPY
<220> FEATURE:
<221> NAME/KEY: MOD_RES
<222> LOCATION: (24)..(24)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 44

Tyr Pro Ser Lys Pro Asp Asn Pro Gly Glu Asp Ala Pro Ala Glu Asp
1               5                   10                  15

Met Ala Arg Tyr Tyr Ser Ala Lys Arg His Tyr Ile Asn Leu Leu Thr
            20                  25                  30

Arg Pro Arg Tyr
        35

<210> SEQ ID NO 45
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (23)..(23)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 45

Tyr Pro Ser Lys Pro Asp Asn Pro Gly Glu Asp Ala Pro Ala Glu Asp
1               5                   10                  15

Met Ala Arg Tyr Tyr Ser Lys Leu Arg His Tyr Ile Asn Leu Leu Thr
            20                  25                  30

Arg Pro Arg Tyr
        35

<210> SEQ ID NO 46
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (22)..(22)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 46

Tyr Pro Ser Lys Pro Asp Asn Pro Gly Glu Asp Ala Pro Ala Glu Asp
1               5                   10                  15

Met Ala Arg Tyr Tyr Lys Ala Leu Arg His Tyr Ile Asn Leu Leu Thr
            20                  25                  30

Arg Pro Arg Tyr
        35
```

```
<210> SEQ ID NO 47
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (21)..(21)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 47

Tyr Pro Ser Lys Pro Asp Asn Pro Gly Glu Asp Ala Pro Ala Glu Asp
1               5                   10                  15

Met Ala Arg Tyr Lys Ser Ala Leu Arg His Tyr Ile Asn Leu Leu Thr
            20                  25                  30

Arg Pro Arg Tyr
        35

<210> SEQ ID NO 48
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (20)..(20)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 48

Tyr Pro Ser Lys Pro Asp Asn Pro Gly Glu Asp Ala Pro Ala Glu Asp
1               5                   10                  15

Met Ala Arg Lys Tyr Ser Ala Leu Arg His Tyr Ile Asn Leu Leu Thr
            20                  25                  30

Arg Pro Arg Tyr
        35

<210> SEQ ID NO 49
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (19)..(19)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 49

Tyr Pro Ser Lys Pro Asp Asn Pro Gly Glu Asp Ala Pro Ala Glu Asp
1               5                   10                  15

Met Ala Lys Tyr Tyr Ser Ala Leu Arg His Tyr Ile Asn Leu Leu Thr
            20                  25                  30
```

Arg Pro Arg Tyr
         35

<210> SEQ ID NO 50
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (18)..(18)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 50

Tyr Pro Ser Lys Pro Asp Asn Pro Gly Glu Asp Ala Pro Ala Glu Asp
1               5                   10                  15

Met Lys Arg Tyr Tyr Ser Ala Leu Arg His Tyr Ile Asn Leu Leu Thr
            20                  25                  30

Arg Pro Arg Tyr
         35

<210> SEQ ID NO 51
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (17)..(17)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 51

Tyr Pro Ser Lys Pro Asp Asn Pro Gly Glu Asp Ala Pro Ala Glu Asp
1               5                   10                  15

Lys Ala Arg Tyr Tyr Ser Ala Leu Arg His Tyr Ile Asn Leu Leu Thr
            20                  25                  30

Arg Pro Arg Tyr
         35

<210> SEQ ID NO 52
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (16)..(16)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 52

Tyr Pro Ser Lys Pro Asp Asn Pro Gly Glu Asp Ala Pro Ala Glu Lys
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 53
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (15)..(15)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 53

Tyr Pro Ser Lys Pro Asp Asn Pro Gly Glu Asp Ala Pro Ala Lys Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 54
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (14)..(14)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 54

Tyr Pro Ser Lys Pro Asp Asn Pro Gly Glu Asp Ala Pro Lys Glu Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 55
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (12)..(12)
<223> OTHER INFORMATION: C(O)-(CH2)12-CH3 coupled to the epsilon-
      nitrogen of the Lys sidechain
<220> FEATURE:
<221> NAME/KEY: MOD_RES

<222> LOCATION: (36)..(36)
<223> OTHER INFORMATION: AMIDATION

<400> SEQUENCE: 55

Tyr Pro Ser Lys Pro Asp Asn Pro Gly Glu Asp Lys Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 56
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (11)..(11)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 56

Tyr Pro Ser Lys Pro Asp Asn Pro Gly Glu Lys Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 57
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (10)..(10)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 57

Tyr Pro Ser Lys Pro Asp Asn Pro Gly Lys Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 58
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (9)..(9)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 58

Tyr Pro Ser Lys Pro Asp Asn Pro Lys Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 59
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (7)..(7)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 59

Tyr Pro Ser Lys Pro Asp Lys Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 60
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (6)..(6)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 60

Tyr Pro Ser Lys Pro Lys Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
        35

<210> SEQ ID NO 61
<211> LENGTH: 36
<212> TYPE: PRT

```
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (4)..(4)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 61

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
            35

<210> SEQ ID NO 62
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (3)..(3)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 62

Tyr Pro Lys Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
            35

<210> SEQ ID NO 63
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (1)..(1)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 63

Lys Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr
            35
```

```
<210> SEQ ID NO 64
<211> LENGTH: 37
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (37)..(37)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (37)..(37)
<223> OTHER INFORMATION: AMIDATION

<400> SEQUENCE: 64

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Pro Arg Tyr Lys
        35

<210> SEQ ID NO 65
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (33)..(33)
<223> OTHER INFORMATION: C(O)-(CH2)12-CH3 coupled to the epsilon-
    nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 65

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Lys Pro Arg Tyr
        35

<210> SEQ ID NO 66
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (32)..(32)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 66

Tyr Pro Ser Lys Pro Asp Asn Pro Gly Glu Asp Ala Pro Ala Glu Asp
1               5                   10                  15
```

```
Met Ala Arg Tyr Tyr Ser Ala Leu Arg His Tyr Ile Asn Leu Leu Lys
            20                  25                  30

Arg Pro Arg Tyr
        35

<210> SEQ ID NO 67
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (31)..(31)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 67

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Lys Thr
            20                  25                  30

Arg Pro Arg Tyr
        35

<210> SEQ ID NO 68
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (30)..(30)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 68

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Lys Leu Thr
            20                  25                  30

Arg Pro Arg Tyr
        35

<210> SEQ ID NO 69
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (29)..(29)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION
```

```
<400> SEQUENCE: 69

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Lys Leu Leu Thr
            20                  25                  30

Arg Pro Arg Tyr
        35

<210> SEQ ID NO 70
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (28)..(28)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 70

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Lys Asn Leu Leu Thr
            20                  25                  30

Arg Pro Arg Tyr
        35

<210> SEQ ID NO 71
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (27)..(27)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 71

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Lys Ile Asn Leu Leu Thr
            20                  25                  30

Arg Pro Arg Tyr
        35

<210> SEQ ID NO 72
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (26)..(26)
<223> OTHER INFORMATION: C(O)-(CH2)12-CH3 coupled to the epsilon-
      nitrogen of the Lys sidechain
```

```
<220> FEATURE:
<221> NAME/KEY: MOD_RES
<222> LOCATION: (36)..(36)
<223> OTHER INFORMATION: AMIDATION

<400> SEQUENCE: 72

Tyr Pro Ser Lys Pro Asp Asn Pro Gly Glu Asp Ala Pro Ala Glu Asp
1               5                   10                  15

Met Ala Arg Tyr Tyr Ser Ala Leu Arg Lys Tyr Ile Asn Leu Leu Thr
            20                  25                  30

Arg Pro Arg Tyr
        35

<210> SEQ ID NO 73
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (25)..(25)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 73

Tyr Pro Ser Lys Pro Asp Asn Pro Gly Glu Asp Ala Pro Ala Glu Asp
1               5                   10                  15

Met Ala Arg Tyr Tyr Ser Ala Leu Lys His Tyr Ile Asn Leu Leu Thr
            20                  25                  30

Arg Pro Arg Tyr
        35

<210> SEQ ID NO 74
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = nipecotic acid (Nip)
<220> FEATURE:
<221> NAME/KEY: MOD_RES
<222> LOCATION: (36)..(36)
<223> OTHER INFORMATION: AMIDATION

<400> SEQUENCE: 74

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 75
<211> LENGTH: 36
<212> TYPE: PRT
<213> ORGANISM: Artificial Sequence
<220> FEATURE:
<223> OTHER INFORMATION: synthetic analog of NPY
<220> FEATURE:
```

<221> NAME/KEY: MISC_FEATURE
<222> LOCATION: (34)..(34)
<223> OTHER INFORMATION: Xaa = isonipecotic acid (Inp)
<220> FEATURE:
<221> NAME/KEY: MOD_RES
<222> LOCATION: (36)..(36)
<223> OTHER INFORMATION: AMIDATION

<400> SEQUENCE: 75

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 76
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = 3,4-dehydroproline (Dhp)
<220> FEATURE:
<221> NAME/KEY: MOD_RES
<222> LOCATION: (36)..(36)
<223> OTHER INFORMATION: AMIDATION

<400> SEQUENCE: 76

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 77
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = homoproline (hPro)
<220> FEATURE:
<221> NAME/KEY: MOD_RES
<222> LOCATION: (36)..(36)
<223> OTHER INFORMATION: AMIDATION

<400> SEQUENCE: 77

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 78
<211> LENGTH: 36
<212> TYPE: PRT
<213> ORGANISM: Artificial Sequence
<220> FEATURE:

```
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = 1,2,3,4-tetrahydroisoquinoline-3-
      carboxylic acid (Tic)
<220> FEATURE:
<221> NAME/KEY: MOD_RES
<222> LOCATION: (36)..(36)
<223> OTHER INFORMATION: AMIDATION

<400> SEQUENCE: 78

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 79
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (34)..(34)
<223> OTHER INFORMATION: C(O)-(CH2)12-CH3 coupled to the epsilon-
      nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 79

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Lys Arg Tyr
        35

<210> SEQ ID NO 80
<211> LENGTH: 36
<212> TYPE: PRT
<213> ORGANISM: Homo sapiens

<400> SEQUENCE: 80

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 81
<211> LENGTH: 36
<212> TYPE: PRT
<213> ORGANISM: Artificial Sequence
<220> FEATURE:
<223> OTHER INFORMATION: synthetic analog of NPY

<400> SEQUENCE: 81

Tyr Pro Ser Lys Pro Asp Asn Pro Gly Glu Asp Ala Pro Ala Glu Asp
1               5                   10                  15
```

Met Ala Arg Tyr Tyr Ser Ala Leu Arg His Tyr Ile Asn Leu Leu Thr
            20                  25                  30

Arg Pro Arg Tyr
        35

<210> SEQ ID NO 82
<211> LENGTH: 36
<212> TYPE: PRT
<213> ORGANISM: Artificial Sequence
<220> FEATURE:
<223> OTHER INFORMATION: synthetic analog of PYY

<400> SEQUENCE: 82

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Leu Thr
            20                  25                  30

Arg Pro Arg Tyr
        35

<210> SEQ ID NO 83
<211> LENGTH: 36
<212> TYPE: PRT
<213> ORGANISM: Artificial Sequence
<220> FEATURE:
<223> OTHER INFORMATION: synthetic analog of NPY

<400> SEQUENCE: 83

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Pro Arg Tyr
        35

<210> SEQ ID NO 84
<211> LENGTH: 36
<212> TYPE: PRT
<213> ORGANISM: Artificial Sequence
<220> FEATURE:
<223> OTHER INFORMATION: synthetic analog of PYY

<400> SEQUENCE: 84

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Pro Arg Tyr
        35

<210> SEQ ID NO 85
<211> LENGTH: 9
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (7)..(7)
<223> OTHER INFORMATION: Xaa = norvaline (Nva)

<400> SEQUENCE: 85

Tyr Trp Leu Ile Trp Arg Xaa Arg Tyr

```
1               5

<210> SEQ ID NO 86
<211> LENGTH: 9
<212> TYPE: PRT
<213> ORGANISM: Artificial Sequence
<220> FEATURE:
<223> OTHER INFORMATION: synthetic analog of NPY

<400> SEQUENCE: 86

Ile Asn Pro Ile Tyr Arg Leu Arg Tyr
1               5

<210> SEQ ID NO 87
<211> LENGTH: 12
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (3)..(3)
<223> OTHER INFORMATION: Xaa = norvaline (Nva)
<220> FEATURE:
<221> NAME/KEY: MOD_RES
<222> LOCATION: (6)..(7)
<223> OTHER INFORMATION: disulfide bond
<220> FEATURE:
<221> NAME/KEY: MISC_FEATURE
<222> LOCATION: (10)..(10)
<223> OTHER INFORMATION: Xaa = norvaline (Nva)

<400> SEQUENCE: 87

Tyr Arg Xaa Arg Trp Cys Cys Trp Arg Xaa Arg Tyr
1               5                   10

<210> SEQ ID NO 88
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation)
      bonded to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MOD_RES
<222> LOCATION: (38)..(38)
<223> OTHER INFORMATION: AMIDATION

<400> SEQUENCE: 88

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Pro Arg Tyr
            35

<210> SEQ ID NO 89
<211> LENGTH: 38
```

```
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 89

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
            35

<210> SEQ ID NO 90
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (33)..(33)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 90

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30
```

Xaa Thr Arg Xaa Arg Tyr
        35

<210> SEQ ID NO 91
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (33)..(33)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 91

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Xaa Thr Arg Xaa Arg Tyr
        35

<210> SEQ ID NO 92
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MOD_RES
<222> LOCATION: (38)..(38)
<223> OTHER INFORMATION: AMIDATION

<400> SEQUENCE: 92

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu

-continued

```
            20                  25                  30

Ile Thr Arg Pro Arg Tyr
        35

<210> SEQ ID NO 93
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvCha (Cha (beta-cyclohexylalanine) in
      reverse orientation) bonded to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MOD_RES
<222> LOCATION: (38)..(38)
<223> OTHER INFORMATION: AMIDATION

<400> SEQUENCE: 93

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Pro Arg Tyr
        35

<210> SEQ ID NO 94
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 94

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
```

```
<210> SEQ ID NO 95
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(8-amino-3,6-dioxaoctanoic
      acid)3 (Suc-Doc3)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 95

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
            35

<210> SEQ ID NO 96
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(8-amino-3,6-dioxaoctanoic
      acid)3-(4-(2-aminoethyl)-1-carboxy methyl-piperazine)
      (Suc-Doc3-Aepa)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 96

Xaa Xaa Tyr Pro Ser Lys Pro Asp Asn Pro Gly Glu Asp Ala Pro Ala
1               5                   10                  15
```

Glu Asp Xaa Ala Arg Tyr Tyr Ser Ala Leu Arg His Tyr Ile Asn Leu
            20                  25                  30

Ile Thr Arg Xaa Arg Tyr
        35

<210> SEQ ID NO 97
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(8-amino-3,6-dioxaoctanoic
      acid)3 (Suc-Doc3)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 97

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
        35

<210> SEQ ID NO 98
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(4-(2-aminoethyl)-1-carboxy
      methyl-piperazine)-(8-amino-3,6-dioxaoctanoic acid)3
      (Suc-Aepa-Doc3)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 98

```
Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
            35

<210> SEQ ID NO 99
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(8-amino-3,6-dioxaoctanoic
      acid)3-4-(2-aminoethyl)-1-carboxy methyl-piperazine
      (Suc-Doc3-Aepa)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 99

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
            35

<210> SEQ ID NO 100
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(4-(2-aminoethyl)-1-carboxy
      methyl-piperazine)-(8-amino-3,6-dioxaoctanoic acid)3
      (Suc-Aepa-Doc3)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
```

```
<221> NAME/KEY: MOD_RES
<222> LOCATION: (38)..(38)
<223> OTHER INFORMATION: AMIDATION

<400> SEQUENCE: 100

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
        35

<210> SEQ ID NO 101
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = alpha-aminoisobutyric acid (Aib)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MISC_FEATURE
<222> LOCATION: (38)..(38)
<223> OTHER INFORMATION: Xaa = 2-aminoindan-2-carboxylic acid (Aic)
<220> FEATURE:
<221> NAME/KEY: MOD_RES
<222> LOCATION: (38)..(38)
<223> OTHER INFORMATION: AMIDATION

<400> SEQUENCE: 101

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Xaa
        35

<210> SEQ ID NO 102
<211> LENGTH: 37
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = alpha-aminoisobutyric acid (Aib)
```

```
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MISC_FEATURE
<222> LOCATION: (37)..(37)
<223> OTHER INFORMATION: Xaa = 2-aminoindan-2-carboxylic acid (Aic)
<220> FEATURE:
<221> NAME/KEY: MOD_RES
<222> LOCATION: (37)..(37)
<223> OTHER INFORMATION: AMIDATION

<400> SEQUENCE: 102

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Xaa
            35

<210> SEQ ID NO 103
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(8-amino-3,6-dioxaoctanoic
      acid)3 (Suc-Doc3)
<220> FEATURE:
<221> NAME/KEY: MISC_FEATURE
<222> LOCATION: (19)..(19)
<223> OTHER INFORMATION: Xaa = alpha-aminoisobutyric acid (Aib)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MISC_FEATURE
<222> LOCATION: (38)..(38)
<223> OTHER INFORMATION: Xaa = 2-aminoindan-2-carboxylic acid (Aic)
<220> FEATURE:
<221> NAME/KEY: MOD_RES
<222> LOCATION: (38)..(38)
<223> OTHER INFORMATION: AMIDATION

<400> SEQUENCE: 103

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Xaa
            35

<210> SEQ ID NO 104
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
```

```
<223> OTHER INFORMATION: Xaa = rvGly (Gly in reverse orientation) bonded
      to a camptothecin moiety
<220> FEATURE:
<221> NAME/KEY: MISC_FEATURE
<222> LOCATION: (2)..(2)
<223> OTHER INFORMATION: Xaa = succinyl-(4-(2-aminoethyl)-1-carboxy
      methyl-piperazine)-(8-amino-3,6-dioxaoctanoic acid)3
      (Suc-Aepa-Doc3)
<220> FEATURE:
<221> NAME/KEY: MISC_FEATURE
<222> LOCATION: (19)..(19)
<223> OTHER INFORMATION: Xaa = alpha-aminoisobutyric acid (Aib)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MISC_FEATURE
<222> LOCATION: (38)..(38)
<223> OTHER INFORMATION: Xaa = 2-aminoindan-2-carboxylic acid (Aic)
<220> FEATURE:
<221> NAME/KEY: MOD_RES
<222> LOCATION: (38)..(38)
<223> OTHER INFORMATION: AMIDATION

<400> SEQUENCE: 104

Xaa Xaa Tyr Pro Ser Lys Pro Asp Asn Pro Gly Glu Asp Ala Pro Ala
 1               5                  10                  15

Glu Asp Xaa Ala Arg Tyr Tyr Ser Ala Leu Arg His Tyr Ile Asn Leu
            20                  25                  30

Ile Thr Arg Xaa Arg Xaa
            35

<210> SEQ ID NO 105
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = Tyr((CO)(CH2)8CH3)
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MOD_RES
<222> LOCATION: (36)..(36)
<223> OTHER INFORMATION: AMIDATION

<400> SEQUENCE: 105

Xaa Pro Ser Lys Pro Asp Asn Pro Gly Glu Asp Ala Pro Ala Glu Asp
 1               5                  10                  15

Xaa Ala Arg Tyr Tyr Ser Ala Leu Arg His Tyr Ile Asn Leu Ile Thr
            20                  25                  30

Arg Pro Arg Tyr
        35

<210> SEQ ID NO 106
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvGly (Gly in reverse orientation) bonded
      to an SN38 camptothecin moiety
```

```
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MOD_RES
<222> LOCATION: (38)..(38)
<223> OTHER INFORMATION: AMIDATION

<400> SEQUENCE: 106

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Pro Arg Tyr
            35

<210> SEQ ID NO 107
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to an SN38 camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 107

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Ile Thr Arg Xaa Arg Tyr
            35

<210> SEQ ID NO 108
<211> LENGTH: 38
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (1)..(1)
<223> OTHER INFORMATION: Xaa = rvAsp (Asp in reverse orientation) bonded
      to an SN38 camptothecin moiety
<220> FEATURE:
<221> NAME/KEY: MISC_FEATURE
<222> LOCATION: (2)..(2)
```

```
<223> OTHER INFORMATION: Xaa = succinyl (Suc)
<220> FEATURE:
<221> NAME/KEY: MISC_FEATURE
<222> LOCATION: (19)..(19)
<223> OTHER INFORMATION: Xaa = norleucine (Nle)
<220> FEATURE:
<221> NAME/KEY: MISC_FEATURE
<222> LOCATION: (33)..(33)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (36)..(36)
<223> OTHER INFORMATION: Xaa = 4-hydroxyproline (4Hyp)
<220> FEATURE:
<221> NAME/KEY: MOD_RES
<222> LOCATION: (38)..(38)
<223> OTHER INFORMATION: AMIDATION

<400> SEQUENCE: 108

Xaa Xaa Tyr Pro Ser Lys Pro Asp Asn Pro Gly Glu Asp Ala Pro Ala
1               5                   10                  15

Glu Asp Xaa Ala Arg Tyr Tyr Ser Ala Leu Arg His Tyr Ile Asn Leu
            20                  25                  30

Xaa Thr Arg Xaa Arg Tyr
        35
```